US009707244B2

(12) United States Patent
Khan et al.

(10) Patent No.: US 9,707,244 B2
(45) Date of Patent: Jul. 18, 2017

(54) COMPOSITIONS AND METHODS FOR TREATING CONDITIONS THAT AFFECT EPIDERMIS

(71) Applicant: Gencia Corporation, Charlottesville, VA (US)

(72) Inventors: Shaharyar Khan, Charlottesville, VA (US); Arthur Glenn Romero, Chesterfield, MO (US); Mikael C. Herlevsen, Crozet, VA (US)

(73) Assignee: Gencia Corporation, Charlottesville, VA (US)

(*) Notice: Subject to any disclaimer, the term of this patent is extended or adjusted under 35 U.S.C. 154(b) by 0 days.

(21) Appl. No.: 14/775,948

(22) PCT Filed: Mar. 14, 2014

(86) PCT No.: PCT/US2014/028248

§ 371 (c)(1),
(2) Date: Sep. 14, 2015

(87) PCT Pub. No.: WO2014/144017

PCT Pub. Date: Sep. 18, 2014

(65) Prior Publication Data

US 2016/0022709 A1 Jan. 28, 2016

Related U.S. Application Data

(60) Provisional application No. 61/788,959, filed on Mar. 15, 2013, provisional application No. 61/787,844, filed on Mar. 15, 2013, provisional application No. 61/866,821, filed on Aug. 16, 2013, provisional application No. 61/895,751, filed on Oct. 25, 2013, provisional application No. 61/905,631, filed on Nov. 18, 2013.

(51) Int. Cl.

| | |
|---|---|
| ***A01N 57/00*** | (2006.01) |
| ***A61K 31/685*** | (2006.01) |
| ***A61K 31/66*** | (2006.01) |
| ***A61K 38/17*** | (2006.01) |
| ***A61K 45/06*** | (2006.01) |
| ***A61K 31/4188*** | (2006.01) |
| ***A61K 31/573*** | (2006.01) |
| ***A61K 31/662*** | (2006.01) |
| ***A61K 31/7068*** | (2006.01) |
| ***A61K 8/55*** | (2006.01) |
| ***A61K 31/675*** | (2006.01) |
| ***A61Q 19/00*** | (2006.01) |
| ***A61Q 19/08*** | (2006.01) |
| ***A61K 8/64*** | (2006.01) |

(52) U.S. Cl.
CPC ................ *A61K 31/66* (2013.01); *A61K 8/55* (2013.01); *A61K 8/64* (2013.01); *A61K 31/4188* (2013.01); *A61K 31/573* (2013.01); *A61K 31/662* (2013.01); *A61K 31/675* (2013.01); *A61K 31/7068* (2013.01); *A61K 38/1709* (2013.01); *A61K 45/06* (2013.01); *A61Q 19/00* (2013.01); *A61Q 19/08* (2013.01)

(58) Field of Classification Search
USPC ........................................................... 514/85
See application file for complete search history.

(56) References Cited

U.S. PATENT DOCUMENTS

2009/0208478 A1 8/2009 Khan et al.

FOREIGN PATENT DOCUMENTS

| | | |
|---|---|---|
| WO | 2009033130 A1 | 3/2009 |
| WO | 2010045335 A1 | 4/2010 |
| WO | 2013043580 A2 | 3/2013 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
Cannon, Joseph G. "Analog Design". Burger's Medicinal Chemistry and Drug Discovery. Fifth Edition, vol. 1: Principles and Practices. Chapter 19. 1995, John Wiley & Sons, Inc.
Fischer, Frank et al. "Folic Acid and Creatine Improve the Firmness of Human Skin in vivo." Journal of Cosmetic Dermatology. vol. 10, No. 1, Mar. 21, 2011, pp. 15-23.
Murphy, Michael P. et al. "Targeting antioxidants to mitochondria by conjugation tolipophilic cations." Annual Review of Pharmacology and Toxicology, Annual Review Inc., Palo Alto, CA, US, vol. 47, Jan. 1, 2007, pp. 629-656.
Persky, A.M. et al. "Clinical Pharmacology of the Dietary Supplement Creatine Monohydrate." Pharmacological Reviews, American Society for Pharmacology and Experimental Therapeutics, US, vol. 53, No. 2, Jan. 1, 2001, pp. 161-176.
Rawson, Eric S. et al. "Use of cratine in the elderly and evidence for effects on cognitive function in young and old." Amino Acids, vol. 40, No. 5, Mar. 11, 2011, pp. 1349-1362.

* cited by examiner

*Primary Examiner* — Marcos Sznaidman
(74) *Attorney, Agent, or Firm* — Honigman Miller Schwartz and Cohn LLP; Lucy X. Yang; Jonathan P. O'Brien

(57) ABSTRACT

The present invention relates to the compositions and methods for treating or alleviating conditions that affect the epidermis (e.g., wrinkles, sun damaged skin, symptoms of aged skin, or the like).

17 Claims, 19 Drawing Sheets

Effect of rhTFAM on aged skin fibroblasts rhTFAM Uptake into
Human Reconstituted Skin

Negative Control Alexa-594 labeled rhTFAM

Mitochondrial membrane potential after rhTFAM treatment

Concentration of rhTFAM[μg/mL]

rhTFAM does not decrease fibroblast viability

Concentration of rhTFAM[Mg/mL]

Measurement of intracellular collagen

Intracellular collagen expression of individual cells plotted against cell size

MC: Mitocreatine

DEX: Dexamethasone

Betam: Betamethasone

Clobet: Clobetasol

Habituation protocol on Day 30

Running time of mice upon treatment with creatine and Mitocreatine

COMPOSITIONS AND METHODS FOR TREATING CONDITIONS THAT AFFECT EPIDERMIS

PRIORITY CLAIM

This U.S. patent application claims benefit of PCT Application No. PCT/US2014/028248 filed on Mar. 14, 2014, which claims the benefit under 35 U.S.C. §119(e) of U.S. provisional application Ser. No. 61/788,959, filed on Mar. 15, 2013; U.S. provisional application Ser. No. 61/787,844 filed on Mar. 15, 2013; U.S. provisional application Ser. No. 61/866,821, filed on Aug. 16, 2013; U.S. provisional application Ser. No. 61/895,751, filed on Oct. 25, 2013; and U.S. provisional application Ser. No. 61/905,631 filed on Nov. 18, 2013. The entire contents of the aforementioned applications are incorporated herein.

SEQUENCE LISTING

This application incorporates by reference in its entirety the Sequence Listing entitled "354903SequenceListing_ST25.txt" (46.6 kilobytes), which was created on Mar. 14, 2014 and filed electronically herewith.

FIELD OF THE INVENTION

The present invention relates to the compositions and methods for treating or alleviating conditions that affect the epidermis (e.g., wrinkles, sun damaged skin, symptoms of aged skin, or the like).

BACKGROUND OF THE INVENTION

Creatine (Cr), or 2-(carbamimidoyl-methyl-amino) acetic acid, is a naturally occurring nitrogenous organic acid synthesized in the liver of vertebrates and helps to supply energy to muscle and nerve cells. Creatine is synthesized from the amino acids arginine, methionine, and glycine through a two-step enzymatic process involving GAMT (guanidinoacetate N-methyltransferase, also known as glycine amidinotransferase) by methylation of guanidoacetate using S-adenosyl-L-methionine (SAM) as the methyl donor. Guanidoacetate is formed in the kidneys from the amino acids arginine and glycine. Once made in the liver or acquired through digestion, creatine is stored in cells including muscle and brain cells.

Several forms of the enzyme creatine (phospho)kinase (CPK or CK), exist but the most ubiquitous form of the enzyme resides in the mitochondrion, where it produces phosphocreatine from mitochondrially-generated ATP and imported creatine from the cytosol. CPK catalyzes the transfer of the phosphate from ATP to the guanidinium of creatine, forming creatine phosphate (PCr). The reaction is reversible, such that when energy demand is high (e.g., during muscle exertion or brain activity), CPK can dephosphorylate creatine phosphate and transfer the phosphate back to ADP forming ATP. This enables creatine to act as an energy storage molecule where phosphate can be stored independently of ATP.

Perturbed mitochondrial function can lead to ATP depletion, resulting in significant physiological problems. One potential method of addressing ATP depletion is to increase phosphocreatine (PCr) stores, for example by administering creatine which can be phosphorylated by CPK. Several forms of CPK exist but the most ubiquitous form of the enzyme resides in the mitochondrion, where it produces phosphocreatine from mitochondrially-generated ATP and creatine from the cytosol. However, creatine transport to the mitochondrion is an energy requiring process. Accordingly, a need remains for creatine analogs targeted to the mitochondrion to circumvent the energy loss associated with endogenous creatine transport and to provide creatine at the subcellular location of creatine action.

Skin Aging is the condition by which skin undergoes progressive degenerative change, including both structural and physiologic changes, which occur from intrinsic aging and extrinsic damage and environmental insult, including over exposure to solar radiation. Farage, Miranda A., et al. "Clinical implications of aging skin: cutaneous disorders in the elderly." American journal of clinical dermatology 10.2 (2009): 73-86. Pathologic changes include: delayed cellular migration and proliferation, loss of elasticity, decreased tensile strength, fragile, thin skin which renders it more susceptible to injury, delayed collagen remodeling, reduced epidermal hydration and greater susceptibility to solar radiation. Age and the exposure to sun are risk factors in contracting melanoma.

Creatine increase athletic performance as well as cognitive abilities in the elderly. Juhn, Mark S., and Maek Tarnopolsky. "Oral creatine supplementation and athletic performance: a critical review." Clinical journal of sport medicine: official journal of the Canadian Academy of Sport Medicine 8.4 (1998): 286; and McMorris, Terry, et al. "Creatine supplementation and cognitive performance in elderly individuals." Aging, Neuropsychology, and Cognition 14.5 (2007): 517-528. Creatine has also been shown in combination with Folic acid to increase collagen expression in fibroblasts, and a subsequent increase dermal firmness. Fischer, Frank, et al. "Folic acid and creatine improve the firmness of human skin in vivo." Journal of Cosmetic Dermatology 10.1 (2011): 15-23; Knott, Anja, et al. "A novel treatment option for photoaged skin." Journal of Cosmetic Dermatology 7.1 (2008): 15-22; and Shamban, Ava T. "Current and new treatments of photodamaged skin." Facial Plastic Surgery 11.5 (2009): 337. Creatine by itself may slow down the mutagenesis that is one of the hallmarks of photoaging. Berneburg, Mark, et al. "Creatine supplementation normalizes mutagenesis of mitochondrial DNA as well as functional consequences." Journal of investigative dermatology 125.2 (2005): 213-220.

During the treatment of cancer, many patients are administered Epidermal Growth Factor Receptor inhibitors, such as antibodies (e.g. cetuximab, panitumumab, or the like) or kinase inhibitors (e.g. gefitinib, erlotinib, or the like), and a large percentage of this patient population develop acne like skin eruptions. Segaert, Siegfried, and Eric Van Cutsem. "Clinical signs, pathophysiology and management of skin toxicity during therapy with epidermal growth factor receptor inhibitors." Annals of Oncology 16.9 (2005): 1425-1433; and Agero, Anna Liza C., et al. "Dermatologic side effects associated with the epidermal growth factor receptor inhibitors." Journal of the American Academy of Dermatology 55.4 (2006): 657-670.

76% of physicians reported delaying treatment of EGFRi at some point during therapy because of skin rash and 32% of physicians reported discontinuing EGFRi treatment altogether due to skin rash. Other anti-cancer agents such as Gemcitabine and Temozolomide may be used in combination with EGFR inhibitors or in combinations with other chemotherapeutic agents, and may also induce skin rash.

Topical glucocorticoids are highly effective for the treatment of inflammatory skin diseases and conditions. Their long-term use, however, is often accompanied by severe and partially irreversible adverse effects, with skin atrophy being the most prominent limitation. Telangiectasia and striae can appear within 2 to 3 days of starting daily application, the greatest potential occurring when the application is occluded or when the preparation is applied to fragile skin. Skin atrophy consists of a reduction in epidermal and dermal thickness, regression of the sebaceous glands, subcutaneous fat loss, and muscle-layer atrophy. These changes are typically observed following 2 to 3 weeks of moderate- to high-potency topical corticosteroid use. A single application of a very potent topical steroid can cause an ultrasonographically detectable decrease in skin thickness that lasts up to 3 days. Even low-potency topical steroids can cause slight skin atrophy that often reverses upon discontinuation of the drugs. Atrophy and striae are of concern on areas of the skin with high permeability, such as the face and intertriginous areas, but these adverse events can occur anywhere, especially after long-term use of moderate- or high-potency topical corticosteroids. While mild atrophy and telangiectasia might be reversible upon discontinuation of corticosteroids, overtly visible changes in skin texture and striae are considered permanent manifestations of corticosteroid-induced atrophy and are resistant to treatment.

There is a need to improve the function, texture, feel and appearance of the skin of a patient having wrinkles. There also exists a need to prevent, alleviate or diminish the negative side effects of cancer treatments on the patients' skin in order to increase said patients ability to tolerate prescribed anti-cancer treatments and concomitantly increase his or her quality of life. The present invention addresses these needs and others.

SUMMARY OF THE INVENTION

The present invention provides compositions and methods for treating or preventing a patient experiencing a skin condition (e.g., wrinkles, sun damaged skin, skin rash or acne), for alleviating the symptoms of aged skin, for increasing or improving the mitochondrial activity and enhancing collagen expression in the skin or eyes of an individual, or for increasing endurance and strength in an individual in need thereof.

The present invention provides compositions and methods for treating and preventing age related macular degeneration in an individual in need thereof.

The present invention further provides compositions and methods for alleviating the unwanted side effects of medical treatment of human skin or decreasing the risk of contracting melanoma.

Suitable compositions for use with the disclosed methods include creatine derivatives of Formula I

I

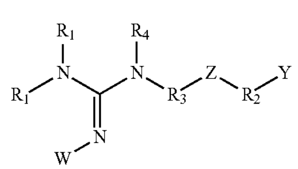

or a pharmaceutically acceptable salt thereof wherein

Z is —C(═O)$NR_5$—, —OC(═O)$NR_5$—, —$NR_7$C(═O)O—, —$NR_5$C(═O)$NR_5$—, —$SO_2NR_5$—, —$NR_5SO_2$—, —O—, —S—, —S—S—, —$CR_5$OH—, or —$CR_5$SH—; wherein each $R_5$ is independently hydrogen, alkyl, aryl, or heterocyclic;

Y is a cationic phosphonium group, or a polypeptide containing at least one positively charged amino acid residue;

Each $R_1$ is independently hydrogen, or a phosphate group;

$R_2$ is absent, alkyl, cycloalkyl, heterocycloalkyl, alkylaryl, alkylarylalkyl, or aryl;

$R_3$ is alkyl, cycloalkyl, alkylcycloalkyl, heterocycloalkyl, alkylheterocycloalkyl, alkylaryl, or alkylarylalkyl;

$R_4$ is hydrogen, alkyl, or aryl; or $R_4$ and a $R_1$ group together with the nitrogen atoms to which they are attached form a heterocyclic ring containing at least five atoms; or $R_4$ and $R_3$ together with the nitrogen atom to which they are attached form a heterocyclic ring containing at least five atoms;

at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl; or at each occurrence, an aryl is optionally substituted with 1-5 substituents independently selected from halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and CN; and W is hydrogen or alkyl.

Other suitable compositions for use with the disclosed methods include creatine derivatives of Formula II or Formula III

II

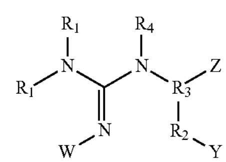

III

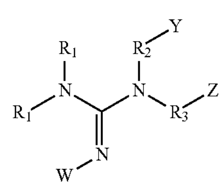

or a pharmaceutically acceptable salt thereof wherein:

Z is a functional group;

Y is a mitochondrial targeting agent, a cationic ammonium group, or a polypeptide containing at least one positively charged amino acid residue;

Each $R_1$ is independently hydrogen, alkyl, or a phosphate group;

$R_2$ is absent, or a linking group;

$R_3$ is a spacer group;

$R_4$ is hydrogen, alkyl, aryl, or heterocyclic; or $R_4$ and a $R_1$ groups together with the nitrogen atoms to which they are attached form a heterocyclic ring containing at least five atoms; or $R_4$ and $R_3$ groups together with the nitrogen atom to which they are attached forming a heterocyclic ring containing at least five atoms;

at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl;

at each occurrence, an aryl is optionally substituted with 1-5 substituents independently selected from halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and CN; and W is hydrogen or alkyl.

Other suitable compositions for use with the disclosed methods include creatine derivatives of Formula IV

IV

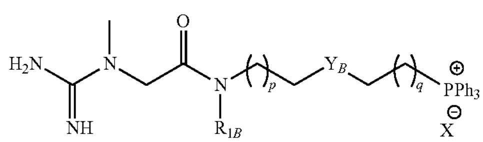

or a pharmaceutically acceptable salt thereof wherein $Y_B$ is —O—, —S—, —O—$(CH_2)_{11}$, —O—, [O—$(CH_2)_m]_n$—O—; —N($R_{2B}$)—, —NC(═O)—, —N[C(═O)$Z_B$]—, or

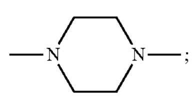

p is 1-4;

q is 1-4;

m is 2-4;

n is 1-4;

$Z_B$ is H, $C_1$-$C_6$alkyl, cycloalkylalkyl, aryl, or heteroaryl;

$R_{1B}$ is H, $C_1$-$C_6$alkyl, or cycloalkylalkyl;

$R_{2B}$ is H, $C_1$-$C_6$alkyl, or cycloalkylalkyl; and

X is pharmaceutically acceptable anion.

One embodiment of the suitable compositions for use with the disclosed methods includes a creative derivative, $N^2$-[ammonino(imino)methyl]-$N^2$-methyl-N-[3-(triphenylphosphino)propyl]glycinamide (Mitocreatine), or its pharmaceutically acceptable salt, wherein X is pharmaceutically acceptable anion such as chloride or trifluoroacetate. Mitocreatine has the following structure:

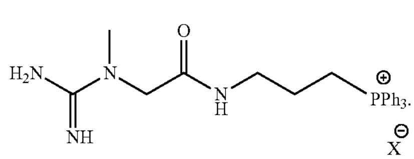

Other suitable compositions for use with the disclosed methods include a recombinant transcription factor A-mitochondrial (TFAM) or a TFAM fusion protein, or a recombinant polypeptide comprising a protein transduction domain, a mitochondrial localization signal, and a mature TFAM. One embodiment of the suitable compositions for use with the disclosed methods includes rhTFAM.

The present invention further provides a pharmaceutical composition for treating or preventing a patient experiencing a skin condition (e.g., wrinkles, sun damaged skin, skin rash or acne), for alleviating the symptoms of aged skin, for increasing or improving the mitochondrial activity and enhancing collagen expression in the skin or eyes of an individual, for increasing endurance and strength in an individual in need thereof, for treating and preventing age related macular degeneration in an individual in need thereof, for alleviating the unwanted side effects of medical treatment of human skin, or for decreasing the risk of contracting melanoma; comprises a compound of Formulas I-IV as defined above, or a recombinant transcription factor A-mitochondrial (TFAM) or a TFAM fusion protein, or a recombinant polypeptide comprising a protein transduction domain, a mitochondrial localization signal, and a mature TFAM.

Use of a compound of Formulas I-IV as defined above, or a recombinant transcription factor A-mitochondrial (TFAM) or a TFAM fusion protein, or a recombinant polypeptide comprising a protein transduction domain, a mitochondrial localization signal, and a mature TFAM for manufacture of a medicament for treating or preventing a patient experiencing a skin condition (e.g., wrinkles, sun damaged skin, skin rash or acne), for alleviating the symptoms of aged skin, for increasing or improving the mitochondrial activity and enhancing collagen expression in the skin or eyes of an individual, for increasing endurance and strength in an individual in need thereof, for treating and preventing age related macular degeneration in an individual in need thereof, for alleviating the unwanted side effects of medical treatment of human skin, or for decreasing the risk of contracting melanoma.

DETAILED DESCRIPTION OF THE INVENTION

I. Definitions

Figure 1:
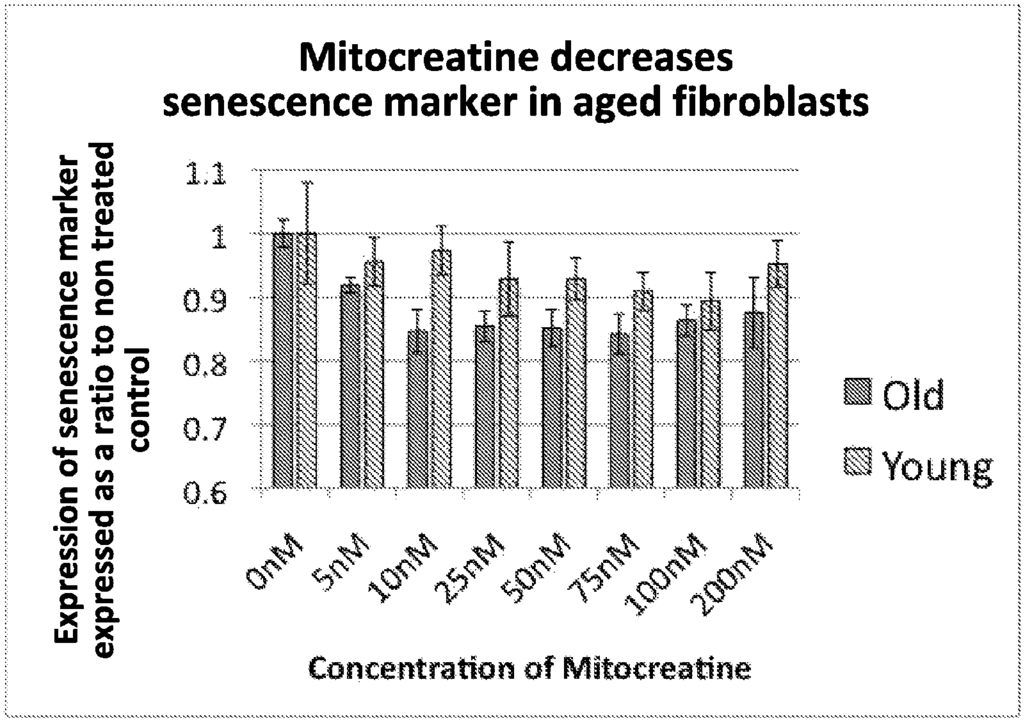
FIG. 1 depicts a bar graph showing expression of senescence marker when untransformed fibroblasts from young (12 years old) and old (75 years old) individuals were treated with increasing amounts of Mitocreatine.

In describing and claiming the disclosed subject matter, the following terminology will be used in accordance with the definitions set forth below.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The carbon atom content of various hydrocarbon-containing moieties is indicated by a prefix designating the minimum and maximum number of carbon atoms in the moiety, i.e., the prefix $C_{i-j}$ or $C_i$-$C^j$ indicates a moiety of the integer "i" to the integer "j" carbon atoms, inclusive. Thus, for example, $C_{1-4}$ alkyl refers to alkyl of one to four carbon atoms, inclusive.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more particularly 20 or fewer carbon atoms, more particularly 12 or fewer carbon atoms, and most particularly 8 or fewer carbon atoms. Likewise, some cycloalkyls have from 3-10 carbon atoms in their ring structure, and more particularly have 5, 6 or 7 carbons in the ring structure. The ranges provided above are inclusive of all values between the minimum value and the maximum value.

The alkyl groups may also be substituted with one or more groups including, but not limited to, halogen, hydroxy, amino, thio, ether, ester, carboxy, oxo, and aldehyde groups. The alkyl groups may also contain one or more heteroatoms within the carbon backbone. Particularly the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bond analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and particularly from 5-6 ring atoms, consisting of carbon and one to four heteroatoms each selected from the group consisting of non-peroxide oxygen, sulfur, and N(Y) wherein Y is absent or is H, O, $(C_{1-4})$ alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, $(C_1-C_8)$ alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, particularly 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "pharmaceutically acceptable salt", as used herein, refers to derivatives of the compounds defined herein, wherein the parent compound is modified by making acid or base salts thereof, and/or a phosphonium or ammonium cation is present. Examples of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable acid or base salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are examples. When selected to be present, the anion counter-ion for the phosphonium ion may be prepared by a variety of methods, including the direct result of the quaternization of the phosphine and the application of ion-exchange to replace one counter-ion for another. Lists of suitable salts and counter-ions are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. Pharmaceutically acceptable carriers and/or excipients include those include compounds or materials generally recognized as safe (GRAS) by the U.S. Food and Drug Administration.

The term "host," as used herein, refers to a multicellular organism having mitochondria including but not limited to mammals such as primates, humans, dogs, cats, cows, pigs, sheep, and the like.

The term "mitochondrial metabolite," as used herein, refers to an organic compound that is a starting material in, an intermediate in, or an end product of metabolism occurring in the mitochondria.

The term "operably linked," as used herein, refers to a juxtaposition wherein the components are configured so as to perform their usual function. For example, a mitochondrial targeting agent operably linked to a compound will direct the linked compound to be localized to the mitochondria. In some embodiments, the linked compound maintains biological activity in the mitochondria. Alternatively, the compound can be released by cleavage of the linker or functional group that binds the compound to the targeting agent. The functional group or linker can be cleaved by a variety of mechanisms including hydrolysis and enzymatic cleavage.

The term "prodrug," as used herein, refers to a pharmacological substance (drug) which is administered in an inactive (or significantly less active) form. Once administered, the prodrug is metabolized in the body (in vivo) into the active compound.

The term "creatine subunit," as used herein, refers to a portion of a compound having a chemical structure derived from creatine. Creatine subunits typically include a guanidine or modified guanidine moiety, a spacer group, and a functional group.

The term "spacer group," as used herein, refers to a portion of the creatine subunit which connects the guanidine or modified guanidine moiety to the functional group.

The term "linker" or "linking group," as used herein, refer to a group or moiety which is at minimum bivalent, and connects a creatine subunit to an agent. The linker can be composed of any assembly of atoms, including oligomeric and polymeric chains; however, the total number of atoms in the spacer group is particularly between 3 and 200 atoms, more particularly between 3 and 150 atoms, more particularly between 3 and 100 atoms, most particularly between 3 and 50 atoms. In some embodiments, the linker is hydrophilic. In some embodiments, the linker is an alkyl group, an alkylaryl group, an oligo- or polyethylene glycol chain, or an oligo- or poly(amino acid) chain. In some embodiments, the linker may also include one or more cleavable subunits, such as a disulfide group, one or more hydrolysable functional groups, such as an ester or amide, one or more metal complexes, such as a polyhistidine-nickel chelate complex, one or more hydrogen bond donor-acceptor pairs, one or more biomolecule/bioconjugate pairs (such as biotin-avidin or biotin-streptavidin pair), as well as combinations thereof.

The term "therapeutically effective," as used herein, means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art could readily determine the proper therapeutic amount.

The terms "analog" and "derivative" are used herein interchangeably and refer to a compound having a structure similar to that a parent compound, but varying from the parent compound by a difference in one or more certain components. The analog or derivative can differ from the parent compound in one or more atoms, functional groups, or substructures, which are replaced with other atoms, groups, or substructures. An analog or derivative can be imagined to be formed, at least theoretically, from the parent compound via some chemical or physical process.

In some embodiments, multiple agents are connected to a single linker, which is connected to a creatine subunit. In other embodiments, the creatine subunit is substituted at multiple locations with one or more agents, optionally connected via a linker.

In the case of creatine derivatives, the creatine subunit, linker, and one or more agents can be any of those described below. In some cases, agent is a targeting agent which functions to selectively localize the modified creatine moiety within a cell.

In some embodiments, creatine derivatives contain a creatine subunit attached to a mitochondrial targeting agent. In some cases, the creatine subunit is directly attached to the mitochondrial targeting agent. In other embodiments, the mitochondrial targeting agent is attached to the creatine subunit through a linker. The linker can be connected to any portion of the creatine subunit, such as to the guanidine moiety, the spacer group, or the functional group.

In some embodiments, the creatine derivatives can be targeted to selectively localize within a cell by linking the creatine compounds to a targeting agent. In one embodiment, the modified creatine compounds contain a creatine subunit linked, attached, conjugated, associated with, or functionalized to one or more mitochondrial targeting agents. In some instances, the creatine moiety retains its biological activity when linked to the targeting agent.

In some embodiments, upon entering the mitochondria, the creatine moiety is cleaved from the targeting agent. The creatine moiety can be released by a variety of mechanisms including simple hydrolysis or enzymatically. In one embodiment, the creatine moiety is bound directly to the targeting agent and the creatine moiety is released hydrolytically and/or enzymatically. In another embodiment, the creatine moiety is bound to the targeting agent via a linker and the linker is cleaved hydrolytically and/or enzymatically.

In some embodiments, the linker is a non-peptide linker which is cleaved within the mitochondria. In other embodiments, the linker is a peptide linker which is cleaved within the mitochondria. In still other embodiments, the creatine moiety is not cleaved from the targeting agent, provided the creatine moiety retains the desired biological activity.

Exemplary creatine derivatives include, but are not limited to those shown in Table 2.

In certain embodiments, the creatine derivatives are therapeutically active in their dosed structural form. In some cases, the dosed structural form serves as a pro-drug, which reacts or is metabolized in vivo to form a compound which is therapeutically active. In such cases it is possible that both the pro-drug and the liberated drug each intrinsically possess activity, although typically at significantly different levels of potency. For example, it is known in the art that ester and amide groups can react in vivo to form carboxylic acids. It is known that guanidine groups (such as the guanidine group of creatine) can undergo phosphorylation in vivo.

The creatine derivatives may be cationic as a consequence of the mitochondrial targeting agent. For example, in some embodiments, a creatine compound contains a mitochondrial targeting agent which includes a cationic phosphonium group (e.g., a phosphorous atom substituted by four carbon groups). In cases where a quaternary cationic atom is an intrinsic component of the modified creatine compound, a complementary anionic counter-ion will be present. In some cases, the anionic counter-ion is also an intrinsic component of the modified creatine compound (i.e., the compound is an inner salt). For example, the creatine derivatives can also include a charged carboxylate or phosphate group. In some cases, a distinct ion species will serve as an anionic counter ion. In embodiments where a distinct anionic counter-ion is present, the anionic counter-ion can be a pharmaceutically acceptable anionic counter-ion chosen to confer desirable pharmaceutical properties, such as solubility, upon the modified creatine compound. In certain such embodiments, the anionic counter-ion is a chloride anion.

In some embodiments, the creatine derivatives include a guanidine moiety. The guanidine moiety is basic, and may be protonated by treatment with a pharmaceutically acceptable Bronstead acid.

In some embodiments, the creatine derivatives provided above may have one or more chiral centers and thus exist as one or more stereoisomers. Such stereoisomer-containing compounds can exist as a single enantiomer, a mixture of enantiomers, a mixture of diastereomers, or a racemic mixture.

Other exemplary creatine derivatives that can be modified to include a mitochondrial targeting agent include, but are not limited to, cyclocreatine (1-carboxymethyl-2-iminoimidazolidine), N-phosphorocreatine (N-phosphoryl creatine), cyclocreatine phosphate (3-phosphoryl-1-carboxymethyl-2-iminoimidazolidine), 1-carboxymethyl-2-aminoimidazole, 1-carboxymethyl-2,2-iminomethylimidazolidine, 1-carboxyethyl-2-iminoimidazolidine, N-ethyl-N-amidinoglycine, and beta-guanidinopropionic acid.

Functionalized creatine compounds contain a creatine subunit connected to or associated with one or more agents. Generally, creatine compounds are functionalized with a single agent. Alternatively, creatine compounds can be functionalized with more than one agent. For example, a creatine compound can bound to a linker, optionally containing one or more branch points, to which multiple agents are attached.

In the case of creatine compounds containing a plurality of agents, the agents may be the same or different. In some implementations, a creatine compound is functionalized with multiple copies of the same agent. In alternative implementations, a creatine compound is functionalized with a plurality of agents which share the same function (i.e., multiple mitochondrial targeting agents or multiple therapeutic agents). In certain implementations, a creatine compound is functionalized with a plurality of agents which have at least two different functions (i.e., a plurality of agents which contains one or more targeting agents, for example mitochondrial targeting agents, and one or more therapeutic agents).

The agent may be any substance which is physiologically or pharmacologically active in vivo or in vitro. The agent can be, for example, a substance used for treatment (e.g., therapeutic agent), prevention (e.g., prophylactic agent), diagnosis (e.g., diagnostic agent), cure, or mitigation of disease or illness, a substance which affects the structure or function of the body, a pro-drug which becomes biologically active or increasingly biologically active after it has been placed in a predetermined physiological environment, or a targeting agent. Examples include, but are not limited to, organic small molecules, peptides, proteins, antibodies, sugars, polysaccharides, and combinations thereof.

In some embodiments, the creatine compounds are functionalized with one or more mitochondrial targeting agents. Mitochondrial targeting agents are known in the art, and include lipophilic cations that convey a positive charge to the compound under physiological conditions, such as cationic phosphonium and ammonium groups.

In the case of cationic phosphonium and ammonium groups, the selection of carbon substituents on the cationic atom will affect the target activity, the ability of the therapeutic drug to localize within the mitochondria, and the pharmacokinetic properties (ADME) of the drug. Generally, the substituents on the cation are chosen to distribute the localization of the positive charge and to provide a lipophilic environment in the vicinity of the positive charge to shield the cation from direct interaction with lipophilic biological barriers. Additional pharmacokinetic properties, including oral bioavailability, volume of distribution, and clearance are also dependent on the balance between lipophilic and hydrophilic attributes. Specifically in this invention, the chemical features of the linker group D have been utilized to modify that balance.

In some implementations, the mitochondrial targeting agent can also be tetraphenylarsonium, Rhodamine G and derivatives thereof, oligo- or polyarginine, oligo- or polylysine, as well as delocalized lipophilic cations containing one to three carbimino, sulfimino, or phosphinimino units as described in Kolomeitsev et al., *Tet. Lett*., Vol. 44, No. 33, 5795-5798 (2003).

Liphophilic cations are examples of mitochondrial targeting agents because they can pass directly through phospholipid bilayers without requiring a specific uptake mechanism, and they accumulate substantially within mitochondria due to the large membrane potential. The large hydrophobic radius of the triphenylphosphine (TPP) cation enables it to pass easily through the phospholipid bilayer relative to other cations. In one embodiment, the disclosed compounds include TPP derivatives modified to increase hydrophobicity. For example, the hydrophobicity of the targeting agent can be increased by increasing the length of the carbon chain linker, as described in Asin-Cayuela et al., *FEBS Lett.,* 30:571 (1-3), 9-16 (2004).

In some embodiments, the mitochondrial targeting agent can also be a polypeptide, such as a positively charged amino acid. Protein transduction domains (PTD), also known as a cell penetrating peptides (CPP), are polypeptides including positively charged amino acids. Therefore, the mitochondrial targeting agent can be a PTD or a CPP. "Protein Transduction Domain" refers to a polypeptide, polynucleotide, carbohydrate, or organic or inorganic compound that facilitates traversing a lipid bilayer, micelle, cell membrane, organelle membrane, or vesicle membrane. A PTD attached to the compounds disclosed herein facilitates the molecule traversing membranes, for example, going from extracellular space to intracellular space, or cytosol to within an organelle such as the mitochondria. PTDs are known in the art, and include, but are not limited to, small regions of proteins that are able to cross a cell membrane in a receptor-independent mechanism (Kabouridis, P., *Trends in Biotechnology* (11):498-503 (2003)). Although several PTDs have been documented, the two most commonly employed PTDs are derived from TAT protein of HIV (Frankel and Pabo, *Cell,* 55(6):1189-93(1988)) and Antennapedia transcription factor from *Drosophila*, whose PTD is known as Penetratin (Derossi et al., *J Biol Chem.,* 269(14): 10444-50 (1994)).

In other embodiments, mitochondrial targeting agents can include short peptide sequences (Yousif, et al., *Chembiochem.,* 10(13):2131 (2009)), for example mitochondrial transporters-synthetic cell-permeable peptides, also known as mitochondria-penetrating peptides (MPPs), that are able to enter mitochondria. MPPs are typically cationic, but also lipophilic; this combination of characteristics facilitates permeation of the hydrophobic mitochondrial membrane. For example, MPPs can include alternating cationic and hydrophobic residues (Horton, et al., *Chem Biol.,* 15(4):375-82 (2008)). Some MPPs include delocalized lipophilic cations (DLCs) in the peptide sequence instead of, or in addition to natural cationic amino acids (Kelley, et al., *Pharm. Res.,* 2011 Aug. 11 [Epub ahead of print]). Other variants can be based on an oligomeric carbohydrate scaffold, for example attaching guanidinium moieties due to their delocalized cationic form (Yousif, et al., *Chembiochem.,* 10(13):2131 (2009).

In other embodiments, mitochondrial targeting agents also include mitochondrial localization signals or mitochondrial targeting signals. Many mitochondrial proteins are synthesized as cytosolic precursor proteins containing a leader sequence, also known as a presequence, or peptide signal sequence. Typically, cytosolic chaperones deliver the precursor protein to mitochondrial receptors and the General Import Pore (GIP) (Receptors and GIP are collectively known as Translocase of Outer Membrane or TOM) at the outer membrane. Typically, the precursor protein is translocated through TOM, and the intermembrane space by small TIMs to the TIM23 or 22 (Translocase of Inner Membrane) at the inner membrane. Within the mitochondrial matrix the targeting sequence is cleaved off by mtHsp70.

Mitochondrial localization/targeting signals generally have of a leader sequence of highly positively charged amino acids. This allows the protein to be targeted to the highly negatively charged mitochondria. Unlike receptor: ligand approaches that rely upon stochastic Brownian motion for the ligand to approach the receptor, the mitochondrial localization signal of some embodiments is drawn to mitochondria because of charge.

As discussed above, in order to enter the mitochondria, a protein generally must interact with the mitochondrial import machinery, consisting of the TIM and TOM complexes (Translocase of the Inner/Outer Mitochondrial Membrane). With regard to the mitochondrial targeting signal, the positive charge draws the linked protein to the complexes and continues to draw the protein into the mitochondria. The Tim and Tom complexes allow the proteins to cross the membranes. Accordingly, one embodiment of the present disclosure delivers compositions of the present disclosure to the inner mitochondrial space utilizing a positively charged targeting signal and the mitochondrial import machinery. In another embodiment, PTD-linked compounds containing a mitochondrial localization signal do not seem to utilize the TOM/TIM complex for entry into the mitochondrial matrix, see Del Gaizo et al. *Mol Genet Metab.* 80(1-2):170-80 (2003). Mitochondrial localization signals are known in the art, see for example, U.S. Published Application No. 2005/0147993.

In some other embodiments, other mitochondrial targeting agents include compounds that are actively transported into the mitochondria, bind to a mitochondria-specific protein, and/or show preferential affinity to a mitochondria-specific lipid such as phospholipid CL. For example, the mitochondrial targeting agent can be a membrane-active cyclopeptide antibiotic, such as gramicidin S, or a segment thereof. Antibiotics of this type have a high affinity for bacterial membranes. Therefore, because of the close relationship between bacteria and mitochondrial membranes, membrane-active cyclopeptide antibiotics, or a segment thereof, also have a high affinity for mitochondrial membrane, and can be used to preferentially target cargo to the mitochondria (Fink, et al., *Crit. Care. Med.,* 35(Suppl): 5461-7 (2007).

Other suitable mitochondrial targeting agents are known in the art, see for example, Frantz and Wipf, *Environ Mol Mutagen.,* 51(5): 462-475 (2010), (Yousif, et al., *Chembiochem.,* 10(13):2131 (2009), and Galley, *Crit Care,* 14(4):230 (pages 1-9) (2010). Particularly, the mitochondrial targeting agent does not permanently damage the mitochondrion, for example the mitochondrial membrane, or otherwise impair mitochondrial function.

In some embodiments, creatine derivatives may optionally contain a linker which connects the creatine subunit to the agent. The linker can be inert, or the linker can have biological activity. The linker must be at minimum bivalent; however, in some embodiments, the linker can be bound to more than one active agent, in which case, the linker is polyvalent.

In many cases, the linker is a linear chain. In some embodiments, however, the linker contains one or more branch points. In the case of a branched linker, the terminus of each branch point can be functionalized with an agent. In one such embodiment, a dendritic linker is used, with the creatine subunit being bound to the focal point of the dendrimer, and multiple agents are bound to the ends of the dendritic branches.

In some embodiments, the linker includes one or more cleavable subunits, such as a disulfide group, a hydrazone group, or a peptide group, which can be cleaved by proteolytic enzymes within a cell. In alternative embodiments, the linker contains one or more hydrolysable subunits, such as an ester group. The linker can also contain one or more covalent or non-covalent functional groups to facilitate the assembly and/or separation of the creatine subunit from the attached agent, including, but not limited to, one or more metal complexes, such as polyhistidine-nickel chelate complexes, one or more heteroaromatic rings (such as triazole rings formed by the cycloaddition of an alkyne and an azide), one or more hydrogen bond donor-acceptor pairs, and one or more biomolecule/bioconjugate pairs (such as biotin-avidin or biotin-streptavidin pair), as well as combinations thereof.

Creatine derivatives contain a functional group which serves to confer creatine-like activity and/or to serve as an attachment point for the linker group. In cases where this serves as an attachment point for the linker group may result in an intrinsically active compound or may serve as a pro-drug.

In some embodiments, the functional group contains one or more heteroatoms selected from the group consisting of oxygen, nitrogen, sulfur, phosphorous, and combinations thereof. Representative functional groups include esters, ethers, ketones, amides, ureas, carbamates, thioesters, thioethers, disulfide bonds, thioamides, thiones, thionoesters, triazole rings, and dithioesters. In some embodiments, the functional group is a secondary amide, tertiary amide, or ester.

The term "reduce", "inhibit", "alleviate" or "decrease" are used relative to a control. One of skill in the art would readily identify the appropriate control to use for each experiment. For example a decreased response in a subject or cell treated with a compound is compared to a response in subject or cell that is not treated with the compound.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein the term "isolated" is meant to describe a compound of interest (e.g., nucleic acids, polypeptides, etc.) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids or polypeptides are at least 60% free, preferably 75% free, and most preferably 90% free from other associated components.

"Localization Signal or Sequence or Domain" or "Targeting Signal or Sequence or Domain" are used interchangeably and refer to a signal that directs a molecule to a specific cell, tissue, organelle, intracellular region or cell state. The signal can be polynucleotide, polypeptide, or carbohydrate moiety or can be an organic or inorganic compound sufficient to direct an attached molecule to a desired location. Exemplary targeting signals include mitochondrial localization signals from the precursor proteins list in U.S. Pat. No. 8,039,587, and cell targeting signals known in the art such as those in Wagner et al., *Adv Gen,* 53:333-354 (2005), the disclosures of which are specifically incorporated by reference herein in their entirety. It will be appreciated that the entire sequence need not be included, and modifications including truncations of these sequences are within the scope of the disclosure provided the sequences operate to direct a linked molecule to a specific cell type. Targeting signals of the present disclosure can have 80 to 100% sequence identity to the mitochondrial localization signal or cell targeting signal sequences. One class of suitable targeting signals include those that do not interact with the targeted cell in a receptor:ligand mechanism. For example, targeting signals include signals having or conferring a net charge, for example a positive charge. Positively charged signals can be used to target negatively charged cell types such as neurons and muscle. Negatively charged signals can be used to target positively charged cells.

"Tropism" refers to the propensity of a molecule to be attracted to a specific cell, cell type or cell state. In the art, tropism can refer to the way in which different viruses and pathogens have evolved to preferentially target to specific host species, or specific cell types within those species. The propensity for a molecule to be attracted to a specific cell, cell type or cell state can be accomplished by means of a targeting signal.

"Cell type" is a manner of grouping or classifying cells in the art. The term cell type refers to the grouping of cells based on their biological character determined in part through common biological function, location, morphology, structure, expression of polypeptides, nucleotides or metabolites.

"Cell state" refers to the condition of a cell type. Cells are dynamic throughout their life and can achieve various states of differentiation, function, morphology and structure. As used herein, cell state refers to a specific cell type throughout its lifetime.

"Cell surface marker" refers to any molecule such as moiety, peptide, protein, carbohydrate, nucleic acid, antibody, antigen, and/or metabolite presented on the surface or in the vicinity of a cell sufficient to identify the cell as unique in either type or state.

The term "combination" or "co-administration" refers to administering the compositions disclosed herein in conjenciton with another therapeutic agent to patients with the disease or condition being treated.

II. Methods of Treatment

The disclosed compositions can be used to treat one or more symptoms of Cerebral Creatine Deficiency Syndromes, including Guanidinoaceteate Methyltransferase Deficiency (GAMT Deficiency), L-Arginine: Glycine Amidinotransferase Deficiency (AGAT Deficiency), and SLC6A8-Related Creatine Transporter Deficiency (SLC6A8 Deficiency).

The disclosed compositions can be used to modulate ATP production in mitochondria by altering the ratio of phosphocreatine/creatine. The ratio of phosphocreatine/creatine can be increased relative to a control by administering one or more of the disclosed compounds. Increasing the amount of phosphocreatine in the mitochondria increases the ability of the mitochondria to produce ATP. Thus, another embodiment provides a method for increasing mitochondrial production of ATP in a host by administering to the host an effective amount of the disclosed compositions. Increasing the ATP-generating capacity allows a cell to better handle energetic challenges, thus preventing cell damage or death, improving cellular function, increasing cellular healing and replacement, and preventing tumorigenesis.

One embodiment provides a nutraceutical, including one or more of the disclosed mitochondria-targeted compounds. The nutraceucitcal can be used, for example by performance athletes, for endurance training, muscle/strength building, bone density increase, cognitive function, wound healing, anti-aging, anti-obesity/weight loss, and anti-ROS. The nutraceutical can be administered to healthy or diseased individuals.

Increasing mitochondrial production of ATP can be useful for improving exercise tolerance or stamina and/or muscle strength or stamina. For example, the compositions disclosed herein can be administered to a subject to enhance the ability to sustain high ATP turnover rates during strenuous exercise resulting in delayed neuromuscular fatigue, improved muscle strength, improved muscle power output, improved recovery from exercise, increased body mass and increased muscle mass, or combinations thereof, compared to a control. In some embodiments, the compositions are administered to inhibit or reduce the effects of sarcopenia, the typical loss of muscle mass that is characteristic of advanced age. For example, the compositions may attenuate age-related muscle atrophy and/or strength loss in a subject compared to a control.

The compositions disclosed herein can also be administered to a subject to improve or increase brain or cognitive performance. Brain/cognative performance includes, but is not limited to, beneficial effects on mental functions, such as an increase in response to mental training or challenge, reduced mental fatigue, improved task-evoked increase in oxygen utilization, improved recognition memory, increased speed of computation, increased power of computation, and improved general ability (Rae, et al., *Proc. R. Soc. Lond.* 270:2147-2150 (2007)). Extracellular ATP increase may also enhance cerebral blood flow and metabolism, increase mental sharpness, and potentially lessen the perception of fatigue and/or exercise-associated pain in the subject.

The compositions disclosed herein can also be administered to a subject to alleviate unwanted side effects (as described above) of a medical treatment on human skin. The medical treatment comprises administering an effective amount of a corticosteroid, or an effective amount of a non-steroidal drug that binds to the glucocorticosteroidal receptor.

In one embodiment, the compositions disclosed herein include a compound of Formulae I-IV. In another embodiment, the compositions disclosed herein include a compound described in Table 1 or Table 2. In another embodiment, the compositions disclosed herein include Mitorcreatine.

In another embodiment, the compositions disclosed herein include a recombinant polypeptide comprising a protein transduction domain, a mitochondrial localization signal, and a mature transcription factor A-mitochondrial (TFAM).

In another embodiment, the compositions disclosed herein include a compound of Formula IV. In another embodiment, the compositions disclosed herein include compounds B-1A and B-5A.

The compositions disclosed herein can also be administered to a subject to increase endurance and strength in an individual in need thereof, the method comprising administering a composition to a patient, wherein said composition comprises an effective amount of a compound described in Formulae I-IV or a recombinant polypeptide comprising a protein transduction domain, a mitochondrial localization signal, and a mature transcription factor A-mitochondrial (TFAM). Specifically, the compound described in Table 1 includes Mitocreatine. Specifically, the compounds of Formula IV include compounds B-1A and B-5A. These compounds are as efficacious as or more efficacious than creatine and may be used at lower dosage, for example, at one tenth (1/10th), one twentieth (1/20th) or one thirtieth (1/30th) of the dosing amount utilized for creatine treatment. The compounds may be administered in an amount from about 0.4 mg/kg to about 5 mg/kg bodyweight in human. More specifically, the compounds may be administered in an amount at about 0.8 mg/kg, at about 1.6 mg/kg, or at about 2.4 mg/kg in a human.

The compositions disclosed herein can also be administered to a subject to treat or prevent a patient experiencing skin conditions, or for improving the mitochondrial activities and enhancing the collagen expression in the skin of a patient.

Specifically, the skin conditions include wrinkles, sun damaged skin, skin rash, acne, symptoms of aged skin, unwanted side effects of medical treatments of human skin, or risk of contracting melanoma. Specifically, the symptom of aging is induced by the sun (also known as sun damaged skin).

The compositions disclosed herein can also be administered to a subject to increase mitochondrial activity in the dermis or epidermis, or both.

The compositions disclosed herein can also be administered to a subject to treat or prevent the symptoms of aging. These symptoms of aging could be caused by susceptibility to solar radiation or increase in cellular senescence or loss of elasticity or loss of tensile strength or fragile or thin skin or reduced epidermal hydration.

The compositions disclosed herein can also be administered to a subject to delay the symptoms of aging caused by impaired collagen remodeling or reduced epidermal hydration.

The compositions disclosed herein can also be administered to a subject to alleviate the side effects caused by a cancer therapy on human skin. The cancer therapy comprises the use of EGFR inhibitor or a chemotherapeutic agent. In some embodiments, the EGFR inhibitor is cetuximab. In some other embodiments, the chemotherapeutic agent is Gemcitabine or Temozolomide.

The compositions disclosed herein can be administered to a subject to alleviate unwanted side effects caused by administering corticosteroid or non-steroidal drug that binds to the glucocorticosteroidal receptor on human skin. In some embodiments, the unwanted side effects comprise skin atrophy, thin skin, fragile skin, telangiectasia or striae. In some embodiments, the unwanted side effects are a rash or acne form blistering.

The compositions disclosed herein can also be administered to a subject to alleviate unwanted side effects of medical treatments of human skin comprising co-administering corticosteroid or a non-steroidal drug to patient in need thereof. In one embodiment, the corticosteroid comprises Dexamethasone, Betamethasone or Clobetasol.

In some embodiments, the composition is administered systemically or topically to the skin.

In some embodiments, the composition and the corticosteroid or the non-steroidal drug are optionally administered concurrently.

In some embodiments, the composition and the corticosteroid or the non-steroidal drug are formulated in one formulation.

In some embodiments, the composition disclosed herein comprises an effective amount of a corticosteroid or a non-steroidal drug and an effective amount of a compound of Formulae I-IV to reduce skin atrophy of the patient.

In one embodiment, a compound of Formula I is Mitocreatine, and the corticosteroid is selected from Dexamethasone, Betamethasone or Clobetasol, wherein the composition is formulated to be applied directly to the skin.

In one embodiment, Mitocreatine is present in an amount from about 0.01% w/v to about 3% w/v.

In some embodiments, the composition is in a form of lotion, cream, ointment, gel, aerosol, foam, spray, paste, powder or solid.

The compositions disclosed herein can also be administered to a subject to treat or prevent age related macular degeneration in a patient in need thereof.

The compositions disclosed herein can also be administered to a subject to enhance collagen expression in the elderly population, or to reduce wrinkles, or to strengthen fragile skin, or to increase thickness of thin skin.

In some embodiments, the compositions disclosed herein are administered in conjunction with another therapeutic agent. The other therapeutic agent may be also a creatine derivative, or may operate by a different mechanism. In some embodiments, a compound of Formula (I) may be administered in conjunction with a rhTFAM. In other embodiments, a compound of Formula (IV) may be administered in conjunction with a rTFAM. The term "combination" or "co-administration" refers to administering the compositions in conjenciton with another therapeutic agent. The term "combination" or "co-administration" refers to the compositions may be administered with the other therapeutic agents in a single dosage form or as a separate dosage form. When administered as a separate dosage form, the other therapeutic agents may be administered prior to, at the same time as, or following administration of the compositions disclosed herein.

III. Formulations and Dosages

Formulations containing one or more of the compounds described herein or a prodrug thereof may be prepared using a pharmaceutically acceptable carrier composed of materials that are considered safe and effective and may be administered to an individual without causing undesirable biological side effects or unwanted interactions. The carrier comprises all components present in the pharmaceutical formulation other than the active ingredient or ingredients. As generally used herein, "carrier" includes, but is not limited to, diluents, binders, lubricants, disintegrators, fillers, pH modifying agents, preservatives, antioxidants, solubility enhancers, and coating compositions.

The carrier also includes all components of the coating composition, which may include plasticizers, pigments, colorants, stabilizing agents, and glidants. Delayed release, extended release, and/or pulsatile release dosage formulations may be prepared as described in standard references, such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers, such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers, such as plasticizers, pigments, colorants, glidants, stabilization agents, pore formers, and surfactants.

Optional pharmaceutically acceptable excipients present in the drug-containing tablets, beads, granules, or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration and generally include, but are not limited to, starch, sodium starch glycolate, sodium carboxymethyl starch, sodium carboxymethylcellulose, hydroxypropyl cellulose, pregelatinized starch, clays, cellulose, alginine, gums, and cross linked polymers, such as cross-linked PVP (Polyplasdone XL from GAF Chemical Corp).

Stabilizers are used to inhibit or retard drug decomposition reactions, which include, by way of example, oxidative reactions.

Surfactants may be anionic, cationic, amphoteric or nonionic surface active agents. Suitable anionic surfactants include, but are not limited to, those containing carboxylate, sulfonate, and sulfate ions. Examples of anionic surfactants include sodium, potassium, ammonium of long chain alkyl sulfonates, and alkyl aryl sulfonates, such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds, such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine, and lauryl sulfobetaine.

If desired, the tablets, beads, granules, or particles may also contain minor amount of nontoxic auxiliary substances, such as wetting or emulsifying agents, dyes, pH buffering agents, or preservatives.

The compositions optionally contain one or more additional active agents. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

Representative antibiotics include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin.

In one embodiment, the concentration of the antibiotic is from about 0.01% to about 20%, particularly from about 1% to about 15%, more particularly from about 6% to about 12%, by weight of the final composition.

Representative examples of non-steroidal anti-inflammatory agents include, without limitation, oxicams, such as piroxicam, isoxicam, tenoxicam, and sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

In one embodiment, the concentration of the non-steroidal anti-inflammatory agent is from about 0.01% to about 20%, particularly from about 1% to about 15%, more particularly from about 6% to about 12% by weight of the final composition.

Representative examples of steroidal anti-inflammatory drugs include, without limitation, corticosteroids, such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

In one embodiment, the concentration of the steroidal anti-inflammatory agent is from about 0.01% to about 20%, particularly from about 1% to about 15%, more particularly from about 6% to about 12%, by weight of the final composition.

Suitable antimicrobial agents include, but are not limited to, antibacterial, antifungal, antiprotozoal and antiviral agents, such as β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, famesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

In one embodiment, the concentration of the anti-microbial agent is from about 0.01% to about 20%, particularly from about 1% to about 15%, more particularly from about 6% to about 12%, by weight of the final composition.

For all of the creatine compounds disclosed, as further studies are conducted, information will emerge regarding appropriate dosage levels for treatment of various conditions in various patients, and the ordinary skilled person, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage levels may be lower.

Pharmaceutical compositions including the disclosed compounds are provided. The pharmaceutical compositions may be for administration by oral, parenteral (intramuscular, intraperitoneal, intravenous (IV), or subcutaneous injection), transdermal (either passively or using iontophoresis or electroporation), or transmucosal (nasal, vaginal, rectal, or sublingual) routes of administration or by using bioerodible inserts, and can be formulated in dosage forms appropriate for each route of administration. In one embodiment, the compounds are administered orally. In another embodiment, the compounds are administered parenterally in an aqueous solution. In general, pharmaceutical compositions are provided including effective amounts of a creatine compounds or analogs.

In some embodiments, the composition described herein is used for increasing endurance and strength, wherein the use comprises administering an effective amount of a compound of Formulae I-IV to a patient. The effective amount of a compound is from about 1.5 mg/kg to about 9 mg/kg body weight in human. Specifically, the effective amount of a compound is about 1.5 mg/kg body weight in human. More specifically, the effective amount of a compound is about 4 mg/kg body weight in human. Most specifically, the effective amount of a compound is about 8 mg/kg body weight in human.

In some embodiments, the compositions described herein are used for treating or preventing age related macular degeneration or for increasing the mitochondrial activity of the eye in a patient in need thereof, wherein the use comprises administering a composition to a patient, wherein the compound is administered through intravitreal injection or topically applied to the eyes in a patient in need thereof.

The compositions may be formulated for oral delivery. Oral solid dosage forms are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapy is given by Marshall, K. In: Modern Pharmaceutics Edited by G. S. Banker and C. T. Rhodes Chapter 10, 1979, herein incorporated by reference. In general, the formulation will include the ABC transporter ligands (or chemically modified forms thereof) and inert ingredients which allow for protection against the stomach environment and release of the biologically active material in the intestine.

Other embodiment provides liquid dosage forms for oral administration, including pharmaceutically acceptable emulsions, solutions, suspensions, and syrups, which may contain other components, including inert diluents; adjuvants such as wetting, emulsifying, and suspending agents; and sweetening, flavoring, and perfuming agents.

The compositions may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is an example of chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane, and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Particularly, the release will avoid the deleterious effects of the stomach environment, either by protection of the peptide (or derivative) or by release of the peptide (or derivative) beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings or coatings which make the tablet easier to swallow. Capsules may consist of a hard shell (such as gelatin) for delivery of dry therapeutic (i.e., powder). For liquid forms, a soft gelatin shell may be used. The shell material of cachets could be thick starch or other edible paper. For pills, lozenges, molded tablets or tablet triturates, moist massing techniques can be used.

The active ingredient (or derivative) can be included in the formulation as fine multiparticulates in the form of granules or pellets of particle size about 1 mm. The formulation of the material for capsule administration could also be as a powder, lightly compressed plugs, or as tablets. These therapeutics could be prepared by compression.

Colorants and/or flavoring agents may also be included. For example, the composition may be formulated, such as by liposome or microsphere encapsulation, and then further contained within an edible product, such as a refrigerated beverage containing colorants and flavoring agents.

Preparations disclosed here for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are particularly suppositories which may contain, in addition to the active substance, excipients such as cocoa butter or a suppository wax. Compositions for nasal or sublingual administration are also prepared with standard excipients well known in the art.

IV. Compositions

Suitable compositions for use with the disclosed methods include creatine derivatives of Formula I

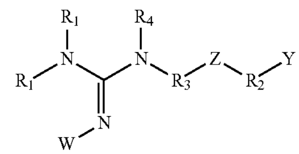

I or a pharmaceutically acceptable salt thereof wherein Z is —C(═O)$NR_5$—, —OC(═O)$NR_5$—, —$NR_7$C(═O)O—, —$NR_5$C(═O)$NR_5$—, —$SO_2NR_5$—, —$NR_5SO_2$—, —O—, —S—, —S—S—, —$CR_5$OH—, or —$CR_5$SH—; wherein each $R_5$ is independently hydrogen, alkyl, aryl, or heterocyclic; Y is a cationic phosphonium group, or a polypeptide containing at least one positively charged amino acid residue; each $R_1$ is independently hydrogen, or a phosphate group; $R_2$ is absent, alkyl, cycloalkyl, heterocycloalkyl, alkylaryl, alkylarylalkyl, or aryl; $R_3$ is alkyl, cycloalkyl, alkylcycloalkyl, heterocycloalkyl, alkylheterocycloalkyl, alkylaryl, or alkylarylalkyl; $R_4$ is hydrogen, alkyl, or aryl; or $R_4$ and a $R_1$ group together with the nitrogen atoms to which they are attached form a heterocyclic ring containing at least five atoms; or $R_4$ and $R_3$ together with the nitrogen atom to which they are attached form a heterocyclic ring containing at least five atoms; at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl; or at each occurrence, an aryl is optionally substituted with 1-5 substituents independently selected from halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and CN; and W is hydrogen or alkyl.

Specifically, the present invention provides a compound of Formula I wherein Z is —C(═O)$NR_5$—, —OC(═O)$NR_5$—, —$NR_7$C(═O)O—, or —$NR_5$C(═O)$NR_5$—; wherein each $R_5$ is independently hydrogen, or $C_{1-6}$alkyl; Y is a cationic phosphonium group; each R1 is independently hydrogen, or a phosphate group; $R_2$ is alkyl, cycloalkyl, heterocycloalkyl, or alkylaryl; $R_3$ is alkyl, cycloalkyl, alkylcycloalkyl, heterocycloalkyl, alkylheterocycloalkyl, or alkylaryl; $R_4$ is hydrogen, or $C_{1-6}$alkyl; and W is hydrogen.

Specifically, the present invention provides a compound of formula I wherein Z is —C(═O)$NR_5$—, wherein $R_5$ is hydrogen, or $C_{1-6}$alkyl; Y is —$P^+(R')_3X^-$, wherein R' is alkyl or aryl; and $X^-$ is an anion; each $R_1$ is independently hydrogen, or —$PO_3^{2-}$ M, wherein M is a pharmaceutically acceptable cation having one or two positive charges such as $M^+$, or $M^{2+}$; $R_2$ is straight or branched $C_{1-8}$alkyl; $R_3$ is alkyl, cycloalkyl, alkylcycloalkyl, heterocycloalkyl, or alkylheterocycloalkyl, wherein alkyl is straight or branched $C_{1-12}$alkyl, cycloalkyl comprises 3-8 carbon atoms, heterocycloalkyl is a cyclic ring of 5-10 atoms having at least one hetero atom selected from sulfur, non-peroxide oxygen, or nitrogen; $R_4$ is hydrogen or $C_{1-4}$alkyl; and W is hydrogen.

Specifically, the present invention provides a compound of Formula I wherein Z is —C(═O)NH, Y is —$P^+(Phenyl)_3X^-$, wherein $X^-$ is chloride, or trifluoroacetate; $R_1$ is hydrogen; $R_2$ is $C_{1-8}$alkyl; $R_3$ is $C_{1-6}$alkyl, $C_{1-6}$alkylcycloalkyl wherein cycloalkyl comprising 3-6 carbon atoms, or $C_{1-6}$alkylheterocycloalkyl wherein heterocycloalkyl is a cyclic ring of 5-6 atoms having a nitrogen atom; and $R_4$ is methyl.

Specifically, a compound of Formula I wherein Z is —C(═O)$NR_5$—, and $R_5$ is hydrogen, or $C_{1-6}$alkyl.

Specifically, a compound of Formula I wherein Z is —C(═O)NH.

Specifically, a compound of Formula I wherein a cationic phosphonium group is selected from —$P^+(R')_3X^-$, wherein R' is alkyl or aryl; and $X^-$ is an anion.

Specifically, a compound of Formula I wherein R' is phenyl; and $X^-$ is chloride, or trifluoroacetate.

Specifically, a compound of Formula I wherein at least one $R_1$ is hydrogen.

Specifically, a compound of Formula I wherein one $R_1$ is hydrogen, the other $R_1$ is —$PO_3^{2-}$ M.

Specifically, a compound of Formula I wherein $R_2$ is straight or branched $C_{1-20}$alkyl.

Specifically, a compound of Formula I wherein $R_2$ is $C_{3-8}$alkyl.

Specifically, a compound of Formula I wherein $R_3$ is alkyl, cycloalkyl, alkylcycloalkyl, heterocycloalkyl, or alkylheterocycloalkyl, wherein alkyl is straight or branched.

Specifically, a compound of Formula I wherein $R_3$ is $C_{1-8}$alkyl.

Specifically, a compound of Formula I wherein $R_3$ is $C_{1-6}$alkyl.

Specifically, a compound of Formula I wherein $R_3$ is $C_{1-6}$alkylcycloalkyl wherein cycloalkyl comprises 3-8 carbon atoms.

Specifically, a compound of Formula I wherein $R_3$ is $C_{1-6}$alkylcycloalkyl wherein cycloalkyl comprising 3-6 carbon atoms.

Specifically, a compound of Formula I wherein $R_3$ is $C_{1-6}$alkylheterocycloalkyl wherein heterocycloalkyl is a cyclic ring of 3-10 atoms having at least one hetero atom selected from sulfur, non-peroxide oxygen, or nitrogen.

Specifically, a compound of Formula I wherein $R_3$ is $C_{1-6}$alkylheterocycloalkyl wherein heterocycloalkyl is a cyclic ring of 5-6 atoms.

Specifically, a compound of Formula I wherein $R_4$ is hydrogen or $C_{1-4}$alkyl.

Specifically, a compound of Formula I wherein $R_4$ is methyl.

Other suitable compositions for use with the disclosed methods include, the creatine derivative of Formula IX which is a pharmaceutically acceptable salt of Formula I

IX

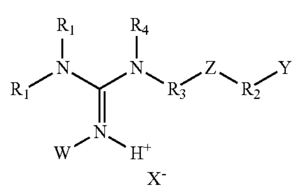

wherein $X^-$ is an anion.

Other suitable compositions for use with the disclosed methods include the creatine derivative of Formula II or III

II

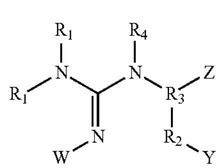

-continued

III

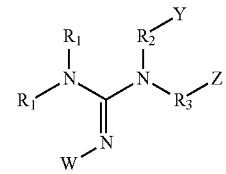

or a pharmaceutically acceptable salt thereof wherein Z is a functional group such as —C(═O)$NR_5R_5$, —$NR_5$C(═O)$OR_5$, —$NR_5$C(═O)$NR_5R_5$, —O(C═O)$NR_5R_5$, —$SO_2NR_5R_5$, —$NR_5SO_2R_5$, —$OR_5$, —$SR_5$, —S—$SR_5$, —$CR_5$OH, or —$CR_5$SH, with the proviso that Z and the guanidine nitrogen are not substituted on the same $R_3$ carbon when Z is —$NR_5$C(═O)$OR_5$, —$NR_5$C(═O)$NR_5R_5$, —O(C═O)$NR_5R_5$, —$SO_2NR_5R_5$, —$NR_5SO_2R_5$, —$OR_5$, —$SR_5$, or —S—$SR_5$; and wherein each $R_5$ is independently hydrogen, alkyl, aryl, or heterocyclic; Y is a mitochondrial targeting agent, a cationic ammonium group, or a polypeptide containing at least one positively charged amino acid residue; each $R_1$ is independently hydrogen, alkyl, or a phosphate group; $R_2$ is absent, or a linker selected from the list comprising alkyl, cycloalkyl, heterocycloalkyl, alkylaryl, alkylarylalkyl, or aryl, with the proviso that when Y is a cationic phosphonium group the guanidine nitrogen and Y are not substituted on the same $R_2$ carbon;

$R_3$ is a spacer group selected from the list comprising alkyl, cycloalkyl, alkylcycloalkyl, heterocycloalkyl, alkylheterocycloalkyl, alkylaryl, or alkylarylalkyl, with the proviso that Z and the guanidine nitrogen are not substituted on the same $R_3$ carbon; $R_4$ is hydrogen, alkyl, aryl, or heterocyclic; or $R_4$ and a $R_1$ group together with the nitrogen atoms to which they are attached form a heterocyclic ring containing at least five atoms; or $R_4$ and $R_3$ together with the nitrogen atom to which they are attached form a heterocyclic ring containing at least five atoms; at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl; at each occurrence, an aryl is optionally substituted with 1-5 substituents independently selected from halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and CN; and W is hydrogen or alkyl.

Specifically, a compound of Formula II or III wherein Z is —C(═O)$N(R_5)_2$, —C(═O)$N(R_5)_2$, —$NR_7$C(═O)O($R_5$), —$NR_5$C(═O)$N(R_5)_2$, —$SO_2N(R_5)_2$, —$NR_5SO_3$, —O($R_5$), —S($R_5$), —S—S($R_5$), —$C(R_5)_2$OH, or —$C(R_5)_2$SH—; wherein $R_5$ is hydrogen, alkyl, aryl, or heterocyclic; Y is a cationic phosphonium group, or a polypeptide containing at least one positively charged amino acid residue; $R_1$ is independently hydrogen, or a phosphate group; $R_2$ is absent, alkyl, cycloalkyl, heterocycloalkyl, alkylaryl, alkylarylalkyl, or aryl; $R_3$ is alkyl, cycloalkyl, alkylcycloalkyl, heterocycloalkyl, alkylheterocycloalkyl, alkylaryl, or alkylarylalkyl; $R_4$ is hydrogen, alkyl, or aryl; and W is hydrogen or alkyl.

Specifically, a compound of Formula II or III is wherein Z is —C(═O)$N(R_5)_2$, —C(═O)$N(R_5)_2$, —$NR_7$C(═O)O($R_5$), or —$NR_5$C(═O)$N(R_5)_2$, —$SO_2N(R_5)_2$, wherein each $R_5$ is independently hydrogen, or $C_{1-6}$alkyl; Y is a cationic phosphonium group; each $R_1$ is independently hydrogen, or a phosphate group; $R_2$ is alkyl, cycloalkyl, heterocycloalkyl, or alkylaryl; $R_3$ is alkyl, cycloalkyl, alkylcycloalkyl, heterocycloalkyl, alkylheterocycloalkyl, or alkylaryl; and $R_4$ is hydrogen, or $C_{1-6}$alkyl; and W is hydrogen.

Other suitable compositions for use with the disclosed methods include, a compound of Formula IIX or IIIX, suitable pharmaceutically acceptable salts of Formula II, or III

IIX

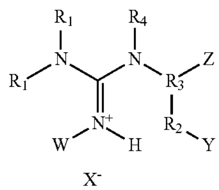

IIIX

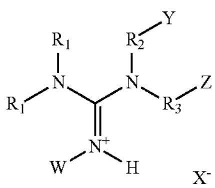

wherein $X^-$ is an anion.

Exemplary creatine derivatives include, but are not limited to:

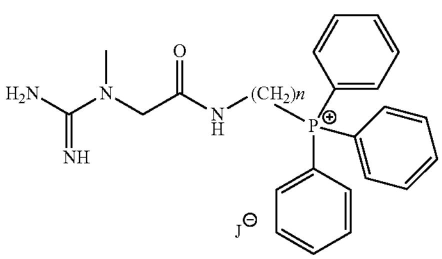

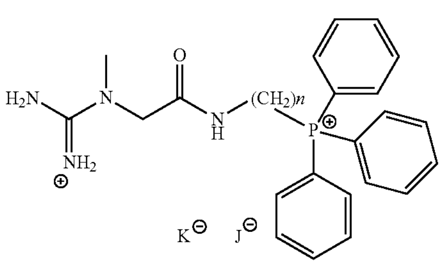

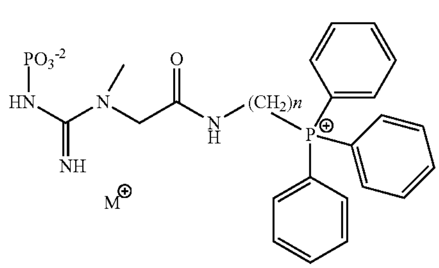

-continued

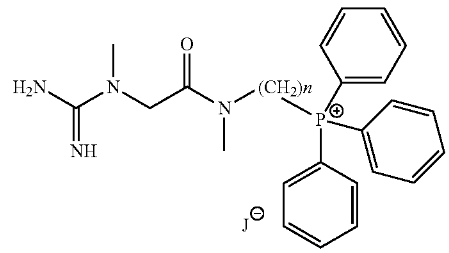

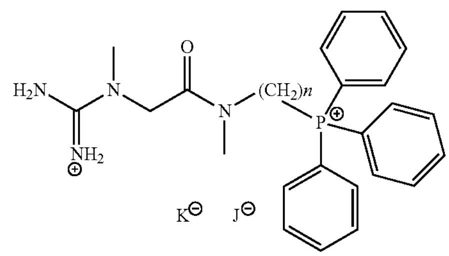

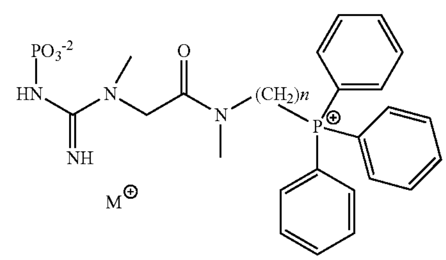

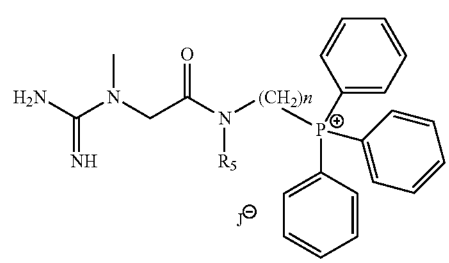

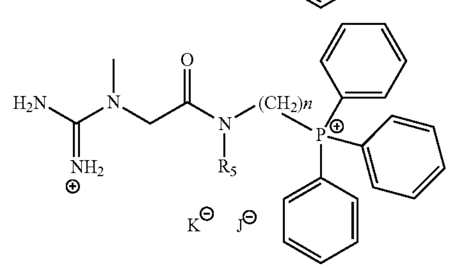

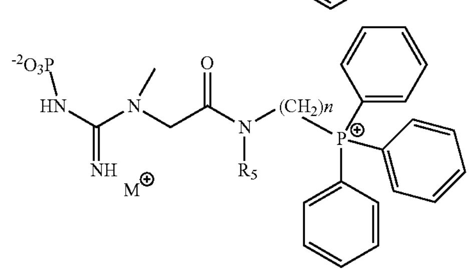

-continued
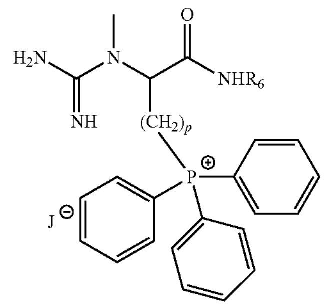
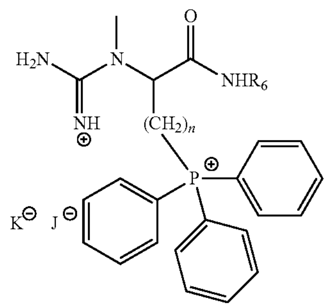
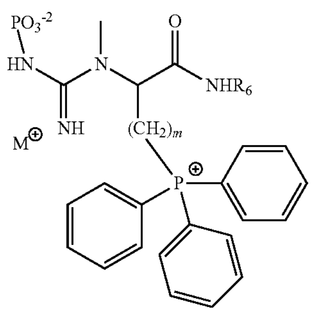
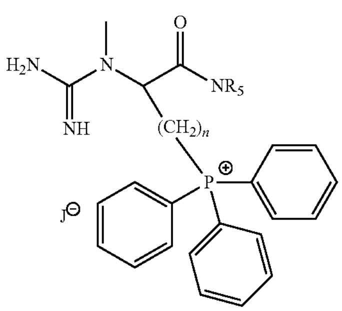
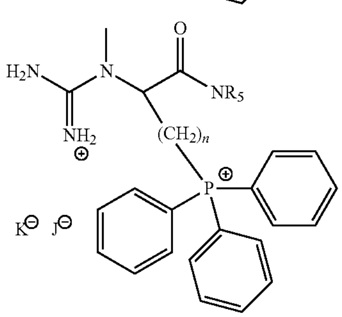
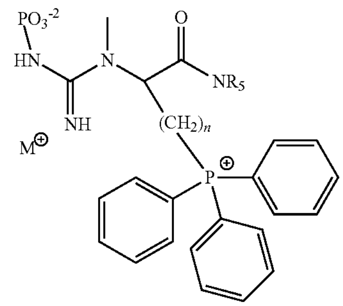
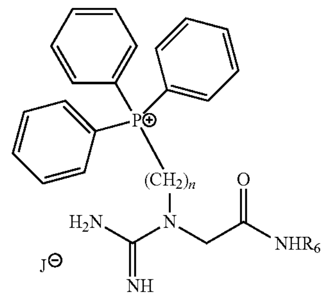
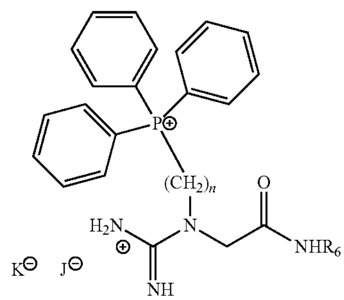
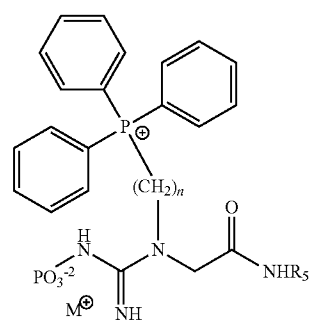
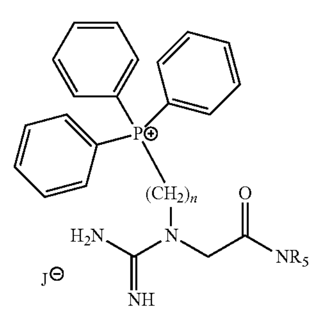
-continued -continued

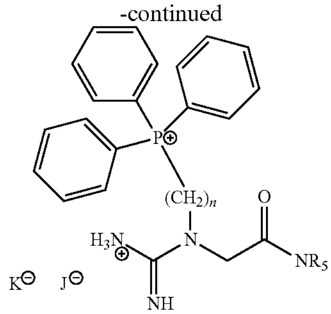

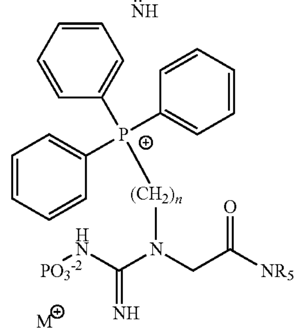

wherein n is an integer between 1 and 12, more particularly between 1 and 8, most particularly between 1 and 6; $R_5$ is as defined above; J and K, when present, refer to X as defined above; and M, when present, is a pharmaceutically acceptable cation as defined above.

Other creatine derivatives include, but are not limited to:

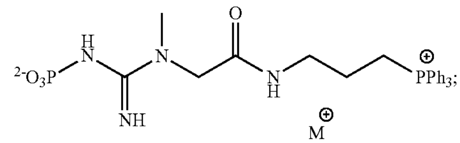

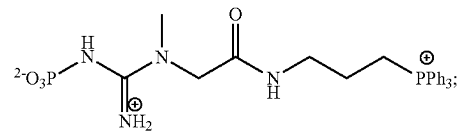

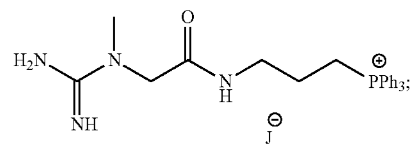

and

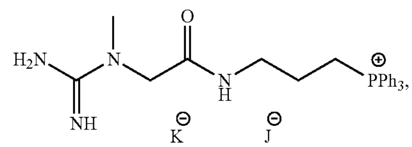

wherein M, J and K are as defined above.

In some embodiments, the creatine derivative of Formula I is found in Table 1:

TABLE 1

| Compound No. | Structure | Name |
|---|---|---|
| A-1 | 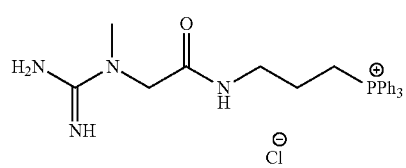 | $N^2$-[amino(imino)methyl]-$N^2$-methyl-N-[3-(triphenylphosphonio)propyl]glycinamide chloride (Mitocreatine chloride) |
| A-2 | 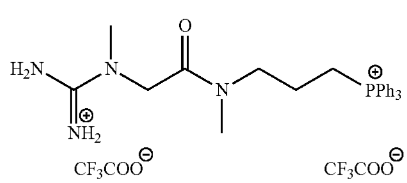 | $N^2$-[ammonio(imino)methyl]-N,$N^2$-dimethyl-N-[3-(triphenylphosphonio)propyl]glycinamide bis(trifluoroacetate) (N-methyl Mitocreatin bistrifluoroacetate) |
| A-3 | 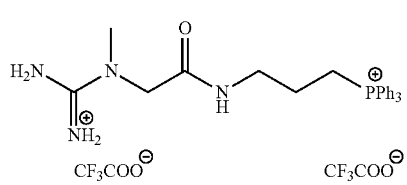 | $N^2$-[ammonio(imino)methyl]-$N^2$-methyl-N-[3-(triphenylphosphonio)propyl] glycinamide bis(trifluoroacetate) (Mitocreatine bistrifluoroacetate) |
| A-4 | 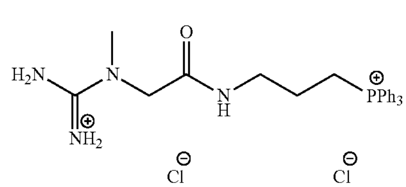 | $N^2$-[ammonio(imino)methyl]-$N^2$-methyl-N-[3-(triphenylphosphonio)propyl] glycinamide dichloride (Mitocreatine dichloride) |

TABLE 1-continued

| Compound No. | Structure | Name |
|---|---|---|
| A-5 | 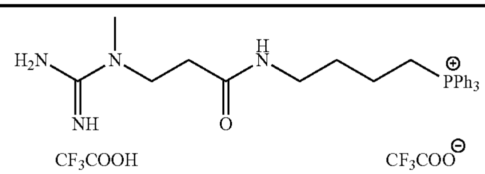 | $N^3$-[amino(imino)methyl]-$N^3$-methyl-N-[4-(triphenylphosphonio)butyl]-β-alaninamide trifluoroacetate - trifluoroacetic acid |
| A-6 | 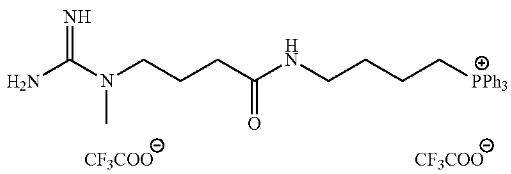 | {4-[(4-{[amino(imino) methyl](methyl)amino}butanoyl)amino] butyl}(triphenyl)phosphonium trifluoroacetate - trifluoroacetic acid |
| A-7 | 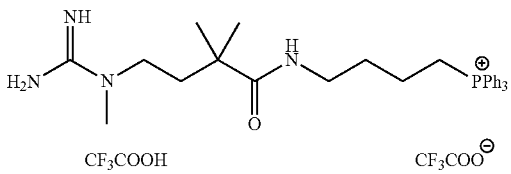 | {4-[(4-{[amino(imino)methyl](methyl)amino}-2,2-dimethylbutanoyl)amino]butyl}(triphenyl) phosphonium trifluoroacetate - trifluoroacetic acid |
| A-8 | 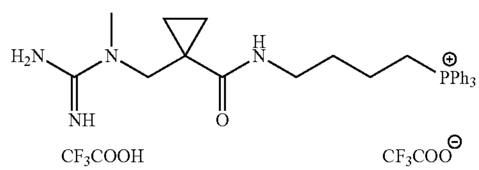 | [3-({[1-({[amino(imino)methyl](methyl)amino} methyl)cyclopropyl]carbonyl}amino)propyl] (triphenyl)phosphonium trifluoroacetate - trifluoroacetic acid |
| A-9 | 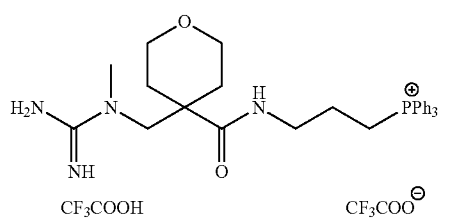 | [3-({[4-({[amino(imino)methyl](methyl)amino} methyl)tetrahydro-2H-pyran-4-yl]carbonyl}amino)propyl](triphenyl) phosphonium trifluoroacetate - trifluoroacetic acid |

Another suitable composition for use with the disclosed methods includes a creatine derivative, $N^2$-[ammonino (imino)methyl]-$N^2$-methyl-N-[3-(triphenylphosphino)propyl]glycinamide (Mitocreatine), or its pharmaceutically acceptable salt, wherein X is pharmaceutically acceptable anion such as chloride or trifluoroacetate. Mitocreatine has the following structure:

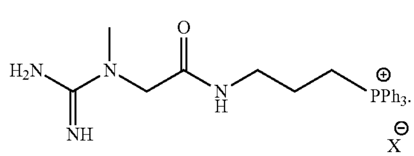

The compounds of Formula I, the variety of embodiments and their preparations are disclosed in WO 2013/043580, which is specifically incorporated by references herein in its entireties.

In some embodiments, the composition typically includes an effective amount of a mitochondrial DNA-binding polypeptide. Examples of a mitochondrial DNA-binding polypeptides include, but are not limited to, mitochondrial transcription factors such as transcription factor A, mitochondrial (TFAM) having GenBank Accession No. mitochondrial NM_003201; transcription factor B1, mitochondrial (TFB1M) having GenBank Accession No. AF151833; transcription factor B2, mitochondrial (TFB2M) having GenBank Accession No. AK026835; Polymerase (RNA) Mitochondrial (DNA directed) (POLRMT) having GenBank Accession No. NM_005035; and functional fragments, variants, and fusion polypeptides thereof. Specifically, X is bromide, chloride, trifluoroacetate, acetate, or mesylate.

In some other embodiments, the preferred embodiments of the composition include a recombinant fusion protein including a polynucleotide-binding polypeptide, a protein transduction domain, and optionally one or more targeting signals. In some embodiments, the disclosed compositions cause an increase in mitochondrial number, an increase in mitochondrial respiration, an increase mitochondrial Electron Transport Chain (ETC) activity, increased oxidative phosphorylation, increased oxygen consumption, increased ATP production, or combinations thereof relative to a control. In preferred embodiments the composition reduces oxidative stress.

Exemplary fusion proteins containing a mitochondrial transcription factor polypeptide are disclosed in U.S. Pat. Nos. 8,039,587, 8,062,891, 8,133,733, and U.S. Published Application Nos. 2009/0123468, 2009/0208478, and 2006/0211647 all of which are specifically incorporated by reference herein in their entireties.

A. Polypeptides

1. Polynucleotide Binding Domain

The compositions for use in the methods disclosed herein include an effective amount of a mitochondrial DNA-binding polypeptide optionally having a PTD and optionally having one or more targeting signals or domains. In certain embodiments, the mitochondrial DNA-binding polypeptide is a polypeptide known to bind or package a mtDNA. Preferably, the mitochondrial DNA-binding polypeptide is a recombinant polypeptide. The recombinant polypeptide can be used as a therapeutic agent either alone or in combination with a polynucleotide, or any other active agent. In preferred embodiments the polynucleotide-binding domain includes mature TFAM, a functional fragment of TFAM, or a variant thereof. In certain embodiments, the polynucleotide-binding polypeptide includes at least a portion of a member of the high mobility group (HMG) of proteins effective to bind a polynucleotide, for example an HMG box domain. Specifically, X is bromide, chloride, trifluoroacetate, acetate, or mesylate.

"Mature TFAM" refers to TFAM after it has been post-translationally modified and is in the form that is active in the mitochondrion. For example, a mature TFAM is one in which the endogenous mitochondrial signal sequence has been cleaved.

a. Transcription Factor A, Mitochondria (TFAM)

One embodiment provides a non-histone polynucleotide-binding polypeptide, for example mitochondrial transcription factor A (TFAM) polypeptide, for functional fragment, or a variant thereof. Variant TFAM can have 80%, 85%, 90%, 95%, 99% or greater sequence identity with a reference TFAM, for example naturally occurring TFAM having GenBank Accession No. NM_003201. In certain embodiments, the variant TFAM has 80%, 85%, 90%, 95%, 99% or greater sequence identity with a reference TFAM. In certain embodiments, the variant TFAM has 80%, 85%, 90%, 95%, 99% or greater sequence identity over the full-length of mature human TFAM.

TFAM is a member of the high mobility group (HMG) of proteins having two HMG-box domains. TFAM as well as other HMG proteins bind, wrap, bend, and unwind DNA. Thus, embodiments of the present disclosure include polynucleotide binding polypeptides including one or more polynucleotide binding regions of the HMG family of proteins, and optionally induce a structural change in the polynucleotide when the polypeptide binds or becomes associated with the polynucleotide.

In some embodiments, the polynucleotide-binding polypeptide is full-length TFAM polypeptide, or variant therefore. For example, a preferred TFAM polypeptide has at least 80, 85, 90, 95, 99, or 100 percent sequence identity to the full-length TFAM precursor.

MAFLRSMWGV LSALGRSGAE LCTGCGSRLR SPFSFVYLPR WFSSVLASCP KKPVSSYLRF SKEQLPIFKA QNPDAKTTEL IRRIAQRWRE LPDSKKKIYQ DAYRAEWQVY KEEISRFKEQ LTPSQIMSLE KEIMDKHLKR KAMTKKKELT LLGKPKRPRS AYNVYVAERF QEAKGDSPQE KLKTVKENWK NLSDSEKELY IQHAKEDETR YHNEMKSWEE QMIEVGRKDL LRRTIKKQRK YGAEEC (SEQ ID NO:1).

Many nuclear encoded mitochondrial proteins destined for the mitochondrial matrix are translated as a "preprotein." The preprotein sequence includes a signal peptide as known as an "amino-terminal signal", or a "presequence" that facilitates translocation from the cytosol through the mitochondrial translocation machinery in the outer membrane called the TOM complex (Translocator outer membrane) as well as the machinery in the inner membrane called the TIM complex (Translocator Inner Membrane). Once the preprotein enters the inner mitochondrial matrix, the signal sequence is cleaved by a protease such as MPP. A mitochondrial protein with the signal sequence cleaved or removed can be referred to as a "mature" protein. Therefore, in some embodiments, the polynucleotide-binding polypeptide is a mature TFAM polypeptide, or variant thereof. For example, in some embodiments, the cleavable mitochondrial targeting sequence of a TFAM preprotein is amino acid residue 1 of SEQ ID NO:1 to amino acid residue 42 of SEQ ID NO:1, MAFLRSMWGV LSALGRSGAE LCTGCGSRLR SPFSFVYLPR WF (SEQ ID NO: 2).

In certain embodiments, a preferred TFAM polypeptide has at least 80, 85, 90, 95, 99, or 100 percent sequence identity to the mature TFAM sequence.

SSVLASCPKK PVSSYLRFSK EQLPIFKAQN PDAKTTELIR RIAQRWRELP DSKKKIYQDA YRAEWQVYKE EISRFKEQLT PSQIMSLEKE IMDKHLKRKA MTKKKELTLL GKPKRPRSAY NVYVAERFQE AKGDSPQEKL KTVKENWKNL SDSEKELYIQ HAKEDETRYH NEMKSWEEQM IEVGRKDLLR RTIKKQRKYG AEEC (SEQ ID NO:3).

In some embodiments, the polynucleotide-binding polypeptide is a functional fragment of TFAM, or variant therefore. Functional fragments can be effective when administered alone, or can be effective when administered in combination with a polynucleotide. Functional fragments of TFAM can include, but are not limited to, a fragment of full-length TFAM sufficient to bind non-specifically to a polynucleotide, a fragment of full-length TFAM sufficient to bind specifically to the mtDNA light strand promoter (LSP), the mtDNA heavy strand promoter 1 (HSP1), the mtDNA heavy stand promoter 2 (HSP2), or combinations thereof, a fragment of full-length TFAM sufficient to induce mitochondrial transcription, a fragment of full-length TFAM sufficient to induce oxidative phosphorylation, a fragment of full-length TFAM sufficient to induce mitochondrial biogenesis, and combinations thereof.

From N-terminus to C-terminus, mature TFAM includes four domains, a first HMG box (also referred to herein as HMG box 1), followed by a linker region (also referred to herein as linker), followed by a second HMG box (also referred to herein as HMG box 2), followed by a C-terminal tail. Functional fragments of TFAM typically include one or more domains of mature TFAM, or a variant thereof. For example, in some embodiments, the functional fragment includes one or more HMG box 1 domains of TFAM, one or more linker domains of TFAM, one or more HMG box 2 domains of TFAM, one or more C-terminal tail domains of TFAM, or combinations thereof. The domains can be arranged in the same orientation of the domains of endogenous TFAM, or they can be rearranged so they are in a different order or orientation than the domains found in endogenous TFAM protein. In certain embodiments the functional fragment includes a first HMG box domain, and second HMG box domain linked to the first HMG box domain with a linker, typically a peptide linker. The linker can be the endogenous linker domain of TFAM, or a heterologous linker that allows the first and the second HMG box domains to maintain their functional activity. Deletion studies characterizing the activity of different domains and hybrid constructs of TFAM are known in the art and characterized for example in Dairaghi, et al., *J. Mol. Biol.*, 249:11-28 (1995), Matsushima, et al., *J. Biol. Chem.*, 278 (33):31149-31158 (2003), and Gangeloff, et al., *Nucl. Acid. Res.*, 37(10):3153-3164 (2009), all of which are specifically incorporated by reference herein in the entireties.

In certain embodiments a functional fragment is one or more domains of TFAM according to SEQ ID NO: 3. For example, an HMG box 1 of TFAM can be a polypeptide including the sequence from amino acid residue 1, 2, 3, 4, 5, 6, 7, 8, 9, or 10 of SEQ ID NO: 3 to amino acid residue 70, 71, 72, 73, 74, 75, 76, 77, 78, 79, 80, 81, 82, 83, 84, 85, 86, 87, 88, 89, 90, 91, 92, 93, 94, or 95 of SEQ ID NO: 3, or a variant thereof with 80, 85, 90, 95, 99, or greater than 99 percent sequence identity to the corresponding fragment of SEQ ID NO: 3.

A linker region of TFAM can be a polypeptide including the sequence from amino acid residue 70, 71, 72, 73, 74, 75, 76, 77, 78, 79, 80, 81, 82, 83, 84, or 85 of SEQ ID NO: 3 to amino acid residue 105, 106, 107, 108, 109, 110, 111, 112, 113, 114, or 115 of SEQ ID NO: 3, or a variant thereof with 80, 85, 90, 95, 99, or greater than 99 percent sequence identity to the corresponding fragment of SEQ ID NO: 3.

An HMG box 2 of TFAM can be a polypeptide including the sequence from amino acid residue 96, 97, 98, 99, 100, 101, 102, 103, 104, 105, 106, 107, 108, 109, 110, 111, 112, 113, 114, or 115 of SEQ ID NO: 3 to amino acid residue 172, 173, 174, 175, 176, 177, 178, 179, 180, 181, 182, 183, 184, 185, 186, or 187 of SEQ ID NO: 3, or a variant thereof with 80, 85, 90, 95, 99, or greater than 99 percent sequence identity to the corresponding fragment of SEQ ID NO: 3.

A C-terminal tail of TFAM can be a polypeptide including the sequence from amino acid residue 172, 173, 174, 175, 176, 177, 178, 179, 180, 181, 182, 183, 184, 185, 186, or 187 of SEQ ID NO: 3 to amino acid residue 194, 195, 196, 197, 198, 199, 200, 201, 202, 203, or 204 of SEQ ID NO: 3, or a variant thereof with 80, 85, 90, 95, 99, or greater than 99 percent sequence identity to the corresponding fragment of SEQ ID NO: 3.

Variants of TFAM and functional fragments of TFAM are also provided. Typically, the variants of TFAM and functional fragments of TFAM include one or more conservative amino acid substitutions relative to the corresponding reference sequence, for example SEQ ID NO:3, or a fragment thereof. One embodiment provides a TFAM polypeptide having one or more serine residues at positions 1, 2 and 13 (SEQ ID NO: 3) substituted with an alanine or threonine residue. A preferred embodiment provides a TFAM polypeptide having serine 13 of SEQ ID NO:3 substituted for an alanine or threonine. The variant TFAM polypeptides have improved mtDNA binding in the presence of glucose or elevated glucose levels.

Selected model organisms that have TFAM sequences that are useful in the compositions and methods disclosed herein include, but are not limited to those disclosed in Table 3.

TABLE 3

| Organism, Protein And Percent Identity And Length Of Aligned Region | | |
|---|---|---|
| *H. sapiens* | sp: Q00059 - MTT1_HUMAN Transcription factor 1, mitochondrial precursor (MTTF1) | 100%/246 aa (see ProtEST) |
| *M. musculus* | ref: NP_033386.1 - transcription factor A, mitochondrial [*Mus musculus*] | 63%/237 aa (see ProtEST) |

TABLE 3-continued

| Organism, Protein And Percent Identity And Length Of Aligned Region | | |
|---|---|---|
| *R. norvegicus*: | ref: NP_112616.1 - transcription factor A, mitochondrial [*Rattus norvegicus*] | 64%/237 aa (see ProtEST) |
| *A. thaliana* | ref: NP_192846.1 - 98b like protein [*Arabidopsis thaliana*] | 27%/189 aa (see ProtEST) |
| *C. elegans* | ref: NP_501245.1 - F45E4.9.p [*Caenorhabditis elegans*] | 27%/189 aa (see ProtEST) |
| *D. melanogaster*: | ref: NP_524415.1 - mitochondrial transcription factor A [*Drosophila melanogaster*] | 34%/183 aa (see ProtEST) |

b. Transcription Factor B1, Mitochondrial (TFB1M)

The polynucleotide-binding polypeptide can be transcription factor B1, mitochondrial (TFB1M). A preferred TFB1M has GenBank Accession No. AF151833. TFB1 is part of the complex involved in mitochondrial transcription. The process of transcription initiation in mitochondria involves three types of proteins: the mitochondrial RNA polymerase (POLRMT), mitochondrial transcription factor A (TFAM), and mitochondrial transcription factors B1 and B2 (TFB1M, TFB2M). POLRMT, TFAM, and TFB1M or TFB2M assemble at the mitochondrial promoters and begin transcription. TFB1M has about 1/10 the transcriptional activity of TFB2M, and both TFBs are also related to rRNA methyltransferases and TFB1M can bind S-adenosylmethionine and methylate mitochondrial 12S rRNA. Additionally, TFB1M and TFB2M can bind single-stranded nucleic acids.

A preferred TFB1M polypeptide has at least 80, 85, 90, 95, 99, or 100 percent sequence identity to MAASGKLSTC RLPPLPTIRE IIKLLRLQAA NELSQNFLLD LRLTDKIVRK AGNLTNAYVY EVGPGPGGIT RSILNADVAE LLVVEKDTRF IPGLQMLSDA APGKLRIVHG DVLTFKVEKA FSESLKRPWE DDPPNVHIIG NLPFSVSTPL IIKWLENISC RDGPFVYGRT QMTLTFQKEV AERLAANTGS KQRSRLSVMA QYLCNVRHIF TIPGQAFVPK PEVDVGVVHF TPLIQPKIEQ PFKLVEKVVQ NVFQFRRKYC HRGLRMLFPE AQRLESTGRL LELADIDPTL RPRQLSISHF KSLCDVYRKM CDEDPQLFAY NFREELKRRK SKNEEKEEDD AENYRL (SEQ ID NO:4).

c. Transcription Factor B2, Mitochondrial (TFB2M)

In still another embodiment, the polynucleotide-binding polypeptide includes TFB2M. In a preferred embodiment the TFB2M polypeptide has GenBank Accession No. AK026835. TFB2M also possesses a Rossmann-fold making it part of the NAD-binding protein family. TFB2M levels modulate mtDNA copy number and levels of mitochondrial transcripts as would be expected of a mitochondrial transcription factor. It is appreciated by those skilled in the art that increased activity of mitochondria causes an increase in mitochondrial biogenesis.

A preferred TFB2M polypeptide has at least 80, 85, 90, 95, 99, or 100 percent sequence identity to MWIPVVGLPR RLRLSALAGA GRFCILGSEA ATRKHLPARN HCGLSDSSPQ LWPEPDFRNP PRKASKASLD FKRYVTDRRL AETLAQIYLG KPSRPPHLLL ECNPGPGILT QALLEAGAKV VALESDKTFI PHLESLGKNL DGKLRVIHCD FFKLDPRSGG VIKPPAMSSR GLFKNLGIEA VPWTADIPLK VVGMFPSRGE KRALWKLAYD LYSCTSIYKF GRIEVNMFIG EKEFQKLMAD PGNPDLYHVL SVIWQLACEI KVLHMEPWSS FDIYTRKGPL ENPKRRELLD QLQQKLYLIQ MIPRQNLFTK NLTPMNYNIF FHLLKHCFGR RSATVIDHLR SLTPLDARDI LMQIGKQEDE KVVNMHPQDF KTLFETIERS KDCAYKWLYD ETLEDR (SEQ ID NO:5).

d. Polymerase (RNA) Mitochondrial (DNA Directed) (POLRMT)

Still another polynucleotide-binding polypeptide that can be used to modulate mitochondrial biological activity is POLRMT. In a preferred embodiment, the POLRMT polypeptide has GenBank Accession No. NM_005035. POLRMT is a mitochondrial RNA polymerase similar in structure to phage RNA polymerases. Unlike phage polymerases, POLRMT contains two pentatricopeptide repeat (PPR) domains involved in regulating mitochondrial transcripts. It is appreciated by those skilled in the art that deletion of regulatory domains enables constitutive function.

A preferred POLRMT polypeptide has at least 80, 85, 90, 95, 99, or 100 percent sequence identity to MSALCWGRGA AGLKRALRPC GRPGLPGKEG TAGGVCGPRR SSSASPQEQD QDRRKDWGHV ELLEVLQARV RQLQAESVSE VVVNRVDVAR LPECGSGDGS LQPPRKVQMG AKDATPVPCG RWAKILEKDK RTQQMRMQRL KAKLQMPFQS GEFKALTRRL QVEPRLLSKQ MAGCLEDCTR QAPESPWEEQ LARLLQEAPG KLSLDVEQAP SGQHSQAQLS GQQQRLLAFF KCCLLTDQLP LAHHLLVVHH GQRQKRKLLT LDMYNAVMLGWARQGAFKEL VYVLFMVKDA GLTPDLLSYA AALQCMGRQD QDAGTIERCL EQMSQEGLKL QALFTAVLLS EEDRATVLKA VHKVKPTFSL PPQLPPPVNT SKLLRDVYAK DGRVSYPKLH LPLKTLQCLF EKQLHMELAS RVCVVSVEKP TLPSKEVKHA RKTLKTLRDQ WEKALCRALR ETKNRLEREV YEGRFSLYPF LCLLDEREVV RMLLQVLQAL PAQGESFTTL ARELSARTFS RHVVQRQRVS GQVQALQNHY RKYLCLLASD AEVPEPCLPR QYWEELGAPE ALREQPWPLP VQMELGKLLA EMLVQATQMP CSLDKPHRSSRLVPVLYHVY SFRNVQQIGI LKPHPAYVQL LEKAAEPTLT FEAVDVPMLC PPLPWTSPHS GAFLLSPTKL MRTVEGATQH QELLETCPPT ALHGALDALT QLGNCAWRVN GRVLDLVLQL FQAKGCPQLG VPAPPSEAPQ PPEAHLPHSA APARKAELRR ELAHCQKVAR EMHSLRAEAL YRLSLAQHLR DRVFWLPHNM DFRGRTYPCP PHFNHLGSDV ARALLEFAQG RPLGPHGLDW LKIHLVNLTG LKKREPLRKR LAFAEEVMDD ILDSADQPLT GRKWWMGAEE PWQTLACCMEVANAVRASDPAAYVSHLPVH QDGSCNGLQH YAALGRDSVG AASVNLEPSD VPQDVYSGVA AQVEVFRRQD AQRGMRVAQV LEGFITRKVV KQTVMTVVYG VTRYGGRLQI EKRLRELSDF PQEFVWEASH YLVRQVFKSL QEMFSGTRAI QHWLTESARL ISHMGSVVEW VTPLGVPVIQ PYRLDSKVKQ IGGGIQSITY THNGDISRKP NTRKQKNGFP PNFIHSLDSS HMMLTALHCY RKGLTFVSVH DCYWTHAADV SVMNQVCREQ FVRLHSEPIL QDLSRFLVKR FCSEPQKILE ASQLKETLQA VPKPGAFDLE QVKRSTYFFS (SEQ ID NO: 36).

e. HMG Domain

In some embodiments, the polynucleotide-binding polypeptide is a non-TFAM HMG domain. Generally, the HMG domain includes a global fold of three helices stabilized in an 'L-shaped configuration by two hydrophobic cores. The high mobility group chromosomal proteins HMG1 or HMG2, which are common to all eukaryotes, bind DNA in a non-sequence-specific fashion, for example to promote chromatin function and gene regulation. They can interact directly with nucleosomes and are believed to be modulators of a chromatin structure. They are also important in activating a number of regulators of gene expression, including p53, Hox transcription factors and steroid hormone receptors, by increasing their affinity for DNA. HMG proteins include HMG-1/2, HMG-I(Y) and HMG-14/17.

The HMG-1/2-box proteins can be further distinguished into three subfamilies according to the number of HMG domains present in the protein, their specific sequence recognition and their evolutionary relationship. The first group contains chromosomal proteins bound to DNA with no sequence specificity (class I, HMG1 and HMG2), the second contains ribosomal and mitochondrial transcription factors which show sequence specificity in the presence of another associating factor when bound with DNA (class II, yeast ARS binding protein ABF-2, UBF and mitochondrial transcription factor mtTF-1), and the third contains gene-specific transcription factors which show sequence specific DNA binding (class III, lymphoid enhancer-binding factors LEF-1 and TCF-1; the mammalian sex-determining factor SRY, and the closely related SOX proteins; and the fungal regulatory proteins Mat-MC, Mat-a1, Ste11 and Rox1). The HMG1/2-box DNA binding domain is about 75 to about 80 amino acids and contains highly conserved proline, aromatic and basic residues. Common properties of HMG domain proteins include interaction with the minor groove of the DNA helix, binding to irregular DNA structures, and the capacity to modulate DNA structures by bending.

SOX (SRY-type HMG box) proteins have critical functions in a number of developmental processes, including sex determination, skeleton formation, pre-B and T cell development and neural induction. SOX9 plays a direct role during chondrogenesis by binding and activating the chondrocyte-specific enhancer of the Col2a1 gene. Loss of SOX9 gene function leads to the genetic condition known as Campomelic Dysplsia (CD), a form of dwarfism characterized by extreme skeletal malformation, and one in which three-quarters of XY individuals are either intersexes or exhibit male to female sex reversal. There are more than 20 members cloned in the SOX family. All of which contain an HMG domain, which can bind specifically to the double strand DNA motif and shares >50% identify with the HMG domain of SRY, the human testis-determining factor. The preferred DNA-binding site of SOX9 has been defined to be AGAACAATGG (SEQ ID NO: 6), which contains the SOX core-binding element (SCBE), AACAAT, flanking 5' AG and 3' GG nucleotides enhance binding by SOX9.

In one embodiment, the recombinant polynucleotide-binding polypeptide has at least one HMG box domain, generally at least two, more particularly 2-5 HMG box domains. The HMG box domain can bind to an AT rich DNA sequence, for example, using a large surface on the concave face of the protein, to bind the minor groove of the DNA. This binding bends the DNA helix axis away from the site of contact. The first and second helices contact the DNA, their N-termini fitting into the minor groove whereas helix 3 is primarily exposed to solvent. Partial intercalation of aliphatic and aromatic residues in helix 2 occurs in the minor groove.

In other embodiments, the polynucleotide-binding polypeptide can have at least one polynucleotide binding domain, and typically has two or more polynucleotide binding domains. The polynucleotide binding domains can be the same or different. For example, the polynucleotide-binding polypeptide can include at least one HMG box in combination with one or more DNA binding domains selected from the group consisting of an HMG box, homeodomain and POU domain; zinc finger domain such as $C_2H_2$ and $C_2C_2$; amphipathic helix domain such as leucine zipper and helix-loop-helix domains; and histone folds. The polynucleotide binding domain can be specific for a specific polynucleotide sequence, or preferably non-specifically binds to a polynucleotide. Alternatively, the polynucleotide-binding polypeptide can have more of a combination of at least one polynucleotide binding domain that binds in a sequence specific manner and at least one polynucleotide binding-domain that binds DNA non-specifically.

f. Helix-Turn-Helix

Certain embodiments provide polynucleotide-binding polypeptides having a helix-turn-helix motif or at least a polynucleotide binding region of a helix-turn-helix protein. Helix-turn-helix proteins have a similar structure to bacterial regulatory proteins such as the 1 repressor and cro proteins, the lac repressor and so on which bind as dimers and their binding sites are palindromic. They contain 3 helical regions separated by short turns which is why they are called helix-turn-helix proteins. One protein helix (helix 3) in each subunit of the dimer occupies the major groove of two successive turns of the DNA helix. Thus, in another embodiment, the disclosed polynucleotide-binding polypeptides can form dimers or other multi-component complexes, and have 1 to 3 helices.

g. Homeodomain

In yet another embodiment, the polynucleotide-binding polypeptide includes a homeodomain or a portion of a homeodomain protein. Homeodomain proteins bind to a sequence of 180 base pairs initially identified in a group of genes called homeotic genes. Accordingly, the sequence was called the homeobox. The 180 bp corresponds to 60 amino acids in the corresponding protein. This protein domain is called the homeodomain. Homeodomain-containing proteins have since been identified in a wide range of organisms including vertebrates and plants. The homeodomain shows a high degree of sequence conservation. The homeodomain contains 4 $\alpha$ helical regions. Helices II and III are connected by 3 amino acids comprising a turn. This region has a very similar structure to helices II and III of bacterial DNA binding proteins.

h. Zinc Finger

Yet another embodiment provides a modified polynucleotide-binding polypeptide having a zinc finger domain or at least a portion of a zinc finger protein Zinc finger proteins have a domain with the general structure: Phe (sometimes Tyr)-Cys-2 to 4 amino acids-Cys-3 amino acids-Phe (sometimes Tyr)-5 amino acids-Leu-2 amino acids-His-3 amino acids-His. The phenylalanine or tyrosine residues which occur at invariant positions are required for DNA binding. Similar sequences have been found in a range of other DNA binding proteins though the number of fingers varies. For example, the SP1 transcription factor which binds to the GC box found in the promoter proximal region of a number of genes has 3 fingers. This type of zinc finger which has 2 cysteines and 2 histidines is called a $C_2H_2$ zinc finger.

Another type of zinc finger which binds zinc between 2 pairs of cysteines has been found in a range of DNA binding proteins. The general structure of this type of zinc finger is: Cys-2 amino acids-Cys-13 amino acids-Cys-2 amino acids-Cys. This is called a $C_2C_2$ zinc finger. It is found in a group of proteins known as the steroid receptor superfamily, each of which has 2 $C_2C_2$ zinc fingers.

i. Leucine Zipper

Another embodiment provides a modified polynucleotide-binding polypeptide having a leucine zipper or at least a portion of a leucine zipper protein. The first leucine zipper protein was identified from extracts of liver cells, and it was called C/EBP because it is an enhancer binding protein and it was originally thought to bind to the CAAT promoter proximal sequence. C/EBP will only bind to DNA as a dimer. The region of the protein where the two monomers join to make the dimer is called the dimerization domain. This lies towards the C-terminal end of the protein. When the amino acid sequence was examined it was found that a leucine residue occurs every seventh amino acid over a stretch of 35 amino acids. If this region were to form an a helix then all of these leucines would align on one face of the helix.

Because leucine has a hydrophobic side chain, one face of the helix is very hydrophobic. The opposite face has amino acids with charged side chains which are hydrophilic. The combination of hydrophobic and hydrophilic characteristics gives the molecule is amphipathic moniker. Adjacent to the leucine zipper region is a region of 20-30 amino acids which is rich in the basic (positively charged) amino acids lysine and arginine. This is the DNA binding domain-often referred to as the bZIP domain—the basic region of the leucine zipper. C/EBP is thought to bind to DNA by these bZIP regions wrapping round the DNA helix.

The leucine zipper-bZIP structure has been found in a range of other proteins including the products of the jun and fos oncogenes. Whereas C/EBP binds to DNA as a homodimer of identical subunits, fos cannot form homodimers at all and jun/jun homodimers tend to be unstable. However fos/jun heterodimers are much more stable. These fos/jun heterodimers correspond to a general transcription factor called AP1 which binds to a variety of promoters and enhancers and activates transcription. The consensus AP1 binding site is TGACTCA which is palindromic.

j. Helix-Loop-Helix

Another embodiment provides a modified polynucleotide-binding polypeptide having helix-loop-helix domain or a polynucleotide binding portion of a helix-loop-helix protein. Helix-loop-helix proteins are similar to leucine zippers in that they form dimers via amphipathic helices. They were first discovered as a class of proteins when a region of similarity was noticed between two enhancer binding proteins called E47 and E12. This conserved region has the potential to form two amphipathic separated by a loop hence helix-loop-helix. Next to the dimerization domain is a DNA binding domain, again rich in basic amino acids and referred to as the bHLH domain. These structures are also found in a number of genes required for development of the *Drosophila* nervous system—the Achaete-scute complex, and in a protein called MyoD which is required for mammalian muscle differentiation.

k. Histone Fold

In still another embodiment, the modified polynucleotide-binding polypeptide includes a histone polypeptide, a fragment of a histone polypeptide, or at least one histone fold. Histone folds exist in histone polypeptide monomers assembled into dimers. Histone polypeptides include H2A, H2B, H3, and H4 which can form heterodimers H2A-2B and H3-H4. It will be appreciated that histone-like polypeptides can also be used in the disclosed compositions and methods. Histone-like polypeptides include, but are not limited to, HMf or the histone from *Methanothermous fervidus*, other archaeal histones known in the art, and histone-fold containing polypeptides such as MJ1647, CBF, TAFII or transcription factor IID, SPT3, and Drl-DRAP (Sanderman, K., et al., *Cell. Mol. Life Sci.* 54:1350-1364 (1998), which is specifically incorporated by reference herein in its entirety).

2. Protein Transduction Domain

In some embodiments, the polynucleotide-binding polypeptide is fusion protein modified to include a protein transduction domain (PTD). As used herein, a "protein transduction domain" or PTD refers to a polypeptide, polynucleotide, carbohydrate, organic or inorganic compound that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle.

In preferred embodiments, the protein transduction domain is a polypeptide. A protein transduction domain can be a polypeptide including positively charged amino acids. Thus, some embodiments include PTDs that are cationic or amphipathic. Protein transduction domains (PTD), also known as a cell penetrating peptides (CPP), are typically polypeptides including positively charged amino acids. PTDs are known in the art, and include, but are not limited to small regions of proteins that are able to cross a cell membrane in a receptor-independent mechanism (Kabouridis, P., *Trends in Biotechnology* (11):498-503 (2003)). Although several PTDs have been documented, the two most commonly employed PTDs are derived from TAT (Frankel and Pabo, *Cell,* 55(6):1189-93(1988)) protein of HIV and Antennapedia transcription factor from *Drosophila*, whose PTD is known as Penetratin (Derossi et al., *J Biol Chem.,* 269(14):10444-50 (1994)). Exemplary protein transduction domains include polypeptides with 11 Arginine residues, or positively charged polypeptides or polynucleotides having 8-15 residues, preferably 9-11 residues.

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRR R (SEQ ID NO:7)) of the parent protein that appears to be critical for uptake. Additionally, the basic domain Tat(49-57) or RKKRRQRRR (SEQ ID NO:8) has been shown to be a PTD. In the current literature TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al., *Proc Natl Acad Sci USA.,* 97(24):13003-8 (2000)) to up to 33 fold in mammalian cells. (Ho et al., *Cancer Res.,* 61(2):474-7 (2001)).

The most efficient uptake of modified proteins was revealed by mutagenesis experiments of TAT-PTD, showing that an 11 arginine stretch was several orders of magnitude more efficient as an intercellular delivery vehicle. Therefore, PTDs can include a sequence of multiple arginine residues, referred to herein as poly-arginine or poly-ARG. In some embodiments the sequence of arginine residues is consecutive. In some embodiments the sequence of arginine residues is non-consecutive. A poly-ARG can include at least 7 arginine residues, more preferably at least 8 arginine residues, most preferably at least 11 arginine residues. In some embodiments, the poly-ARG includes between 7 and 15 arginine residues, more preferably between 8 and 15 arginine residues. In some embodiments the poly-ARG includes between 7 and 15, more preferably between 8 and 15 consecutive arginine residues. An example of a poly-ARG is RRRRRRR (SEQ ID NO: 9). Additional exemplary PTDs include, but are not limited to; RRQRRTSKLM KR (SEQ ID NO: 10); GWTLNSAGYL LGKINLKALA ALAKKIL (SEQ ID NO:11); WEAKLAKALA KALAKHLAKA LAKALKCEA (SEQ ID NO:12); and RQIKIWFQNR RMKWKK (SEQ ID NO: 13).

Without being bound by theory, it is believed that following an initial ionic cell-surface interaction, some polypeptides containing a protein transduction domain are rapidly internalized by cells via lipid raft-dependent macropinocytosis. For example, transduction of a TAT-fusion protein was found to be independent of interleukin-2 receptor/raft-, caveolar- and clathrin-mediated endocytosis and phagocytosis (Wadia, et al., *Nature Medicine,* 10:310-315 (2004), and Barka, et al., *J. Histochem. Cytochem.,* 48(11):1453-60 (2000)). Therefore, in some embodiments the polynucleotide-binding polypeptide includes an endosomal escape sequence that enhances escape of the polypeptide-binding protein from macropinosomes. In some embodiments the endosomal escape sequence is part of, or consecutive with, the protein transduction domain. In some embodiments the endosomal escape sequence is non-consecutive with the protein transduction domain. In some embodiments the endosomal escape sequence includes a portion of the hemagglutinin peptide from influenza (HA). One example of an endosomal escape sequence includes GDIMGEWG NEIFGAIAGF LG (SEQ ID NO: 14).

In one embodiment a protein transduction domain including an endosomal escape sequence includes the amino acid sequence RRRRRRRRRR RGEGDIMGEW GNEIFGAIAG FLGGE (SEQ ID NO: 15).

3. Targeting Signal or Domain

In some embodiments the polynucleotide-binding polypeptide is modified to include one or more targeting signals or domains. The targeting signal can include a sequence of monomers that facilitates in vivo localization of the molecule. The monomers can be amino acids, nucleotide or nucleoside bases, or sugar groups such as glucose, galactose, and the like which form carbohydrate targeting signals. Targeting signals or sequences can be specific for a host, tissue, organ, cell, organelle, non-nuclear organelle, or cellular compartment. For example, in some embodiments the polynucleotide-binding polypeptide includes both a cell-specific targeting domain and an organelle specific targeting domain to enhance delivery of the polypeptide to a subcellular organelle of a specific cells type.

i. Organelle Targeting

In some embodiments, the polynucleotide-binding polypeptide is modified to target a subcellular organelle. Targeting of the disclosed polypeptides to organelles can be accomplished by modifying the disclosed compositions to contain specific organelle targeting signals. These sequences can target organelles, either specifically or non-specifically. In some embodiments the interaction of the targeting signal with the organelle does not occur through a traditional receptor-ligand interaction.

The eukaryotic cell comprises a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure.

Organelles can have single or multiple membranes and exist in both plant and animal cells. Depending on the function of the organelle, the organelle can consist of specific components such as proteins and cofactors. The polypeptides delivered to the organelle can enhance or contribute to the functioning of the organelle. Some organelles, such as mitochondria and chloroplasts, contain their own genome. Nucleic acids are replicated, transcribed, and translated within these organelles. Proteins are imported and metabolites are exported. Thus, there is an exchange of material across the membranes of organelles. Exemplary organelles include the nucleus, mitochondrion, chloroplast, lysosome, peroxisome, Golgi, endoplasmic reticulum, and nucleolus. Synthetic organelles can be formed from lipids and can contain specific proteins within the lipid membranes. Additionally, the content of synthetic organelles can be manipulated to contain components for the translation of nucleic acids.

Targeting the Mitochondria

In certain embodiments polynucleotide-binding polypeptides are disclosed that specifically target mitochondria. Mitochondria contain the molecular machinery for the conversion of energy from the breakdown of glucose into adenosine triphosphate (ATP). The energy stored in the high energy phosphate bonds of ATP is then available to power cellular functions. Mitochondria are mostly protein, but some lipid, DNA and RNA are present. These generally spherical organelles have an outer membrane surrounding an inner membrane that folds (cristae) into scaffolding for oxidative phosphorylation and electron transport enzymes. Most mitochondria have flat shelf-like cristae, but those in steroid secreting cells may have tubular cristae. The mitochondrial matrix contains the enzymes of the citric acid cycle, fatty acid oxidation and mitochondrial nucleic acids.

Mitochondrial DNA is double stranded and circular. Mitochondrial RNA comes in the three standard varieties; ribosomal, messenger and transfer, but each is specific to the mitochondria. Some protein synthesis occurs in the mitochondria on mitochondrial ribosomes that are different than cytoplasmic ribosomes. Other mitochondrial proteins are made on cytoplasmic ribosomes with a signal peptide that directs them to the mitochondria. The metabolic activity of the cell is related to the number of cristae and the number of mitochondria within a cell. Cells with high metabolic activity, such as heart muscle, have many well developed mitochondria. New mitochondria are formed from preexisting mitochondria when they grow and divide.

The inner membranes of mitochondria contain a family of proteins of related sequence and structure that transport various metabolites across the membrane. Their amino acid sequences have a tripartite structure, made up of three related sequences about 100 amino acids in length. The repeats of one carrier are related to those present in the others and several characteristic sequence features are conserved throughout the family.

Mitochondrial targeting agents generally consist of a leader sequence of highly positively charged amino acids. This allows the protein to be targeted to the highly negatively charged mitochondria. Unlike receptor-ligand approaches that rely upon stochastic Brownian motion for the ligand to approach the receptor, the mitochondrial localization signal of some embodiments is drawn to mitochondria because of charge. Therefore, in some embodiments, the mitochondrial targeting agent is a protein transduction domain including but not limited to the protein transduction domains discussed in detail above.

Mitochondrial targeting agents also include short peptide sequences (Yousif, et al., *Chembiochem.,* 10(13):2131 (2009)), for example mitochondrial transporters-synthetic cell-permeable peptides, also known as mitochondria-penetrating peptides (MPPs), that are able to enter mitochondria. MPPs are typically cationic, but also lipophilic; this combination of characteristics facilitates permeation of the hydrophobic mitochondrial membrane. For example, MPPs can include alternating cationic and hydrophobic residues (Horton, et al., *Chem Biol.,* 15(4):375-82 (2008)). Some MPPs include delocalized lipophilic cations (DLCs) in the peptide sequence instead of, or in addition to natural cationic amino acids (Kelley, et al., *Pharm. Res.,* 2011 Aug. 11 [Epub ahead of print]). Other variants can be based on an oligomeric carbohydrate scaffold, for example attaching guanidinium moieties due to their delocalized cationic form (Yousif, et al., *Chembiochem.,* 10(13):2131 (2009)).

Mitochondrial targeting agents also include mitochondrial localization signals or mitochondrial targeting signals. Many mitochondrial proteins are synthesized as cytosolic precursor proteins containing a leader sequence, also known as a presequence, or peptide signal sequence. Typically, cytosolic chaperones deliver the precursor protein to mitochondrial receptors and the General Import Pore (GIP) (Receptors and GIP are collectively known as Translocase of Outer Membrane or TOM) at the outer membrane. Typically, the precursor protein is translocated through TOM, and the intermembrane space by small TIMs to the TIM23 or 22 (Translocase of Inner Membrane) at the inner membrane. Within the mitochondrial matrix the targeting sequence is cleaved off by mtHsp70.

As discussed above, in order to enter the mitochondria, a protein generally must interact with the mitochondrial import machinery, consisting of the TIM and TOM complexes (Translocase of the Inner/Outer Mitochondrial Membrane). With regard to the mitochondrial targeting signal, the positive charge draws the linked protein to the complexes and continues to draw the protein into the mitochondria. The TIM and TOM complexes allow the proteins to cross the membranes. Accordingly, one embodiment of the present disclosure delivers compositions of the present disclosure to the inner mitochondrial space utilizing a positively charged targeting signal and the mitochondrial import machinery. In another embodiment, PTD-linked compounds containing a mitochondrial localization signal do not seem to utilize the TOM/TIM complex for entry into the mitochondrial matrix, see Del Gaizo et al. *Mol Genet Metab.* 80(1-2):170-80 (2003). The N-terminal region of the proteins can be used to target molecules to the mitochondrion. The sequences are known in the art, see for example, U.S. Pat. No. 8,039,587, which is specifically incorporated by reference herein. The identification of the specific sequences necessary for translocation of a linked compound into a mitochondrion can be determined using predictive software known to those skilled in the art, including the tools located at http://ihg.gsf.de/ihg/mitoprot.html. Using the software the predicted sequence from Etfa that can be used to target the disclosed composition is MFRAAAPGQL RRAASLLRF (SEQ ID NO:16).

The predicted mitochondrial targeting signal from Dld is MQSWSRVYCS LAKRGHFNRI SHGLQGLSAV PLRTY (SEQ ID NO:17).

In certain embodiments, the mitochondrial targeting agent is the mitochondrial localization signal of a manganosuperoxide dismutase (also referred to herein as "SOD2" and "Mn-SOD" and "superoxide dismutase (Mn)) precursor protein. Several mitochondrial localization signals for SOD2 are known in the art. In some embodiments the mitochondrial targeting signal includes the amino acid sequence MLSRAVCGTS RQLAPVLGYL GSRQ (SEQ ID NO:18) or SEQ ID NO: 18 without the N-terminal methionine LSRAVCGTSR QLAPVLGYLG SRQ (SEQ ID NO:19).

In another embodiment the mitochondrial targeting signal includes the amino acid sequence MLSRAVCGTS RQLAPVLGYL GSRQ (SEQ ID NO:20); or SEQ ID NO:20 without the N-terminal methionine LSRAVCGTSR QLAPVLGYLG SRQ (SEQ ID NO:21).

In some embodiments, the composition is preferentially delivered to the mitochondrial using a mitochondrial delivery vehicle, such as a lipid raft, mitochondrially targeted nanoparticle, or mitochondriotropic liposome. In such cases, one or more polynucleotide-binding polypeptides can be associated with, encapsulated within, dispersed in or on, or covalently attached to the mitochondrial delivery vehicle.

In certain embodiments, polynucleotide-binding polypeptides are encapsulated, coupled to, or otherwise associated with mitochondriotropic liposomes. Mitochondriotrophic liposomes are cationic liposomes that can be used to deliver an encapsulated agent to the mitochondria of a cell. Mitochondriotropic liposomes are known in the art. See, for example, U.S. Patent Application Publication No. US 2008/0095834 to Weissig, et al, which is specifically incorporated by reference herein in its entirety. Mitochondriotropic liposomes are liposomes which contain a hydrophobized amphiphilic delocalized cation, such as a triphenylphosphonium or a quinolinium moiety, incorporated into or conjugate to the lipid membrane of the liposome. As a result, the liposomes can be used to deliver compounds incorporated within them to the mitochondria.

In other embodiments, polynucleotide-binding polypeptides are encapsulated within, dispersed in, associated with, or conjugated to a nanoparticle functionalized with one or more mitochondrial targeting agents. For example, the nanoparticle may contain one or be functionalized with one or more lipophilic cations or polypeptide targeting agents.

The nanoparticles may be formed from one or more polymers, copolymers, or polymer blends. In some embodiments, the one or more polymers, copolymers, or polymer blends are biodegradable. Examples of suitable polymers include, but are not limited to, polyhydroxyacids such as poly(lactic acid), poly(glycolic acid), and poly(lactic acid-co-glycolic acids); polycaprolactones; poly(orthoesters); polyanhydrides; poly(phosphazenes); poly(hydroxyalkanoates); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), poly(alkylene glycols) such as polyethylene glycol (PEG), poly(propylene glycol) (PPG), and copolymers of ethylene glycol and propylene glycol, poly(oxyethylated polyol), poly(olefinic alcohol), polyvinylpyrrolidone), poly(hydroxy alkylmethacrylamide), poly(hydroxyalkylmethacrylate), poly(saccharides), poly(vinyl alcohol), as well as blends and copolymers thereof. Techniques for preparing suitable polymeric nanoparticles are known in the art, and include solvent evaporation, hot melt particle formation, solvent removal, spray drying, phase inversion, coacervation, and low temperature casting. In some cases, the mitochondrial targeting agents are polypeptides that are covalently linked to the surface of the nanoparticle after particle formulation. In other cases, the mitochondrial targeting agents are lipophilic cations that are covalently bound to the particle surface. In some cases, a cationic polymer is incorporated into the particle to target the particle to the mitochondrion.

Polynucleotide-binding polypeptides can also be targeted to the mitochondria using lipid rafts or other synthetic vesicle compositions. See, for example, U.S. Patent Application Publication No. US 2007/0275924 to Khan, et al., which is specifically incorporated by reference herein in its entirety. The lipid raft compositions can include cholesterol, and one or more lipids selected from the group consisting of sphingomylein, gangliosides, phosphatidylethanolamine, phosphatidylserine, phosphatidylcholine, phosphatidylinositol, and a mitochondrial targeting agent. In certain embodiments, a polypeptide targeting agent is inserted into the lipid raft to target the raft to the mitochondria. The lipid rafts can be prepared and loaded with one or more polynucleotide-binding polypeptides using methods known in the art. See, for example, U.S. Pat. No. 6,156,337 to Barenholz, et al.

A preferred polynucleotide-binding polypeptide that targets mitochondria has at least 80, 85, 90, 95, 99 or 100 percent sequence identity to MARRRRRRRR RRRMAFLRSM WGVLSALGRS GAELCTGCGS RLRSPFSFVY LPRWFSSVLA SCPKKPVSSY LRFSKEQLPI FKAQNPDAKT TELIRRIAQR WRELPDSKKK IYQDAYRAEW QVYKEEISRF KEQLTPSQIM SLEKEIMDKH LKRKAMTKKK ELTLLGKPKR PRSAYNVYVA ERFQEAKGDS PQEKLKTVKE NWKNLSDSEK ELYIQHAKED ETRYHNEMKS WEEQMIEVGR KDLLRRTIKK QRKYGAEEC (SEQ ID NO:22), or SEQ ID NO:22 without the N-terminal methionine ARRRRRRRRR RRMAFLRSMW GVLSALGRSG AELCTGCGSR LRSPFSFVYL PRWFSSVLAS CPKKPVSSYL RFSKEQLPIF KAQNPDAKTT ELIRRIAQRW RELPDSKKKI YQDAYRAEWQ VYKEEISRFK EQLTPSQIMS LEKEIMDKHL KRKAMTKKKE LTLLGKPKRP RSAYNVYVAE RFQEAKGDSP QEKLKTVKEN WKNLSDSEKE LYIQHAKEDE TRYHNEMKSW EEQMIEVGRK DLLRRTIKKQ RKYGAEEC (SEQ ID NO:23).

Another embodiment provides a nucleic acid encoding the polypeptide according to SEQ ID NO:22 is (SEQ ID NO: 24)

```
ATGGCGCGTC GTCGTCGTCG TCGTCGTCGT CGTCGTCGTA
TGGCGTTTCT CCGAAGCATG TGGGGCGTGC TGAGTGCCCT
GGGAAGGTCT GGAGCAGAGC TGTGCACCGG CTGTGGAAGT
CGACTGCGCT CCCCCTTCAG TTTTGTGTAT TTACCGAGGT
GGTTTTCATC TGTCTTGGCA AGTTGTCCAA AGAAACCTGT
AAGTTCTTAC CTTCGATTTT CTAAAGAACA ACTACCCATA
TTTAAAGCTC AGAACCCAGA TGCAAAAACT ACAGAACTAA
TTAGAAGAAT TGCCCAGCGT TGGAGGGAAC TTCCTGATTC
AAAGAAAAAA ATATATCAAG ATGCTTATAG GGCGGAGTGG
CAGGTATATA AAGAAGAGAT AAGCAGATTT AAAGAACAGC
TAACTCCAAG TCAGATTATG TCTTTGGAAA AAGAAATCAT
GGACAAACAT TTAAAAAGGA AAGCTATGAC AAAAAAAAAA
GAGTTAACAC TGCTTGGAAA ACCAAAAAGA CCTCGTTCAG
CTTATAACGT TTATGTAGCT GAAAGATTCC AAGAAGCTAA
GGGTGATTCA CCGCAGGAAA AGCTGAAGAC TGTAAAGGAA
AACTGGAAAA ATCTGTCTGA CTCTGAAAAG GAATTATATA
TTCAGCATGC TAAAGAGGAC GAAACTCGTT ATCATAATGA
```

-continued

```
AATGAAGTCT TGGGAAGAAC AAATGATTGA AGTTGGACGA

AAGGATCTTC TACGTCGCAC AATAAAGAAA CAACGAAAAT

ATGGTGCTGA GGAGTGTTAA.
```

The sequence encoding the protein transduction domain is underlined, and the sequence encoding the mitochondrial localization signal is double underline. Still another embodiment provides a nucleic acid having at least 80, 85, 90, 95, 99 or more percent sequence identity to SEQ ID NO:24

Another preferred polynucleotide-binding polypeptides that targets mitochondria has at least 80, 85, 90, 95, 97, 99, or 100 percent sequence identity to MRRRRRRRRR RRGEGDIMGE WGNEIFGAIA GFLGGEMLSR AVCGTSRQLP PVLGYLGSRQ SSVLASCPKK PVSSYLRFSK EQLPIFKAQN PDAKTTELIR RIAQRWRELP DSKKKIYQDA YRAEWQVYKE EISRFKEQLT PSQIMSLEKE IMDKHLKRKA MTKKKELTLL GKPKRPRSAY NVYVAERFQE AKGDSPQEKL KTVKENWKNL SDSEKELYIQ HAKEDETRYH NEMKSWEEQM IEVGRKDLLR RTIKKQRKYG AEEC (SEQ ID NO:25), or SEQ ID NO:25 without the N-terminal methionine RRRRRRRRRR RGEGDIMGEW GNEIFGAIAG FLGGEMLSRA VCGTSRQLPP VLGYLGSRQS SVLASCPKKP VSSYLRFSKE QLPIFKAQNP DAKTTELIRR IAQRWRELPD SKKKIYQDAY RAEWQVYKEE ISRFKEQLTP SQIMSLEKEI MDKHLKRKAM TKKKELTLLG KPKRPRSAYN VYVAERFQEA KGDSPQEKLK TVKENWKNLS DSEKELYIQH AKEDETRYHN EMKSWEEQMI EVGRKDLLRR TIKKQRKYGA EEC (SEQ ID NO:26)

In another embodiment, the recombinant polypeptide is encoded by a nucleic acid having at least 80, 85, 90, 95, 97, 99, or 100% sequence identity to ATGCGGCGAC GCAGACGTCG TCGTCGGCGG CGTCGCGGCG AGGGTGATAT TATGGGTGAA TGGGGGAACG AAATTTTCGG AGCGATCGCT GGTTTTCTCG GTGGAGAAAT GTTATCACGC GCGGTATGTG GCACCAGCAG GCAGCTGCCT CCAGTCCTTG GCTATCTGGG TTCCCGCCAG TCATCGGTGT TAGCATCATG TCCGAAAAAA CCTGTCTCGT CGTACCTGCG CTTCTCCAAA GAGCAGCTGC CGATTTTTAA AGCGCAAAAT CCGGATGCTA AAACGACTGA ACTGATTCGC CGCATTGCAC AACGCTGGCG CGAACTCCCG GACAGTAAAA AAAAAATTTA TCAGGACGCC TATCGGGCTG AATGGCAGGT CTATAAAGAG GAGATCTCAC GCTTCAAAGA ACAATTAACC CCGAGTCAAA TAATGTCTCT GGAAAAAGAA ATCATGGATA AACACTTAAA ACGAAAGGCG ATGACGAAGA AAAAAGAACT GACCCTGCTA GGTAAACCTA AGCGTCCGCG CTCTGCGTAT AATGTGTACG TGGCAGAACG TTTTCAGGAG GCCAAAGGGG ATTCTCCGCA AGAAAAACTG AAGACCGTCA AAGAAAATTG GAAAAACCTG TCTGATAGCG AAAAAGAACT GTACATTCAG CACGCTAAAG AAGATGAGAC GCGGTATCAC AACGAAATGA AATCTTGGGA AGAGCAGATG ATCGAGGTCG GTCGGAAGGA TCTTCTCCGT CGAACCATCA AAAAACAGCG TAAATATGGA GCAGAAGAGT GCTGA (SEQ ID NO:27).

Preferably the mitochondrial targeting signal, domain, or agent does not permanently damage the mitochondrion, for example the mitochondrial membrane, or otherwise impair mitochondrial function.

ii. Cell Targeting

The proteins of interest disclosed herein can be modified to target a specific cell type or population of cells.

For example, the proteins of interest can be modified with galactosyl-terminating macromolecules to target the polypeptide of interest to the liver or to liver cells. The modified polypeptide of interest selectively enters hepatocytes after interaction of the carrier galactose residues with the asialoglycoprotein receptor present in large amounts and high affinity only on these cells.

In one embodiment, the targeting signal binds to its ligand or receptor which is located on the surface of a target cell such as to bring the composition and cell membranes sufficiently close to each other to allow penetration of the composition into the cell.

In a preferred embodiment, the targeting molecule is selected from the group consisting of an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

Targeting a polypeptide of interest to specific cells can be accomplished by modifying the polypeptide of interest to express specific cell and tissue targeting signals. These sequences target specific cells and tissues. In some embodiments the interaction of the targeting signal with the cell does not occur through a traditional receptor:ligand interaction. The eukaryotic cell comprises a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the proteins of interest described can be altered by changing the targeting signal. In one specific embodiment, compositions are provided that enable the addition of cell surface antigen specific antibodies to the composition for targeting the delivery of polynucleotide-binding polypeptide. Exemplary cell surface antigens are disclosed in Wagner et al., *Adv Gen,* 53:333-354 (2005) which is specifically incorporated by reference herein in its entirety.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used as targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest a. Brain Targeting In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells. Exemplary markers specific for these cell types and states are well known in the art and include, but are not limited to CD133 and Neurosphere.

b. Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include, but are not limited to acetycholine and norepinephrine.

In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7 and MR4.

c. Antibodies

Another embodiment provides an antibody or antigen binding fragment thereof bound to the disclosed proteins of interest acting as the targeting signal. The antibodies or antigen binding fragment thereof are useful for directing the vector to a cell type or cell state. In one embodiment, the polypeptide of interest possesses an antibody binding domain, for example from proteins known to bind antibodies such as Protein A and Protein G from *Staphylococcus aureus*. For example, some embodiments include the amino acids sequence HDEAQQNAFY QVLNMPNLNA DQRNGFIQSL KDDPSQSANV LGEAHDEAQQ NAFYQVLNMP NLNADQRNGF IQSLKDDPSQ SANVLGEA (SEQ ID NO:28) or HDEAQQNAFY QVLNMPNLNA DQRNGFIQSL KDDPSQSANV LGEAHDEAQQ NAFYQVLNMP NLNADQRNGF IQSLKDDPSQ SANVLGEAGE G (SEQ ID NO: 29), both of which include the tandem domain B of Protein A.

In a preferred embodiment, the polynucleotide-binding protein has at least 80, 85, 90, 95, 99, or 100 percent sequence identity to MRRRRRRRRR RRGEGDIMGE WGNEIFGAIA GFLGGEHDEA QQNAFYQVLN MPNLNADQRN GFIQSLKDDP SQSANVLGEA HDEAQQNAFY QVLNMPNLNA DQRNGFIQSL KDDPSQSANV LGEAGEGSSV LASCPKKPVS SYLRFSKEQL PIFKAQNPDA KTTELIRRIA QRWRELPDSK KKIYQDAYRA EWQVYKEEIS RFKEQLTPSQ IMSLEKEIMD KHLKRKAMTK KKELTLLGKP KRPRSAYNVY VAERFQEAKG DSPQEKLKTV KENWKNLSDS EKELYIQHAK EDETRYHNEM KSWEEQMIEV GRKDLLRRTI KKQRKYGAEE C (SEQ ID NO:30), or SEQ ID NO:30 without the N-terminal methionine RRRRRRRRRR RGEGDIMGEW GNEIFGAIAG FLGGEHDEAQ QNAFYQVLNM PNLNADQRNG FIQSLKDDPS QSANVLGEAH DEAQQNAFYQ VLNMPNLNAD QRNGFIQSLK DDPSQSANVL GEAGEGSSVL ASCPKKPVSS YLRFSKEQLP IFKAQNPDAK TTELIRRIAQ RWRELPDSKK KIYQDAYRAE WQVYKEEISR FKEQLTPSQI MSLEKEIMDK HLKRKAMTKK KELTLLGKPK RPRSAYNVYV AERFQEAKGD SPQEKLKTVK ENWKNLSDSE KELYIQHAKE DETRYHNEMK SWEEQMIEVG RKDLLRRTIK KQRKYGAEEC (SEQ ID NO: 31).

Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting domain includes all or part of an antibody that directs the vector to the desired target cell type or cell state. Antibodies can be monoclonal or polyclonal, but are preferably monoclonal. For human gene therapy purposes, antibodies are derived from human genes and are specific for cell surface markers, and are produced to reduce potential immunogenicity to a human host as is known in the art. For example, transgenic mice which contain the entire human immunoglobulin gene cluster are capable of producing "human" antibodies which can be utilized. In one embodiment, fragments of such human antibodies are employed as targeting signals. In a preferred embodiment, single chain antibodies modeled on human antibodies are prepared in prokaryotic culture.

In preferred embodiments the polypeptide of interest is itself a fusion protein. The fusion protein can include, for example, a polynucleotide-binding polypeptide, a protein transduction domain, and optionally one or more targeting signals. A preferred polypeptide of interest is SEQ ID NO:26. Other exemplary fusion proteins containing a mitochondrial transcription factor polypeptide that are suitable for use as a polypeptide of interest are disclosed in U.S. Pat. Nos. 8,039,587, 8,062,891, 8,133,733, and U.S. Published Application Nos. 2009/0123468, 2009/0208478, and 2006/0211647 all of which are specifically incorporated by reference herein in their entireties.

4. Additional Sequences

The fusion protein can optionally include additional sequences or moieties, including, but not limited to linkers and purification tags.

In a preferred embodiment the purification tag is a polypeptide. Polypeptide purification tags are known in the art and include, but are not limited to His tags which typically include six or more, typically consecutive, histidine residues; FLAG tags, which typically include the sequence DYKDDDDK (SEQ ID NO:32); hemagglutinin (HA) for example, YPYDVP (SEQ ID NO:33); MYC tag for example ILKKATAYIL (SEQ ID NO:34) or EQKLISEEDL (SEQ ID NO:35). Methods of using purification tags to facilitate protein purification are known in the art and include, for example, a chromatography step wherein the tag reversibly binds to a chromatography resin.

Purifications tags can be N-terminal or C-terminal to the fusion protein. The purification tags N-terminal to the fusion protein are typically separated from the polypeptide of interest at the time of the cleavage in vivo. Therefore, purification tags N-terminal to the fusion protein can be used to remove the fusion protein from a cellular lysate following expression and extraction of the expression or solubility enhancing amino acid sequence, but cannot be used to remove the polypeptide of interest. Purification tags C-terminal to the fusion protein can be used to remove the polypeptide of interest from a cellular lysate following expression of the fusion protein, but cannot be used to remove the expression or solubility enhancing amino acid sequence. Purification tags that are C-terminal to the expression or solubility enhancing amino acid sequence can be N-terminal to, C-terminal to, or incorporated within the sequence of the polypeptide of interest.

In some embodiments, the fusion protein includes one or more linkers or spacers. In some embodiments the linker or spacer is one or more polypeptides. In some embodiments, the linker includes a glycine-glutamic acid di-amino acid sequence. The linkers can be used to link or connect two domains, regions, or sequences of the fusion protein.

5. Protein Expression

Molecular biology techniques have developed so that therapeutic proteins can be genetically engineered to be expressed by microorganisms. The gram negative bacterium, *Escherichia coli*, is a versatile and valuable organism for the expression of therapeutic proteins. Although many proteins with therapeutic or commercial uses can be produced by recombinant organisms, the yield and quality of the expressed protein are variable due to many factors. For example, heterologous protein expression by genetically engineered organisms can be affected by the size and source of the protein to be expressed, the presence of an affinity tag linked to the protein to be expressed, codon biasing, the strain of the microorganism, the culture conditions of microorganism, and the in vivo degradation of the expressed protein. Some of these problems can be mitigated by fusing the protein of interest to an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

In some embodiments, the compositions disclosed herein include expression or solubility enhancing amino acid sequences. In some embodiments, the expression or solubility enhancing amino acid sequence is cleaved prior administration of the composition to a subject in need thereof. The expression or solubility enhancing amino acid sequence can be cleaved in the recombinant expression system, or after the expressed protein in purified. In some embodiments, the expression or solubility enhancing is a ULP1 or SUMO sequence. Recombinant protein expression systems that incorporate the SUMO protein ("SUMO fusion systems") have been shown to increase efficiency and reduce defective expression of recombinant proteins in *E. coli*., see for example Malakhov, et al., *J. Struct. Funct. Genomics,* 5: 75-86 (2004), U.S. Pat. No. 7,060,461, and U.S. Pat. No. 6,872,551. SUMO fusion systems enhance expression and solubility of certain proteins, including severe acute respiratory syndrome coronavirus (SARS-CoV) 3CL protease, nucleocapsid, and membrane proteins (Zuo et al., *J. Struct. Funct. Genomics,* 6:103-111 (2005)).

Other suitable compositions for use with the disclosed methods include, the novel creatine derivative of Formula IV

IV

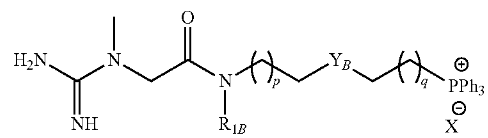

or a pharmaceutically acceptable salt thereof wherein $Y_B$ is —O—, —S—, —O—$(CH_2)_m$—O—, [O—$(CH_2)_m$]$_n$—O—; —N($R_{2B}$)—, —NC(═O)—, —N[C(═O)$Z_B$]—, or

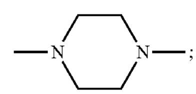

p is 1-4;

q is 1-4;

m is 2-4;

n is 1-4;

$Z_B$ is H, $C_1$-$C_6$alkyl, cycloalkylalkyl, aryl, or heteroaryl;

$R_{1B}$ is H, $C_1$-$C_6$alkyl, or cycloalkylalkyl;

$R_{2B}$ is H, $C_1$-$C_6$alkyl, or cycloalkylalkyl; and

X is pharmaceutically acceptable anion.

Specifically, the present invention provides a compound of formula IV wherein $R_{1B}$ is hydrogen or a methyl.

Specifically, the present invention provides a compound of formula IV wherein p and q is 1.

Specifically, the present invention provides a compound of formula IV wherein $Y_B$ is oxygen or sulfur or nitrogen.

Specifically, the present invention provides compound of formula IV wherein $R_{1B}$ is hydrogen or a methyl.

Specifically, the present invention provides a compound of formula IV wherein $Y_B$ is —O—$(CH_2)_m$—O—; and m is 2 and $R_{1B}$ is hydrogen or methyl.

Specifically, the present invention provides a compound of formula IV wherein $R_{1B}$ is hydrogen or a methyl.

Specifically, the present invention provides a compound of formula IV wherein p and q is 2; and $Y_B$ is oxygen.

Specifically, the present invention provides a compound of formula IV wherein $Y_B$ is nitrogen; $R_{2B}$ is methyl; p and q are 1; and $R_{1B}$ is hydrogen or methyl.

Specifically, the present invention provides a compound of formula IV wherein $Y_B$ is divalent piperidine; p and q are one 1; and $R_{1B}$ is hydrogen or a methyl.

Specifically, the present invention provides a compound of formula IV wherein $Y_B$ is —N[C(═O)$Z_B$]— wherein $Z_B$ is methyl or hydrogen.

Specifically, the present invention provides a compound of formula IV wherein $Y_B$ is —N[C(═O)$Z_B$]—; $Z_B$ is methyl or hydrogen; p and q are 1; and $R_{1B}$ is hydrogen or methyl.

Specifically, the present invention provides a compound of formula IV where $Y_B$is —N[C(═O)$Z_B$]—; $Z_B$ is hydrogen, $C_1$-$C_6$alkyl, or aryl, p is 1 or 2, q is 1 or 2, and $R_{1B}$ is hydrogen or methyl.

Specifically, X is bromide, chloride, trifluoroacetate, acetate, or mesylate.

Specifically, X is chloride or trifluoroacetate.

The compounds of Formula IV are useful for enhancing mitochondrial function, for increasing ATP production in mitochondria, for improving exercise tolerance or stamina, for improving muscle strength or stamina in a diseased or healthy individual.

The compounds of Formula IV are useful for treating or alleviating the conditions referenced above. Additionally, they are useful for improving exercise tolerance or stamina, for improving muscle strength or stamina in a diseased or healthy individual.

The compounds of Formula IV are also useful for treating one or more symptoms of the mitochondrially-related disorder in the patient or for treating one or more symptoms of the creatine deficiency-related disorder in the patient.

In some embodiments, the compound of Formula IV is selected from Table 2.

TABLE 2

| Compound No. | Structure |
| --- | --- |
| B-1 | 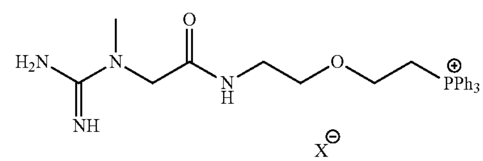 |
| B-2 | 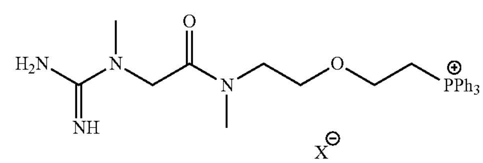 |
| B-3 | 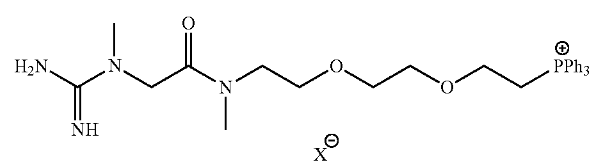 |
| B-4 | 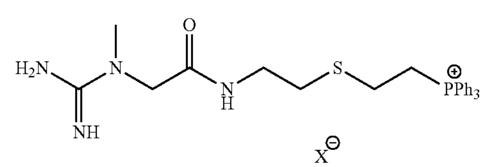 |
| B-5 | 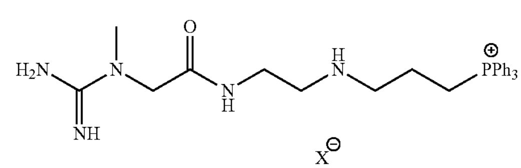 |
| B-6 | 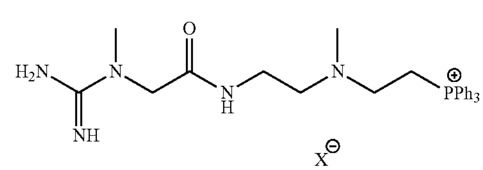 |
| B-7 | 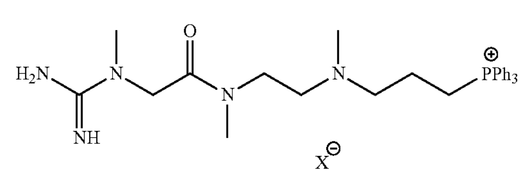 |

TABLE 2-continued

| Compound No. | Structure |
|---|---|
| B-8 | 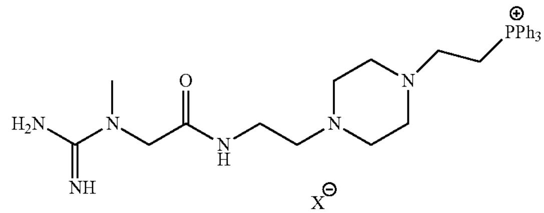 |
| B-9 | 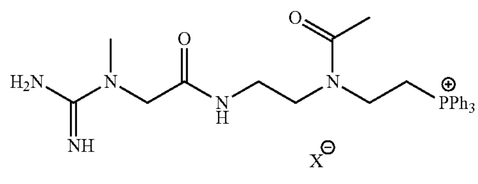 |
| B-10 | 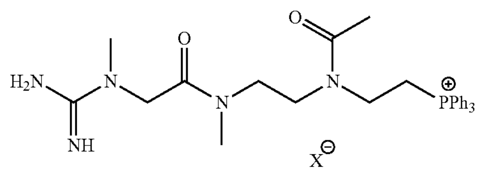 |

Other suitable compositions for use with the disclosed methods include analogs of Formula IV, compounds B-5A and B-1A, or any other pharmaceutically acceptable salt, having the following structures:

B-5

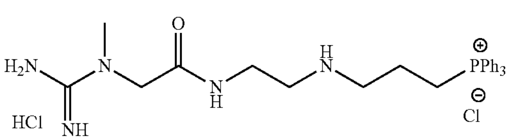

N-(2-((3-(triphenylphosphino)propyl)amino)ethyl)-2-(1-methylguanidino)acetamide dichloride

B-1

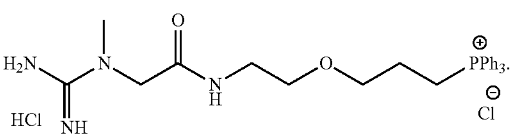

N-(2-(2-(triphenylphosphino)ethoxy)ethyl)-2-(1-methylguanidino)acetamide dichloride Creatine compounds functionalized with one or more mitochondrial targeting agents can be synthesized by reacting creatine or a creatine analog with a lipophilic cation. In some embodiments, the creatine subunit and the mitochondrial targeting agent are covalently connected by a linker.

A number of synthetic methods are useful for the preparation of the compounds of Formula IV. Representative methodologies for the preparation of creatine compounds are discussed in "Advanced Organic Chemistry," 5$^{th}$ Edition, 2001, Wiley-Interscience Publication, New York.

The following reaction schemes illustrate the general synthetic procedures for preparing the compounds of Formula IV including compounds in Table 2. All starting materials are prepared by procedures described in these schemes or by procedures known to one of ordinary skill in the art.

Scheme 1.

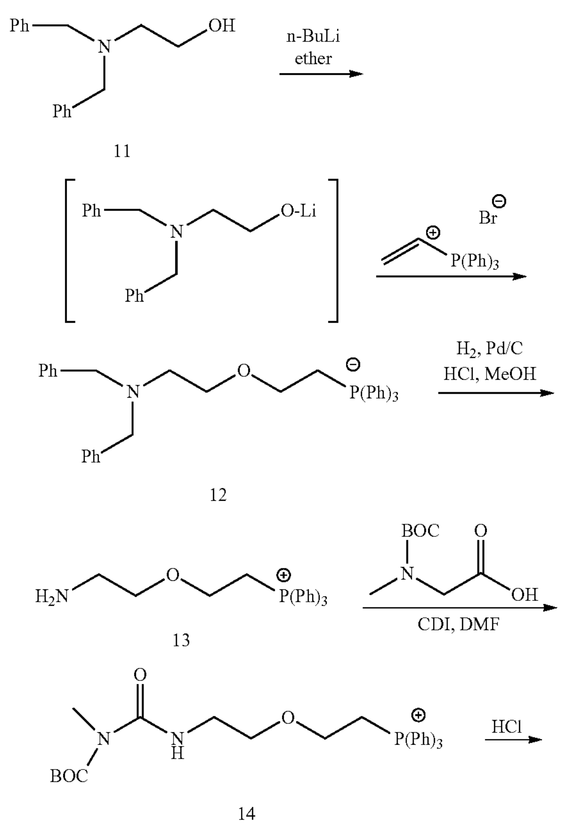

-continued

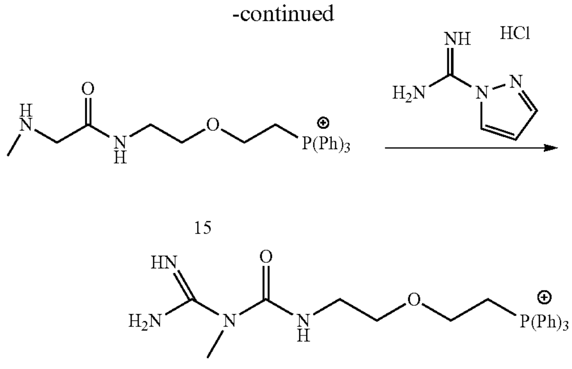

15

B-1

Synthesis of Compound B-1 (Scheme 1)

The procedure described in Synthesis, 301 (1989) was used to prepare amine 13. Aminoalcohol 11 was treated with n-butyllithium to generate the lithium alkoxide which was then added to commercially available vinyltriphosphonium bromide to obtain 12. The two benzyl protecting groups were removed under standard hydrogeneolysis conditions in the presence of acid to afford the primary amine (13). This was coupled with commercially available BOC-protected N-methylglycine using carbonyldiimidazole to afford amide 14 which was treated with dry hydrogen chloride in ethereal solvent to remove the BOC protecting group. The guanidine group was inserted using the commercially available N-pyrazole reagent to afford Compound B-1.

Scheme 2.

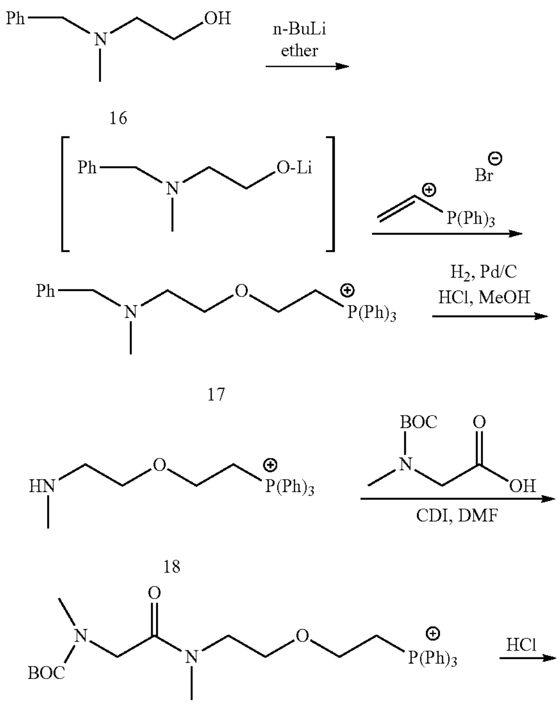

16

17

18

19

-continued

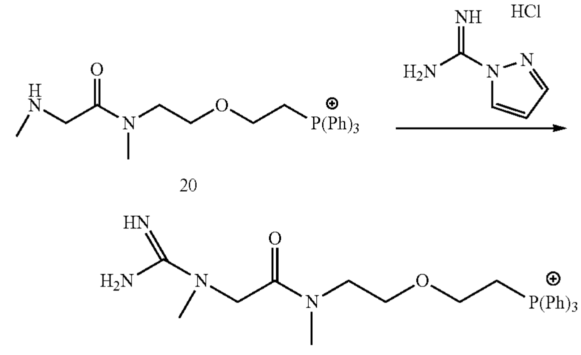

20

B-2

Synthesis of Compound B-2 (Scheme 2)

The procedure described in Synthesis, 301 (1989) was used to prepare amine 18. Aminoalcohol 16 was treated with n-butyllithium to generate the lithium alkoxide which was then added to commercially available vinyltriphosphonium bromide to obtain 17. The benzyl protecting group was removed under standard hydrogeneolysis conditions in the presence of acid to afford the secondary amine (18). This was coupled with commercially available BOC-protected N-methylglycine using carbonyldiimidazole to afford amide 19 which was treated with dry hydrogen chloride in ethereal solvent to remove the BOC protecting group. The guanidine group was inserted using the commercially available N-pyrazole reagent to afford Compound B-2.

Scheme 3.

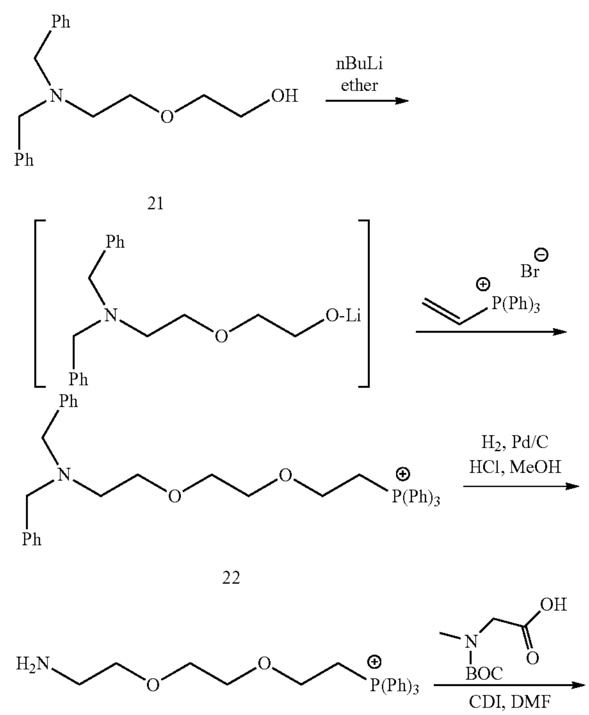

21

22

23

-continued

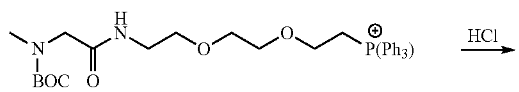

24

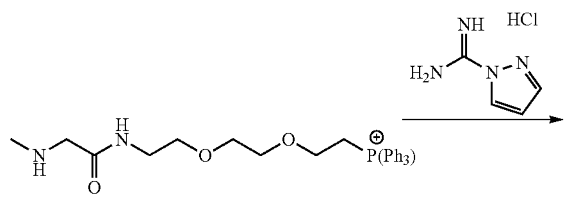

25

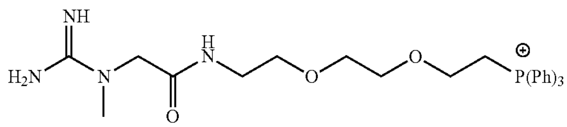

B-3

Synthesis of Compound B-3 (Scheme 3)

The procedure described in Synthesis, 301 (1989) was used to prepare amine 23. Aminoalcohol 21 was treated with n-butyllithium to generate the lithium alkoxide which was then added to commercially available vinyltriphosphonium bromide to obtain 22. The two benzyl protecting groups were removed under standard hydrogeneolysis conditions in the presence of acid to afford the primary amine (23). This was coupled with commercially available BOC-protected N-methylglycine using carbonyldiimidazole to afford amide 24 which was treated with dry hydrogen chloride in ethereal solvent to remove the BOC protecting group. The guanidine group was inserted using the commercially available N-pyrazole reagent to afford Compound B-3.

Scheme 4.

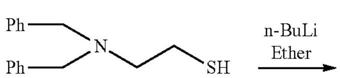

26

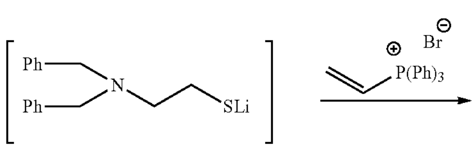

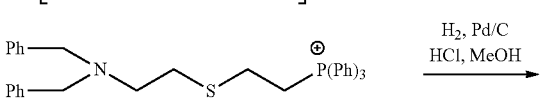

27

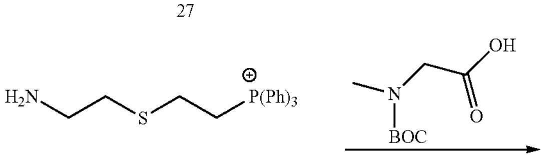

28

-continued

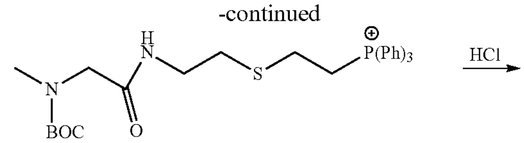

29

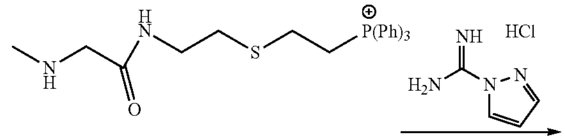

30

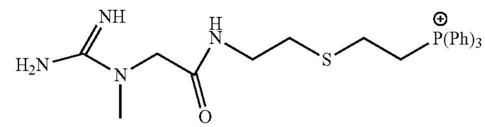

B-4

Synthesis of Compound B-4 (Scheme 4)

Thioamine 26 was treated with n-butyllithium to generate the lithium thioalkoxide which was then added to commercially available vinyltriphosphonium bromide to obtain 27. The two benzyl protecting groups were removed under standard hydrogeneolysis conditions in the presence of acid to afford the primary amine (28). This was coupled with commercially available BOC-protected N-methylglycine using carbonyldiimidazole to afford amide 29 which was treated with dry hydrogen chloride in ethereal solvent to remove the BOC protecting group. The guanidine group was inserted using the commercially available N-pyrazole reagent to afford Compound B-4.

Scheme 5.

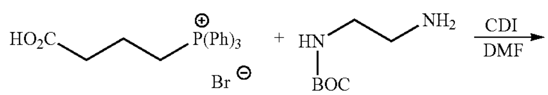

31 32

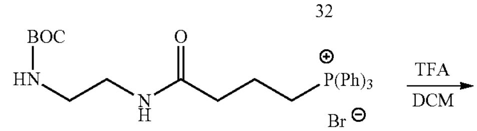

33

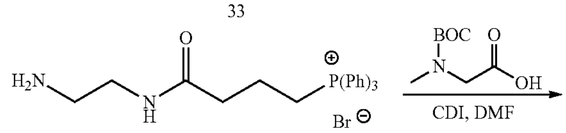

34

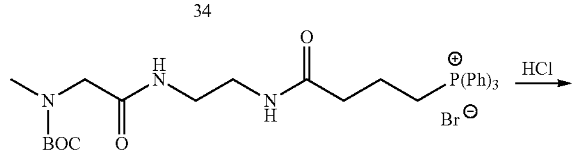

35

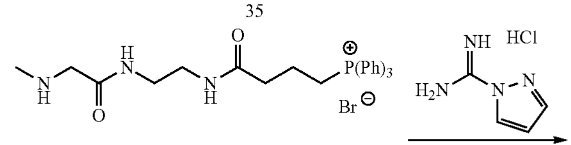

36

-continued

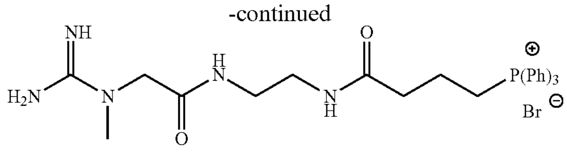

B-5

Synthesis of Compound B-5 (Scheme 5)

Commercially available carboxylic acid 31 was condensed with amine 32 under the influence of carbonyldiimidazole to obtain amide 33. The BOC group was removed using TFA and 34 was converted to amide 35. Dry hydrogen chloride in ethereal solvent was used to deprotect the BOC group to obtain 36, which was then converted to the guanidine compound B-5.

Scheme 6.

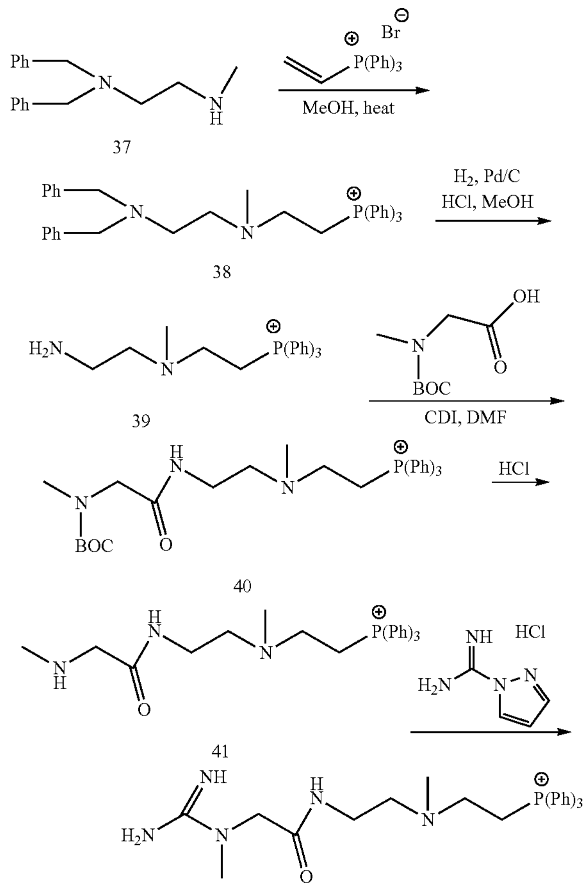

B-6

Synthesis of Compound B-6 (Scheme 6)

Amine 37 was heated in methanol with commercially available vinyltriphenylphosphonium bromide according to the procedure described in *Bull. Chim. Soc. Fr.* 980 (1985) to afford 38. The benzyl groups were removed using standard hydrogenolysis conditions to afford 39. This primary amine was coupled with BOC-protected N-methylglycine to afford amide 40, which was then BOC group was removed using dry hydrogen chloride gas in ethereal solvent. Compound 41 was treated with the commercially available pyrazole reagent to obtain guanidine B-6 using the standard procedure.

Scheme 7.

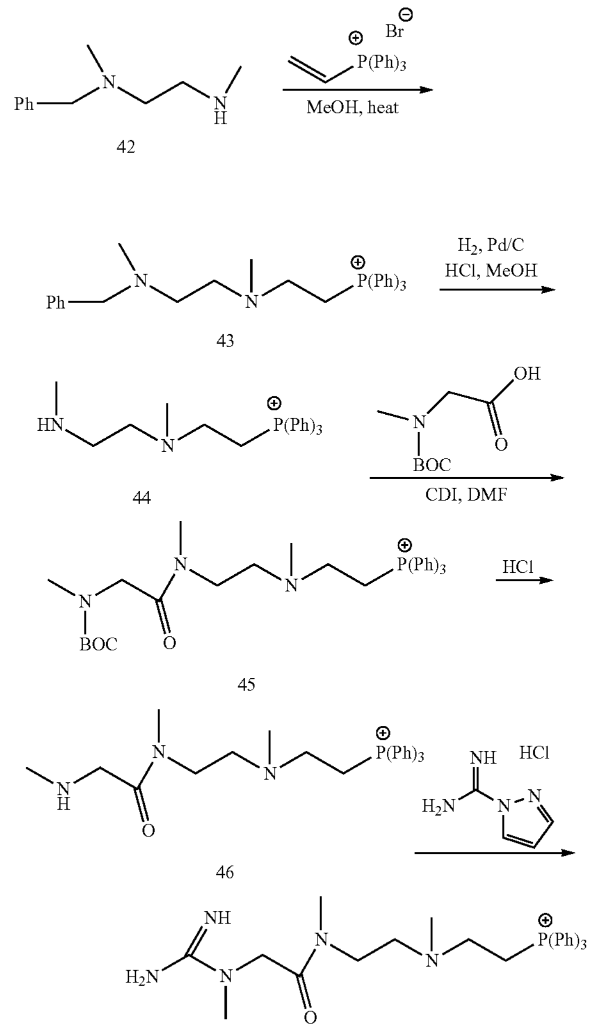

B-7

Synthesis of Compound B-7 (Scheme 7)

Amine 42 was heated in methanol with commercially available vinyltriphenylphosphonium bromide according to the procedure described in *Bull. Chim. Soc. Fr.* 980 (1985) to afford 42. The benzyl group was removed using standard hydrogenolysis conditions to afford 44. This secondary amine was coupled with BOC-protected N-methylglycine to afford amide 45, which was then BOC group was removed using dry hydrogen chloride gas in ethereal solvent. Compound 46 was treated with the commercially available pyrazole reagent to obtain guanidine B-7 using the standard procedure.

Scheme 8

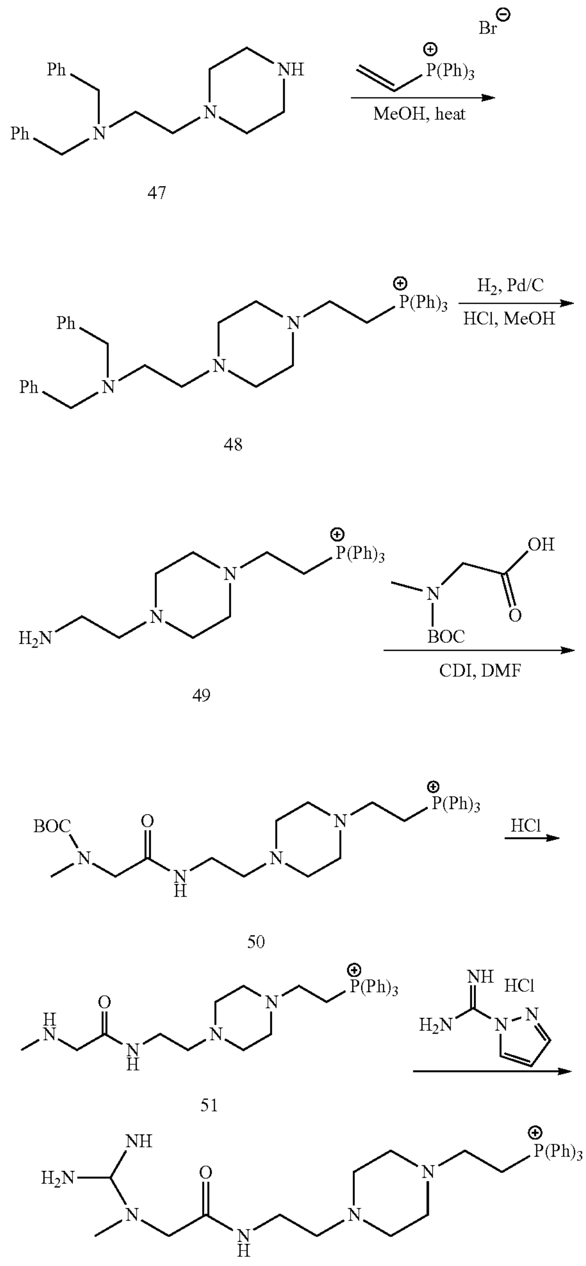

Scheme 9

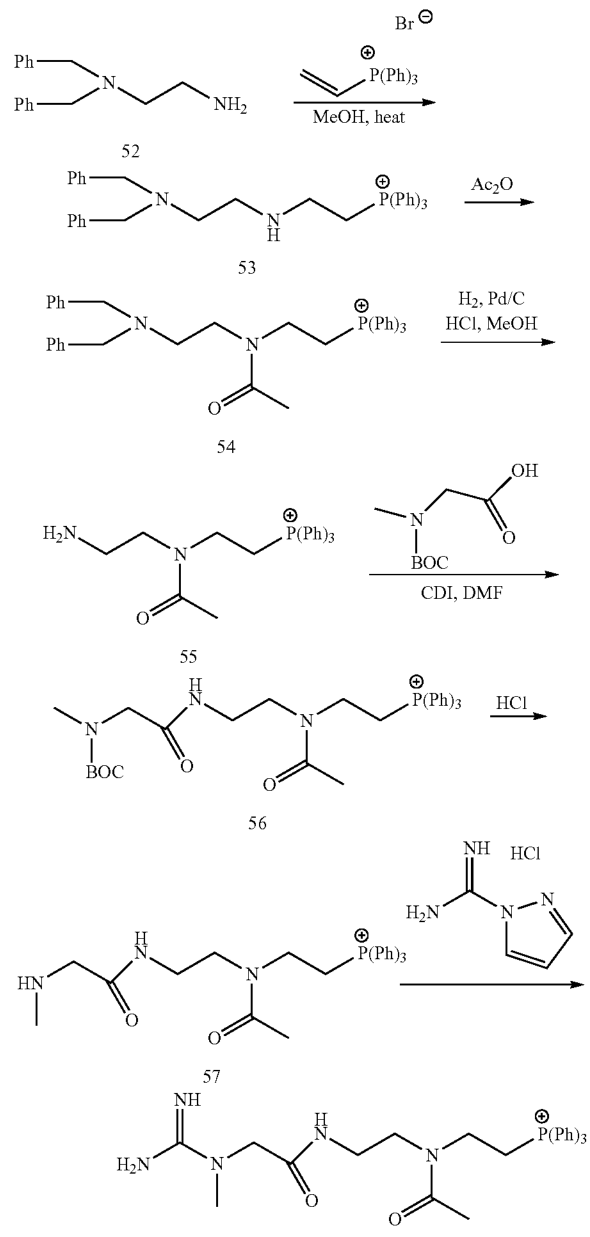

Synthesis of Compound B-8 (Scheme 8)

Amine 47 was heated in methanol with commercially available vinyltriphenylphosphonium bromide according to the procedure described in *Bull. Chim. Soc. Fr.* 980 (1985) to afford 48. The benzyl groups were removed using standard hydrogenolysis conditions to afford 49. This primary amine was coupled with BOC-protected N-methylglycine to afford amide 50, which was then BOC group was removed using dry hydrogen chloride gas in ethereal solvent. Compound 51 was treated with the commercially available pyrazole reagent to obtain guanidine B-8 using the standard procedure.

Synthesis of Compound B-9 (Scheme 9)

Amine 52 was heated in methanol with commercially available vinyltriphenylphosphonium bromide according to the procedure described in *Bull. Chim. Soc. Fr.* 980 (1985) to afford 53. The secondary amine (53) was acylated using acetic anhydride with triethylamine in DCM. The benzyl groups were removed using standard hydrogenolysis conditions to afford 55. This primary amine was coupled with BOC-protected N-methylglycine to afford amide 56, which was then BOC group was removed using dry hydrogen chloride gas in ethereal solvent. Compound 57 was treated with the commercially available pyrazole reagent to obtain guanidine B-9 using the standard procedure.

Scheme 10.

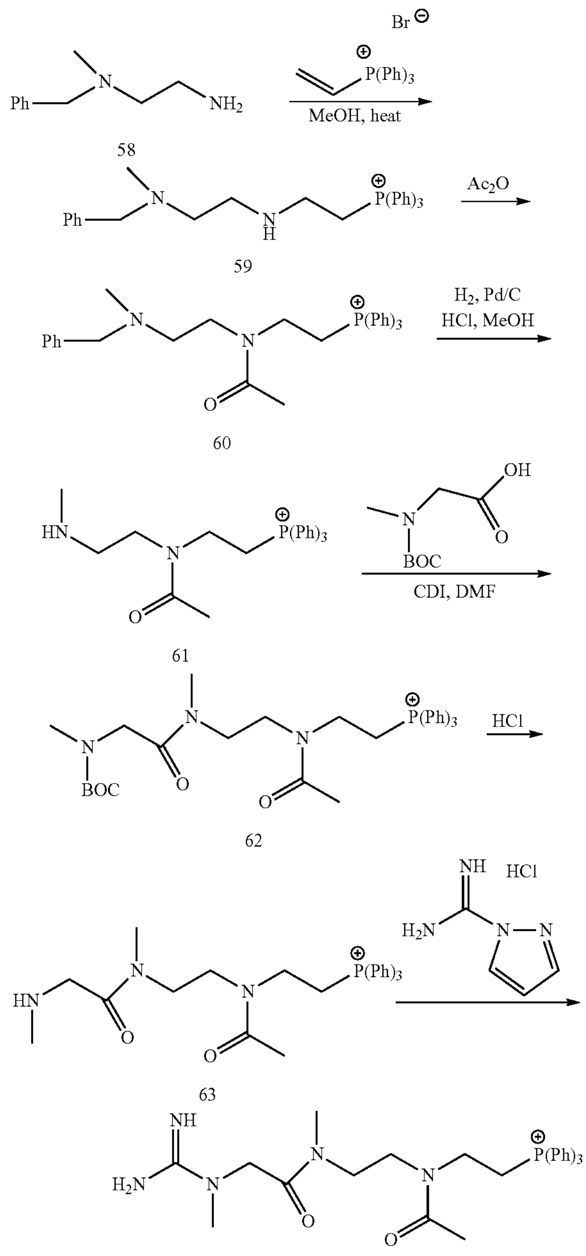

58

59

60

61

62

63

B-10

Synthesis of Compound B-10 (Scheme 10)

Amine 58 was heated in methanol with commercially available vinyltriphenylphosphonium bromide according to the procedure described in *Bull. Chim. Soc. Fr.* 980 (1985) to afford 59. The secondary amine (59) was acylated using acetic anhydride with triethylamine in DCM. The benzyl group was removed using standard hydrogenolysis conditions to afford 61. This secondary amine was coupled with BOC-protected N-methylglycine to afford amide 62, which was then BOC group was removed using dry hydrogen chloride gas in ethereal solvent. Compound 63 was treated with the commercially available pyrazole reagent to obtain guanidine B-10 using the standard procedure.

Preparation of Compound B-1a (Also See Scheme 1) and Compound B-5a (Also See Scheme 5)

B-5

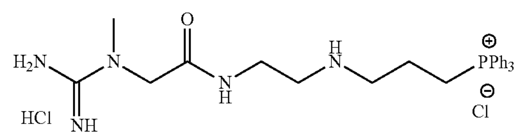

N-(2-((3-(triphenylphosphino)propyl)amino)ethyl)-2-(1-methylguanidino)acetamide dichloride

B-1

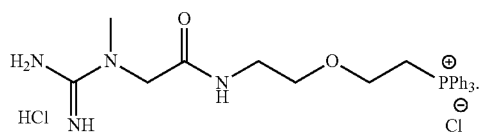

N-(2-(2-(triphenylphosphino)ethoxy)ethyl)-2-(1-methylguanidino)acetamide dichloride Experimental Section Temperatures are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals may be reported. Analytical HPLC performed on an Agilent 1100 HPLC: Agilent XDB C18 50×4.6 mm 1.8 micron column, 1.5 mL/min, Solvent A-Water (0.1% TFA), Solvent B—Acetonitrile (0.07% TFA), Gradient—5 min 95% A to 95% B; 1 min hold; then recycle, UV Detection @ 210 and 254 nm Preparation of Compound B-5A Scheme 1

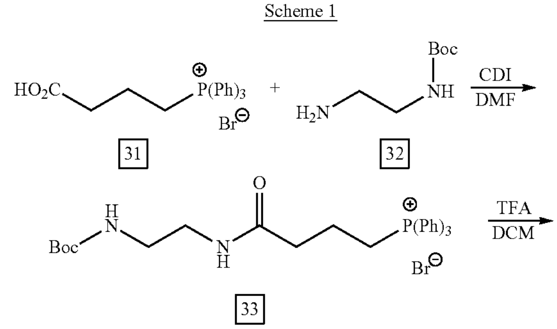

31

32

33

-continued

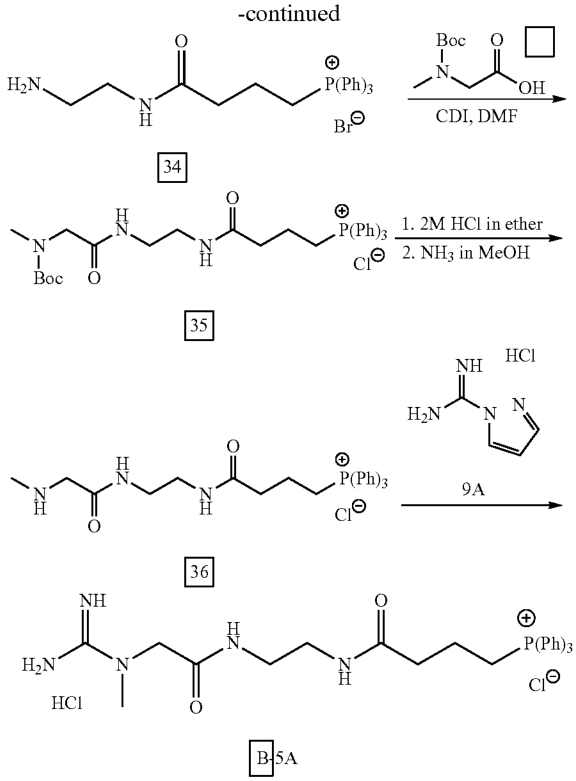

34

35

36

B-5A 12,12-Dimethyl-5,10-dioxo-1,1,1-triphenyl-11-oxa-6,9-diaza-1-phosphoniatridecane bromide (33)

To a well-stirred slurry of (3-carboxypropyl)(triphenyl) phosphonium bromide (2.0 g, 4.6 mmol) in dry DMF (14.7 mL) at room temperature was added solid N,N-carbonyldiimidazole (904 mg, 5.58 mmol). This mixture was allowed to stir at rt for 45 min and N-(2-aminoethyl)(tert-butoxy) carboxamide (0.809 mL, 5.11 mmol) was added via syringe. The reaction was then allowed to stir for 90 min at rt. The mixture was partitioned between ethyl acetate and saturated sodium bicarbonate (100 mL each), the layers were separated and the aqueous layer was extracted with ethyl acetate (3×50 mL). The ethyl acetate was discarded and the aqueous layer was extracted with DCM (4×50 mL). The DCM solution was dried with anhydrous sodium sulfate and concentrated to give 2.25 g (84%) of 12,12-dimethyl-5,10-dioxo-1,1,1-triphenyl-11-oxa-6,9-diaza-1-phosphoniatridecane bromide as a thick oil. $^{1}H$ NMR (300 MHz, $CDCl_3$) δ ppm 1.38 (s, 9H) 1.90-2.08 (m, 2H) 2.75-2.88 (m, 2H) 3.28-3.46 (m, 4H) 3.55-3.75 (m, 2H) 5.85-6.02 (m, 1H) 7.66-7.94 (m, 15H) 8.23-8.38 (m, 1H); HPLC Retention Time: 3.36 min MS (ESI+) for $C_{29}H_{36}N_2O_3P$ m/z 491.2 (M)+.

{4-[(2-Aminoethyl)amino]-4-oxobutyl}(triphenyl) phosphonium bromide (34)

To a cold (at 0° C.) well-stirred solution of 12,12-dimethyl-5,10-dioxo-1,1,1-triphenyl-11-oxa-6,9-diaza-1-phosphoniatridecane bromide (1.54 g, 2.69 mmol) in DCM (23 mL) was added TFA (5.7 mL, 74 mmol). The reaction was stirred at 0° C. for 30 min and allowed to warm to rt. After 90 min (total reaction time) the reaction was concentrated. The residue was partitioned between DCM and 5% sodium carbonate (50 mL each), the layers were separated and the aqueous layer was repeatedly extracted with DCM (6×50 mL). The organics were combined, dried with anhydrous sodium sulfate and concentrated to give 110 mg of the product as an oil. The aqueous was then lyophilized and the salts extracted with DCM (100 mL) to give 1.1 g of the crude product as a foam. The materials were combined to give 1.2 g (94%) of {4-R2-aminoethyl)aminol-4-oxobutyl}(triphenyl)phosphonium bromide that did not require further purification. $^{1}H$ NMR (300 MHz, $CDCl_3$) δ ppm 1.85-2.00 (m, 2H) 2.47-2.61 (m, 2H) 3.16-3.26 (m, 2H) 3.40-3.49 (m, 2H) 3.55-3.67 (m, 2H) 7.57-7.90 (m, 15H) 8.67-8.76 (m, 1H); HPLC Retention Time: 2.44 min MS (ESI+) for $C_{24}H_{28}N_2OP$ m/z 391.1 (M)+.

$N^2$-(tert-Butoxycarbonyl)-$N^2$-methyl-N-(2-{[4-(triphenylphosphonio)butanoyl]-amino}ethyl)glycinamide chloride (35)

To a well-stirred solution of N-tert-butoxycarbonylsarcosine (0.578 g, 3.05 mmol) in dry DMF (12 mL) under nitrogen at rt was added N,N-carbonyldiimidazole (0.516 g, 3.18 mmol) as a solid. The reaction was allowed to stir at rt for 1 h and a solution of {4-[(2-aminoethyl)amino]-4-oxobutyl}(triphenyl)phosphonium bromide (1.20 g, 2.54 mmol) in dry DMF (3 mL) was added. This mixture was then allowed to stir at rt overnight. The reaction was partitioned between DCM and 10% aqueous lithium chloride solution (30 mL each), the layers were separated and the aqueous layer was extracted with DCM (4×30 mL). The organics were combined, dried with anhydrous sodium sulfate and concentrated. The residue was subjected to silica gel chromatography (BDH, 230-400 mesh, 100 g, elution with 0, 5, 10 and 20% MeOH/DCM) to give 604 mg (36%) of $N^2$-(tert-butoxycarbonyl)-$N^2$-methyl-N-(2-{[4-(triphenylphosphonio)butanoyl]amino}ethyl)-glycinamide chloride as an oil. $^{1}H$ NMR (300 MHz, $CDCl_3$) δ ppm 1.43 (s, 9H) 1.83-2.10 (m, 2H) 2.62-2.80 (m, 2H) 2.88 (s, 3H) 3.34-3.62 (m, 6H) 3.99 (s, 2H) 7.62-7.89 (m, 15H) 8.15-8.25 (m, 1H) 8.70-8.96 (m, 1H); HPLC Retention Time: 3.24 min MS (ESI+) for $C_{32}H_{41}N_3O_4P$ m/z 562.2 (M)+.

$N^2$-Methyl-N-(2-{[4-(triphenylphosphonio)butanoyl] amino}ethyl)glycinamide chloride (36)

To a well-stirred solution of $N^2$-(tert-butoxycarbonyl)-$N^2$-methyl-N-(2-{[4-(triphenylphosphonio)butanoyl] amino}ethyl)-glycinamide chloride (604 mg, 0.940 mmol) in DCM (5.0 mL) at 0° C. under nitrogen was added 2.0 M of HCl in ether (2.0 mL, 4.0 mmol). The reaction was allowed to warm to rt and stir for 3 days. The reaction was concentrated to remove residual HCl and re-dissolved in DCM (5 mL). To this solution was added 7.0 M ammonia in methanol (0.400 mL, 2.82 mmol) and the mixture stirred at rt for 2 hours. The precipitate that had formed was filtered and washed with DCM (3×5 mL). The filtrate was concentrated to give 332 mg (70%) of $N^2$-methyl-N-(2-{[4-(triphenylphosphonio)butanoyl]amino}ethyl)glycinamide chloride as a foam. $^{1}H$ NMR (400 MHz, DMSO-$d_6$) δ ppm 1.65-1.81 (m, 2H) 2.21 (s, 3H) 2.27-2.36 (m, 2H) 3.01 (s, 2H) 3.06-3.21 (m, 4H) 3.46-3.62 (m, 2H) 7.73-7.96 (m, 15H) 8.01-8.10 (m, 1H); HPLC Retention Time: 2.47 min MS (ESI+) for $C_{27}H_{33}N_3O_2P$ m/z 462.0 (M)+.

$N^2$-[Amino(imino)methyl]-$N^2$-methyl-N-(2-{[4-(triphenylphosphonio)butanoyl]-amino}ethyl)-glycinamide chloride hydrochloride (B-5)

To a well-stirred solution of $N^2$-methyl-N-(2-{[4-(triphenylphosphonio)butanoyl]amino}ethyl)glycinamide chloride (335 mg, 0.673 mmol) and 1H-pyrazole-1-carboximidamide hydrochloride (0.104 g, 0.706 mmol) in dry DMF (4.0 mL) at rt under nitrogen was added N,N-diisopropylethylamine (117 μL, 0.673 mmol) via syringe. The reaction was allowed to stir at rt for 18 h and an additional aliquot of both 1H-pyrazole-1-carboximidamide hydrochloride (49.3 mg, 0.336 mmol) and N,N-diisopropylethylamine (58.6 μL, 0.336 mmol) were added. Stirring at rt was continued for an additional 24 h. The reaction mixture was diluted with DCM (40 mL) and allowed to stand overnight. The product precipitated and was isolated by filtration to give 35 mg (9%) of $N^2$-[amino(imino)methyl]-$N^2$-methyl-N-(2-{[4-(triphenylphosphonio)butanoyl]amino}ethyl)glycinamide chloride hydrochloride. $^1H$ NMR (400 MHz, DMSO-$d_6$) δ ppm 1.65-1.79 (m, 2H) 2.27-2.39 (m, 2H) 2.88 (s, 3H) 3.08-3.17 (m, 4H) 3.49-3.60 (m, 2H) 4.00 (s, 2H) 7.41 (s, 4H) 7.70-7.95 (m, 15H) 8.14-8.21 (m, 1H) 8.21-8.28 (m, 1H); HPLC Retention Time: 2.53 min MS (ESI+) for $C_{28}H_{35}N_5O_2P$ m/z 504.1 (M)+.

Preparation of Compound B-1A

Scheme 2

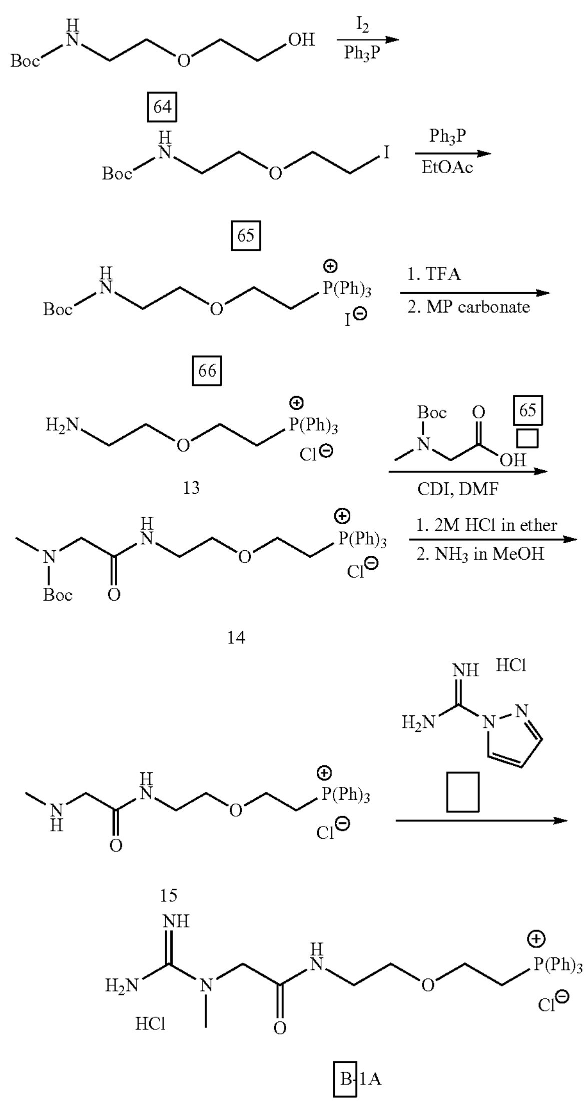

tert-Butyl[2-(2-iodoethoxy)ethyl]carbamate (65)

To a cold (at 0° C.) well-stirred solution of tert-butyl[2-(2-hydroxyethoxy)ethyl]carbamate (2.50 g, 12.2 mmol), triphenylphosphine (3.82 g, 14.6 mmol) and imidazole (0.99 g, 14 mmol) in DCM (50 mL) under nitrogen was added solid iodine (3.39 g, 13.4 mmol). The iodine slowly dissolved leaving a milky yellow suspension. The ice bath was removed and the reaction allowed to warm to rt and stir overnight. The reaction was partitioned between ethyl acetate and 10% sodium thiosulfate solution (100 mL each), the layers were separated and the aqueous layer was extracted with ethyl acetate (3×50 mL). The organics were combined, washed with saturated sodium bicarbonate and brine, dried with anhydrous sodium sulfate and concentrated. The residue was subjected to silica gel chromatography (BDH, 230-400 mesh, 200 g, elution with 0, 5, 10, 15 and 20% ethyl acetate/hexane) to give 3.69 g (96%) of tert-butyl[2-(2-iodoethoxy)ethyl]carbamate as a clear colorless oil. $^1H$ NMR (300 MHz, $CDCl_3$) δ ppm 1.45 (s, 9H) 3.23-3.30 (m, 2H) 3.30-3.40 (m, 2H) 3.52-3.60 (m, 2H) 3.68-3.77 (m, 2H) 4.94 (br. s., 1H); HPLC Retention Time: 3.56 min MS (ESI+) for $C_9H_{18}INO_3$ m/z 337.9 (M+Na)+.

10,10-Dimethyl-8-oxo-1,1,1-triphenyl-4,9-dioxa-7-aza-1-phosphoniaundecane iodide (66)

To a well-stirred solution of tert-butyl[2-(2-iodoethoxy)ethyl]carbamate (3.69 g, 11.7 mmol) in ethyl acetate (60 mL) was added triphenylphosphine (3.378 g, 12.88 mmol). The reaction was brought to reflux under nitrogen for 72 h. The reaction mixture was cooled to rt, and the product crystallized on standing. The solid was collected, washed with ethyl acetate and air dried to give 4.97 g (73%) of 10,10-dimethyl-8-oxo-1,1,1-triphenyl-4,9-dioxa-7-aza-1-phosphoniaundecane iodide as a white solid. 1H NMR (300 MHz, DMSO-$d_6$) δ ppm 1.35 (s, 9H) 2.77-2.87 (m, 2H) 3.08-3.18 (m, 2H) 3.59-3.75 (m, 2H) 3.84-3.96 (m, 2H) 6.48-6.59 (m, 1H) 7.69-7.95 (m, 15H); HPLC Retention Time: 3.63 min MS (ESI+) for $C_{27}H_{33}NO_3P$ m/z 450.0 (M)+.

[2-(2-aminoethoxy)ethyl](triphenyl)phosphonium iodide (13)

To a cold (at 0° C.) well-stirred solution of 10,10-dimethyl-8-oxo-1,1,1-triphenyl-4,9-dioxa-7-aza-1-phosphoniaundecane iodide (0.450 g, 0.779 mmol) in DCM (8.0 mL) was added TFA (2.0 mL, 26 mmol). The reaction was allowed to warm to rt and stir for 3 h. The reaction was concentrated in vacuo to remove residual TFA and re-suspended in DCM (10 mL). MP carbonate resin (Aldrich, 300 mg) was added and the mixture stirred for 5 h at rt. The reaction was filtered and concentrated to give 350 mg (94%) of [2-(2-aminoethoxy)ethyl](triphenyl)phosphonium iodide as an oil. 1H NMR (400 MHz, $CDCl_3$) δ ppm 2.98-3.10 (m, 4H) 3.17-3.35 (m, 4H) 3.44-3.67 (m, 4H) 3.68-3.92 (m, 4H) 7.38-8.11 (m, 15H); HPLC Retention Time: 2.41 min MS (ESI+) for $C_{22}H_{25}NOP$ m/z 350.1 (M)+.

$N^2$-(tert-butoxycarbonyl)-$N^2$-methyl-N-{2-[2-(triphenylphosphonio)ethoxy]ethyl}glycinamide iodide (14)

To a well-stirred solution of N-tert-butoxycarbonylsarcosine (0.242 g, 1.28 mmol in dry DMF (5.0 mL) under nitrogen at 0° C. was added N,N-carbonyldiimidazole (0.216 g, 1.34 mmol). The reaction was allowed to warm to rt, stir for 90 min and a solution of [2-(2-aminoethoxy)ethyl](triphenyl)phosphonium iodide (0.510 g, 1.07 mmol) in dry DMF (3 mL) was added. Stirring at rt was continued overnight. The reaction was concentrated in vacuo to remove a significant fraction of the solvent and partitioned between DCM and 10% LiCl (50 mL each). The layers were separated and the aqueous layer was extracted with DCM (3×50 mL). The organics were combined, dried with anhydrous sodium sulfate and concentrated. The residue was subjected to silica gel chromatography (BDH, 230-400 mesh, 30 g, elution with DCM then 5 and 10% MeOH/DCM) to give 554 mg (80%) of $N^2$-(tert-butoxycarbonyl)-$N^2$-methyl-N-{2-[2-(triphenylphosphonio)ethoxy]ethyl}glycinamide iodide as a thick oil. HPLC Retention Time: 3.41 min MS (ESI+) for $C_{30}H_{38}N_2O_4P$ m/z 521.0 (M)+.

$N^2$-methyl-N-{2-[2-(triphenylphosphonio)ethoxy]ethyl}glycinamide chloride (15)

To a well-stirred solution of $N^2$-(tert-butoxycarbonyl)-$N^2$-methyl-N-{2-[2-(triphenylphosphonio)ethoxy]ethyl}glycinamide iodide (0.550 g, 0.848 mmol) in DCM (5.0 mL) at 0° C. under nitrogen was added 1.0 M of hydrogen chloride in ether (3.39 mL, 3.39 mmol). The ice bath was removed and the reaction allowed to warm to rt and stir for 48 h. The reaction was concentrated to remove residual HCl and re-suspended in DCM (10 mL). 7M Ammonia in methanol (4 mL) was added and the mixture stirred at rt for 4 h. The slurry was filtered, the solids washed with DCM (5 mL) and the filtrate concentrated to give 450 mg (98%) of $N^2$-methyl-N-{2-[2-(triphenylphosphonio)ethoxy}-ethyl]glycinamide chloride as an oil. HPLC Retention Time: 2.45 min. MS (ESI+) for $C_{25}H_{30}N_2O_2P$ m/z 421.0 (M)+.

$N^2$-[Amino(imino)methyl]-$N^2$-methyl-N-{2-[2-(triphenylphosphonio)ethoxy]ethyl}glycinamide chloride hydrochloride (1)

To a well-stirred solution of $N^2$-methyl-N-{2-[2-(triphenylphosphonio)ethoxy]-ethyl}glycinamide chloride (0.350 g, 0.766 mmol) 1H-pyrazole-1-carboximidamide hydrochloride (0.118 g, 0.804 mmol) in DMF (3.0 mL,) at rt under nitrogen was added N,N-diisopropylethylamine (140 μL, 0.804 mmol) via syringe. The reaction was allowed to stir at rt for 72 h and concentrated in vacuo. The residue was subjected to preparative reverse-phase chromatography: Combiflash, Biotage 40 g C18 AQ column, gradient: from 0 to 80% acetonitrile/water with 0.1% TFA; UV Detection @ 210 nm. The fractions containing purified product were lyophilized to provide 171 mg of the trifluoroacetic acid salt as the trifluoroacetate. This material was dissolved in DCM (10 mL), treated with 1M HCl in ether (2 mL) and concentrated. This process was repeated four times. The resulting product was dissolved in water and lyophilized to give 137 mg (33%) of $N^2$-[amino(imino)methyl]-$N^2$-methyl-N-{2-[2-(triphenylphosphonio)ethoxy]ethyl}glycinamide chloride hydrochloride as an amorphous white solid. 1H NMR (400 MHz, DMSO-$d_6$) 2.85 (s, 3H) 2.92-3.03 (m, 2H) 3.11-3.24 (m, 2H) 3.65-3.70 (m, 1H) 3.70-3.75 (m, 1H) 3.87-4.02 (m, 4H) 7.31 (s, 4H) 7.69-7.95 (m, 15H) 8.00-8.11 (m, 1H); HPLC Retention Time: 2.53 min. MS (ESI+) for $C_{26}H_{32}N_4O_2P$ m/z 462.9 (M)+.

V. Biological Activities and Experimental Procedures

In the following experiments, Mitocreatine dichloride (A-4) was used.

Example 1: Cellular Senescence Assay

Normal primary cells proliferate in culture for a limited number of population doublings prior to undergoing terminal growth arrest and acquiring a senescent phenotype. This finite life span correlates with the age of the organism and with the life expectancy of the species from which the cells were obtained; such that the older the age or the shorter the life span, the less the ability of the cells to undergo population doubling. Senescent cells are characterized by an irreversible G1 growth arrest involving the repression of genes that drive cell cycle progression and the up-regulation of cell cycle inhibitors like p16INK4a, p53, and its transcriptional target, p21CIP1. They are resistant to mitogen-induced proliferation, and assume a characteristic enlarged, flattened morphology. Research into the pathways that positively regulate senescence and ways cells bypass senescence is therefore critical in understanding carcinogenesis. Normal cells have several mechanisms in place to protect against uncontrolled proliferation and tumor genesis.

Senescent cells show common biochemical markers such as expression of an acidic senescence-associated β-galactosidase (SA-β-Gal) activity. While senescence has been characterized primarily in cultured cells, there is also evidence that it occurs in vivo. Cells expressing markers of senescence such as SA-β-Gal have been identified in normal tissues. To determine whether modified Mitocreatine analogues may influence the scenesence in aged fibroblasts, a 96-well Cellular Senescence Assay (SA-β-Gal Fluorometric Format) Cat # CBA-231 Cell Biolabs, Inc. was employed and buffers referenced were supplied by the manufacturer and in some cases freshly prepared prior to usage according to the manufacturer's instructions.

The cells utilized were Human Skin Fibroblast acquired from Coriell Cell Repository. The cell line AG11073 is untransformed human skin fibroblasts from a 75 years old Caucasian male. The primary culture was initiated from explants of a 2 mm-punch biopsy. The cell line AG16409 was untransformed human skin fibroblasts from a 12 years old Caucasian male.

Cells were grown in a 96 well plate. The media was removed and the cells were washed twice with ice cold PBS. 100 μL of cold 1× Cell Lysis Buffer was added to the cells and incubated at 4° C. for 5 minutes. The whole lysate was transferred to a micro-centrifuge tube and spun down at 10 minutes at 4° C. The supernatant was collected as cell lysate. The total protein concentration of each cell lysate sample was assayed by BCA protein Assay and the fluorescent results were normalized to the amount of protein in each well. 50 μL of the cell lysate was transferred to a 96-well plate and 50 μL of freshly prepared 2× Assay Buffer was added. The plate was incubated at 37° C. in the dark for 1-3 hours.

50 μL, of the reaction mixture was removed to a 96-well plate suitable for fluorescence measurement. The reaction was stopped by adding 200 μL of Stop solution and fluorescence was measured with a fluorescence plate reader (PHERA Star FS from BMG Labtech) at 360 nm (Excitation)/465 nm (Emission).

Results are shown in FIG. 1. Cells from the aged individual exhibited a statistically significant decrease of β-galactosidase expression after treatment with Mitocreatine. The cells from the young individual also showed a decrease, although this decrease failed to reach statistical significance.

Treatment of skin fibroblasts with Mitocreatine retards senescence as assessed by levels of β-galactosidase activity. This is significant in aged fibroblasts in increasing concentrations starting at 5 nM to 200 nM Mitocreatine ($p<0.01$ for 5-100 nM, $p<0.05$ for 200 nM). There is a statistically insignificant decrease in β-galactosidase activity with increasing Mitocreatine concentration in young skin fibroblasts. From these results it can be concluded that Mitocreatine would be an effective agent in treating skin with the aging phenotype.

Example 2: Analysis of Oxygen Consumption Rate (OCR)

The effect of Table-1 and Table-2 compounds of interest on the oxygen consumption rate (OCR) of cells was used to determine the ability of the compounds to alter mitochondrial activity and function.

Example 2a: Analysis of OCR for Mitocreatine and Compound A-1

In this assay, an XF24 extracellular flux analyzer (Seahorse Bioscience, North Billerica, Mass.) was used to measure mitochondrial oxygen consumption in intact cells. The XF24 analyzer creates a transient 7 μL chamber in specialized microplates that allows determination of oxygen and proton concentrations in real time through the measurement of oxygen sensitive dyes by the XF24 instrument. 24 hours prior to OCR measurement, fibroblasts were seeded into 20 wells of the 24 well tissue culture plate while 1 ml of XF Calibrant solution (Seahorse Bioscience, North Billerica, Mass.) was added to each well of a 24 well dual-analyte sensor cartridge (Seahorse Bioscience, North Billerica, Mass.). The sensor cartridge repositioned on the 24 well calibration plate, and the plate was incubated overnight at 37° C. without additional $CO_2$.

On the day of the experiment, the injection ports on the sensor cartridge were loaded with compound A-1 or creatine as indicated at 10× concentrations and placed into the XF24 Flux Analyzer for automated calibration. During the sensor calibration, cells in each of the tissue culture well were rinsed once in 1 mL of unbuffered media. 675 μL of unbuffered media was then added to each well, and the plate was incubated for an hour in the absence of additional $CO_2$. Plates were subsequently placed into the calibrated seahorse XF24 flux analyzer for bioenergetic analysis. An equivalent number of cells per well were plated using a cell counter. Further normalization was achieved by taking baseline measurements of OCR on a well-by-well basis, and the increase observed is a comparison to the same well prior to treatment. Thus each well serves as its own control.

Figure 2:
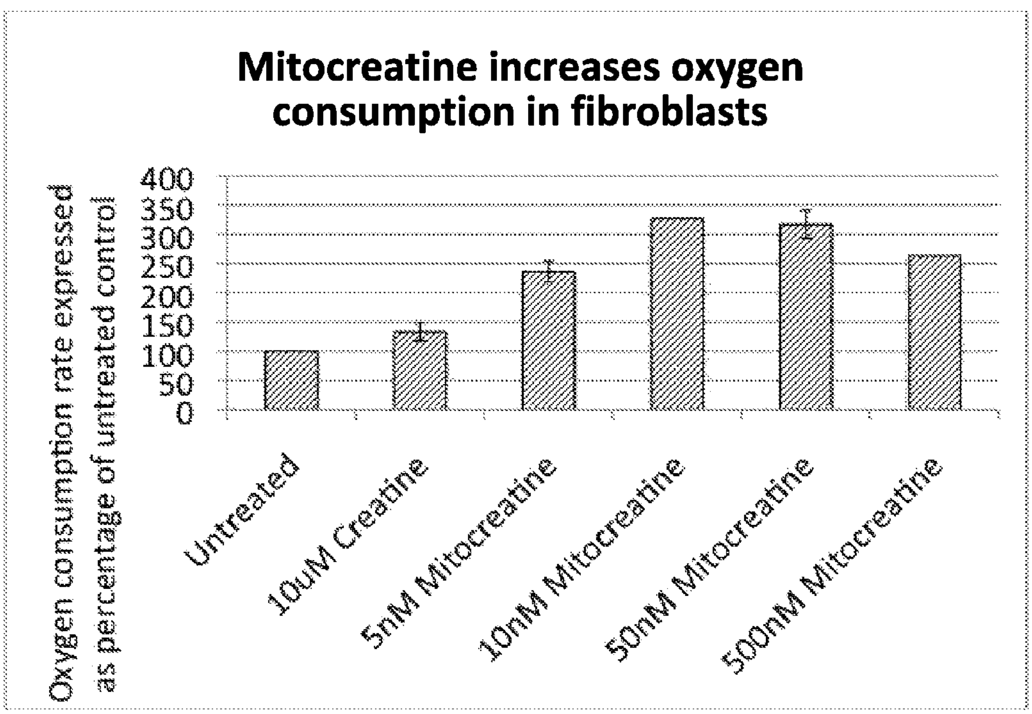
FIG. 2 depicts a bar graph showing the percent increase in oxygen consumption rate (% OCR) upon addition of 10 μM unmodified creatine and Mitocreatine to fibroblasts at various concentrations.

The results of the assay for Mitocreatine at 5 nM, 10 nM, 50 nM, and 500 nM concentrations are shown in FIG. 2 as a percent change from the untreated control. For comparison, the results obtained Mitocreatine were compared with the percent increase in oxygen consumption rate measured upon addition of 10 μM creatine. Mitocreatine at increasing concentrations from 5 nM to 500 nM caused a significant increase in oxygen consumption rate within thirty minutes of treatment compared to unmodified creatine.

Figure 3:
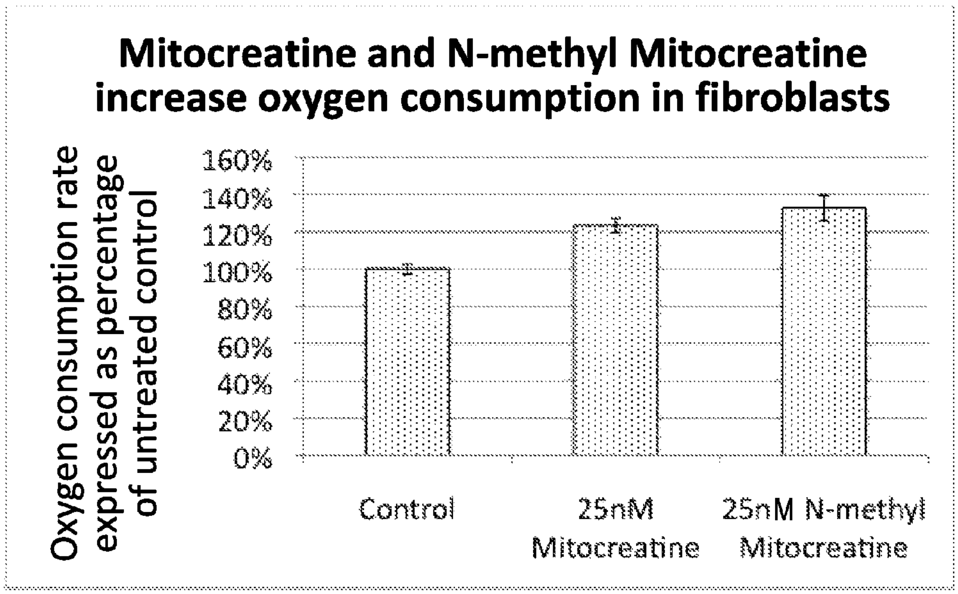
FIG. 3 depicts a bar graph showing the percent increase in oxygen consumption rate (% OCR) upon addition of 25 nM of Mitocreatine and N-Methyl Mitocreatine (A-2, structure shown in Table 1 and page 16) to fibroblasts.

Using the same procedure, the oxygen consumption rate for compound Mitocreatine and N-Methyl Mitocreatine at a concentration of 25 nM was determined. The results obtained for both compounds are shown in FIG. 3 as percent increase in the oxygen consumption relative to the oxygen consumption rate measured upon addition of 10 μM creatine. Using the same procedure, the oxygen consumption rate (OCR) for additional compounds was measure in HepG2 human liver carcinoma cells. Compounds were added in concentrations ranging from 0.25 nM to 200 nM. All compounds demonstrated an increase in oxygen consumption rate as shown in Table 4 as expressed as a percentage increase over control (where control is 100) at indicated concentrations.

Table 4 shows oxygen consumption rates of HepG2 human liver carcinoma cells after treatment of creatine analogs at different concentrations.

TABLE 4

| Compound No. | Concentration (nM) | Oxygen Consumption Rate (OCR) |
|---|---|---|
| A-3 (Mitocreatine) | 10 | 124 |
| A-2 (N-methyl Mitocreatine) | 10 | 106 |
| A-5 | 10 | 117.9 |
| A-6 | 0.25 | 121 |
| A-7 | 20 | 112 |
| A-8 | 2.5 | 115.7 |
| A-9 | 2.5 | 121.9 |

Example 2b: Analysis of OCR for Compounds B-1A and B-5a

The day of the experiment, the injection ports on the sensor cartridge were loaded with Compound B-1A or Compound B-5A as indicated at 10× concentrations and placed into the XF24 Flux Analyzer for automated calibration. During the sensor calibration, cells in each of the tissue culture wells were rinsed once in 1 mL of unbuffered media. 675 μL of unbuffered media was then added to each well, and the plate was incubated for an hour in the absence of additional $CO_2$. Plates were subsequently placed into the calibrated seahorse XF24 flux analyzer for bioenergetic analysis. An equivalent number of cells per well were plated using a cell counter. Further normalization was achieved by taking baseline measurements of OCR on a well-by-well basis, and the increase observed was a comparison to the same well prior to treatment. Thus each well serves as its own control.

At time point A a creatine derivative was added to the wells to reach the indicated concentrations. At time point A the modified creatine compound was added to the wells to reach the indicated concentrations. At time point B1 μg/ml Oligomyacin, at time point C3 μM FCCP and time point D1 μM Rotenone was added to reach the indicated concentrations.

Figure 4:
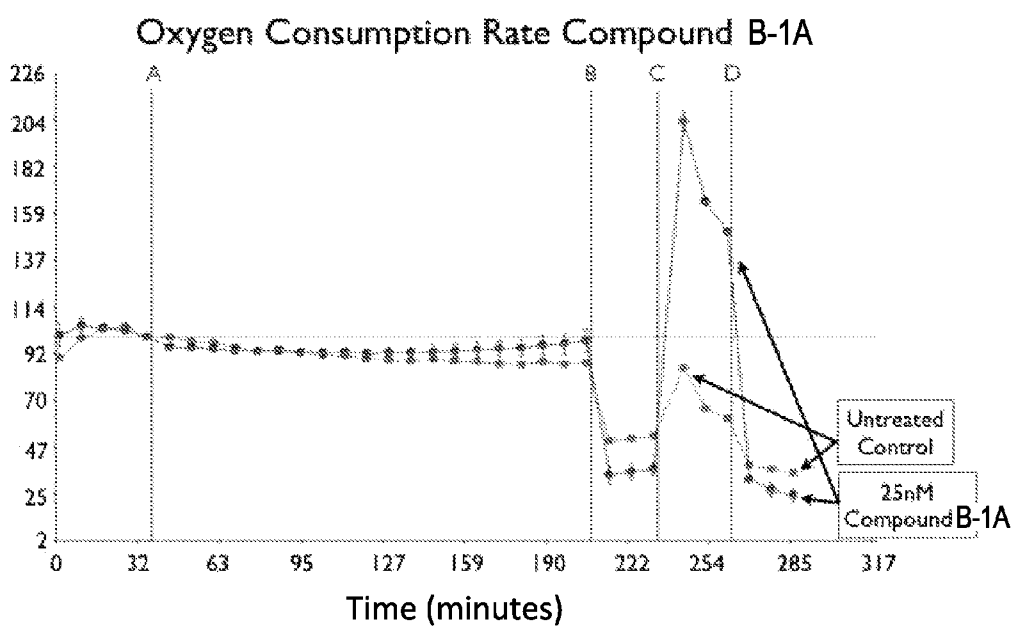
FIG. 4 depicts the oxygen consumption rate (% OCR) upon addition of 25 nM of compound B-1A (structure shown in page 21) to fibroblasts.
Figure 5:
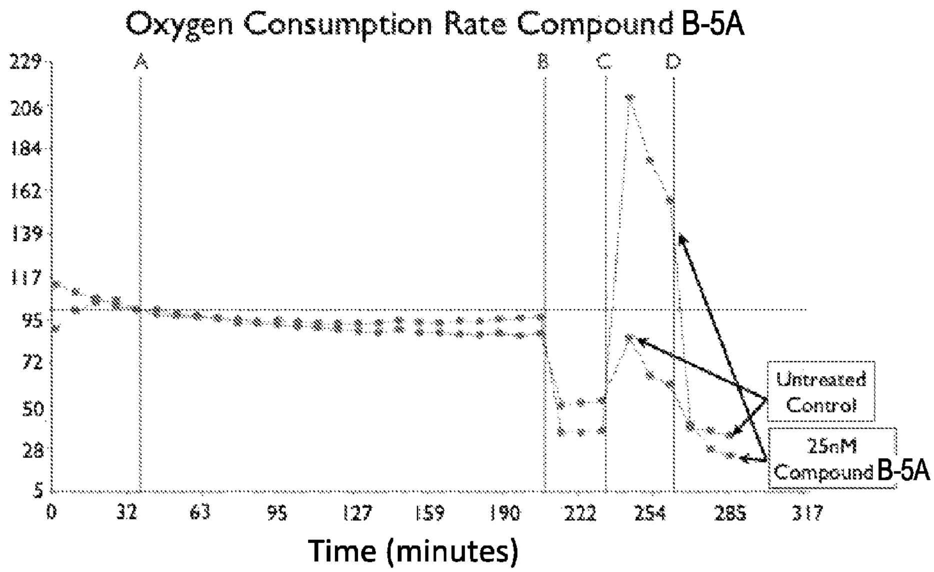
FIG. 5 depicts the oxygen consumption rate (% OCR) upon addition of 25 nM of compound B-5A (structure shown in page 21) to fibroblasts.
Figure 6:
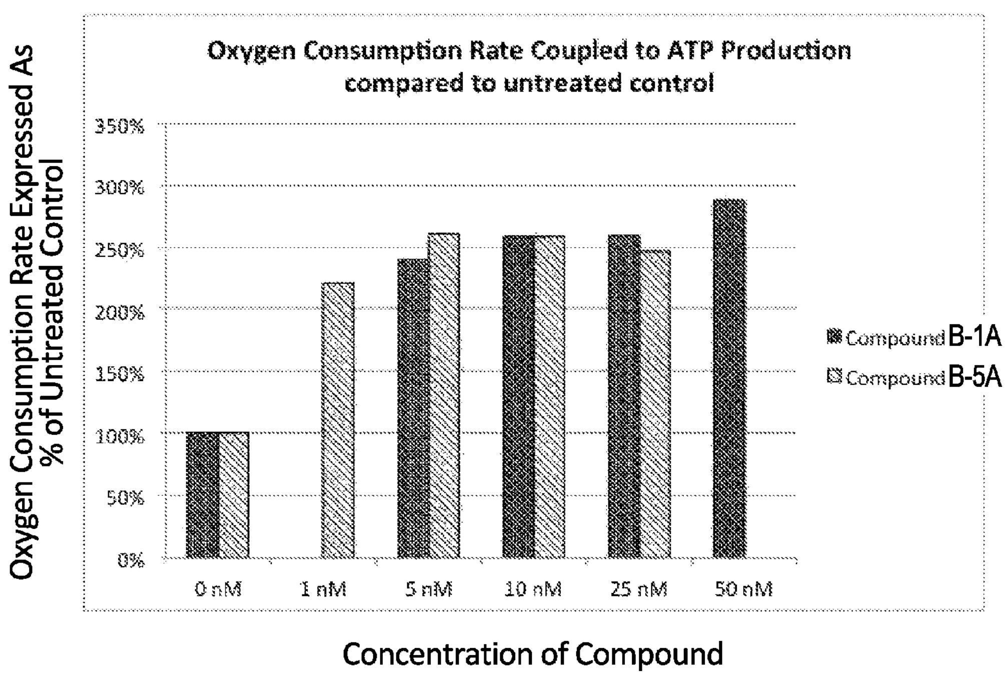
FIG. 6 depicts a bar graph showing the percent increase in oxygen consumption rate (% OCR) upon addition of compound B-1A and compound B-5A to fibroblasts at various concentrations.

The results of the assay for compound B-1A and B-5A at 25 nM concentrations were shown in FIGS. 4 and 5 respectively as a percent change prior to treatment. For comparison, the results obtained for compounds B-1A and B-5A were plotted against the untreated control in each graph. Although a small increase in oxygen consumption rate was observed, a more significant increase in the percentage of oxygen consumption that was coupled to ATP production (FIG. 6) and maximal oxygen consumption rate (FIG. 7) was observed. The samples were performed in duplicates; samples with large internal deviations were not included). Oxygen consumption by the mitochondria optimally leads to ATP production. However some oxygen consumption results in free radical production, and the degree to which this occurs was termed coupling, i.e. the oxygen consumption can be more or less coupled to the production to ATP. FIG. 6 indicates that both compounds B-1A and B-5A increase the rate of which oxygen is coupled to Complex V activity.

Figure 7:
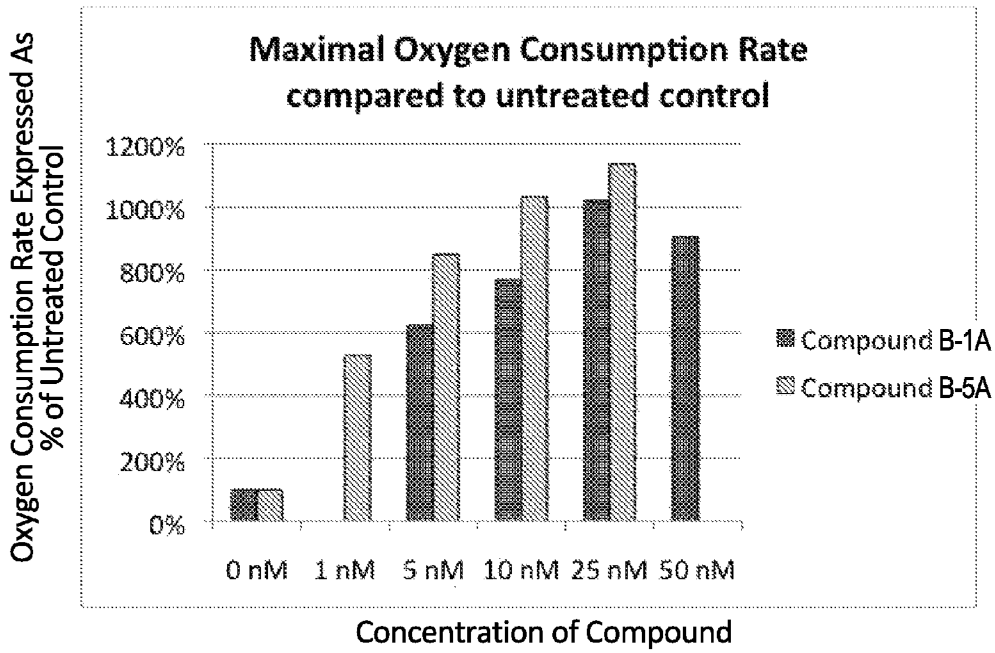
FIG. 7 depicts a bar graph showing maximal oxygen consumption rate (% OCR) upon addition of compound B-1A and compound B-5A to fibroblasts at various concentrations.

As shown in FIG. 7, through the addition of a decoupling agent such as FCCP, a measure of the maximal oxygen consumption rate of cells mitochondria is achieved. Compound B-1A and B-5A show a concentration dependent increase of maximal oxygen consumption rate compared to untreated control.

Example 3: Effects of Mitocreatine on Aged Skin Fibroblasts in a 3D Collagen Cell Culture System The effects of Mitocreatine on skin fibroblasts cultured in a 3D matrix to better simulate in vivo milieu were examined. The cells were visualized by phase contrast light microscopy and their biological response to different concentrations of Mitocreatine evaluated. The 3D Collagen Cell Culture System from Millipore (Catalogue number ECM 675) was utilized.

All liquids were prepared according to manufacturer's instructions, and kept on ice. Tissue culture plates were coated with collagen by pipetting 500 μL of chilled Collagen Gel Solution into each well of a 24 well tissue culture plate. The plate was immediately transferred to a 37° C. incubator for 60 min to initiate polymerization of the collagen.

After the formation of the collagen gel, AG11073 and AG16409 cells were harvested and re-suspended at $4\times10^5$/mL and $1\times10^6$ cells were seeded onto the collagen gel. The cells were obtained using the procedure as described in Example 1.

After overnight incubation at 37° C. with 5% $CO_2$ the media was replaced with fresh media containing various doses of Mitocreatine or the vehicle. Cells were visualized daily using phase contrast microscopy.

Figure 8:
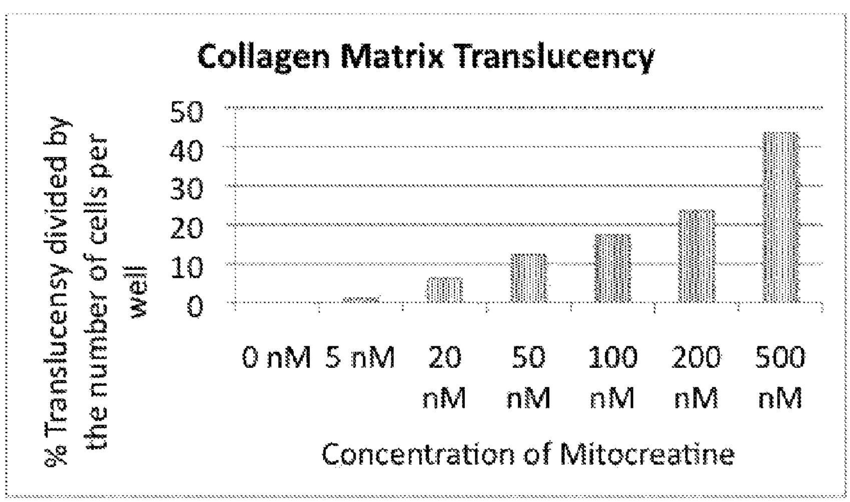
FIG. 8 depicts a bar graph showing collagen matrix translucency when fibroblasts from a 75-year old male were treated with Mitocreatine at various concentrations.
Figure 9:
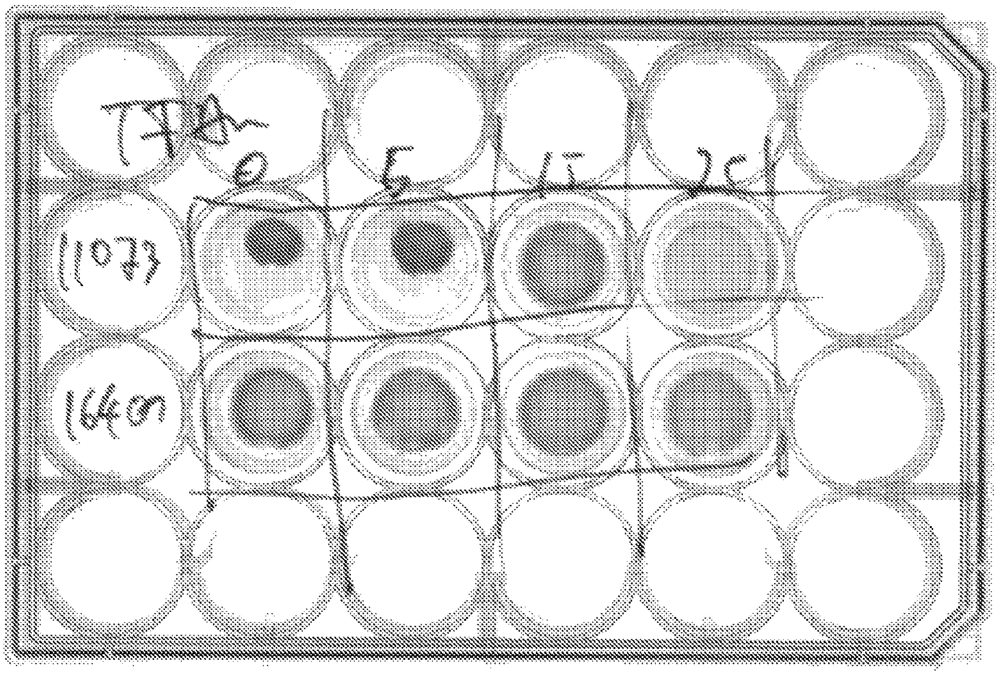
FIG. 9 depicts effect of rhTFAM on aged skin fibroblasts?

Fibroblasts from a 75-year old male were cultured on a collagen matrix. Two days after seeding, cells were treated with a Mitocreatine at increasing amounts (0, 5, 15 and 25 μL). Five days post-treatment, collagen shrinkage was assayed by means of translucency. Results are shown in FIG. 8. Mitocreatine treatment caused a dose-dependent increase in collagen matrix translucency, an indirect indication of a reduction of damage caused upon the collagen matrix by fibroblasts from the aged individual. No change in collagen translucency was seen in a similar experiment utilizing fibroblasts from a 12-year old boy.

Example 4: Effects of rhTFAM on Aged Skin Fibroblasts in a 3D Collagen Cell Culture System The experiment was performed, following the procedure described in Example 3 and using a recombinant polypeptide rhTFAM molecule instead of a modified creatine analogue. Fibroblasts from a 75-year old male and a 12-year old male (16409) were cultured on a collagen matrix. Two days after seeding, cells were treated with rhTFAM at increasing amounts (0, 5, 15 and 25 μL, giving a final concentration of 0, 0.3, 0.9 and 1.8 μg/mL respectively). Five days post-treatment, collagen shrinkage was assayed and imaged. Results are shown in FIG. 6 and rhTFAM treatment caused a dose-dependent decrease in collagen damage produced by fibroblasts from the aged individual.

Figure 10:
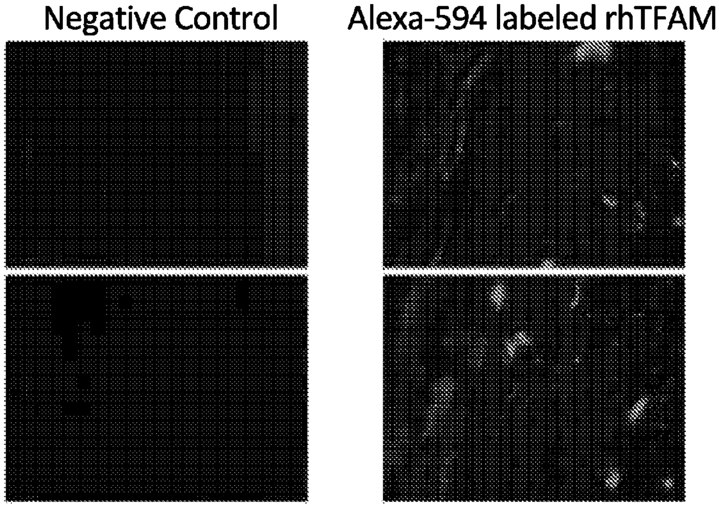
FIG. 10 depicts the penetration of recombinant transcription factor A-mitochondrial (TEAM) past stratum corneum in human skin. Red fluorescence present in the basal cell indicates the uptake of the labeled protein into cells.

Example 5: Analysis of TFAM Penetration Past the Stratum Corneum in Human Skin rhTFAM was labeled with Alexa-594 (Invitrogen A20004) using succinylmidyl ester conjugation to free amine groups according to the manufacturer's protocol. The labeled protein was then desalted and purified on a PD-10 column (GE 17-0851-01). 5 μg of protein was applied to the apical surface, stratum corneum, of reconstituted human skin from MatTek Corporation. After incubating the skin sections at 37° C. for 24 hours the skin was fixed in 10% formalin, and sectioned at 10 micron thickness and visualized on an epifluorescent microscope (Leica DM6000) (FIG. 10). Red fluorescence present in the basal cells indicated uptake of the labeled protein into cells.

Example 6: Analysis of rhTFAM Effects on Human Skin

All experiments were conducted on EpiDerm tissue plates from Mattek (according to the manufacturer's protocols where appropriate). RhTFAM was applied to the apical surface of reconstituted human skin in EpiDerm plates. At 24 hours post-treatment skin cells were assayed using the following measures.

Example 6a: Mitochondrial Mass

Figure 11:
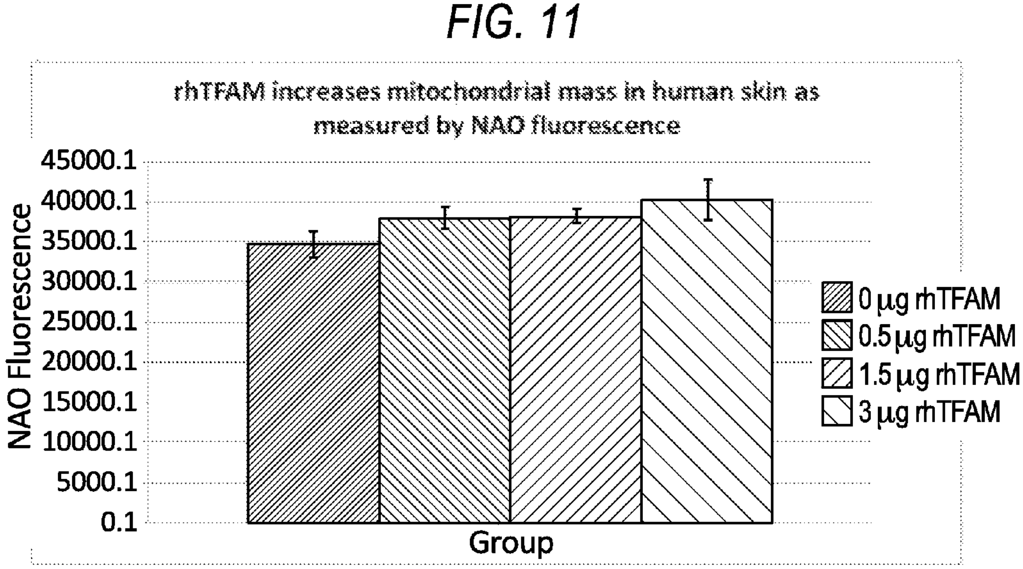
FIG. 11 depicts a bar graph showing MTT (3-[4,5-dimethylthiazol-2-yl]-2,5-diphenyl tetrazolium bromide) absorbance upon addition of rhTFAM at various concentrations.

NAO (nonyl-acridine orange) was retained in mitochondria independent of mitochondrial membrane potential by binding to cardiolipin in the inner mitochondrial membrane. NAO staining was used to assay mitochondrial mass by incubating cells in 10 mM NAO for 10 minutes followed by reading in a plate reader with ex: 500 nm em: 525 nm. Values are expressed in terms of vehicle control fluorescent intensities (FIG. 11).

Example 6b: MTT Assay

Figure 12:
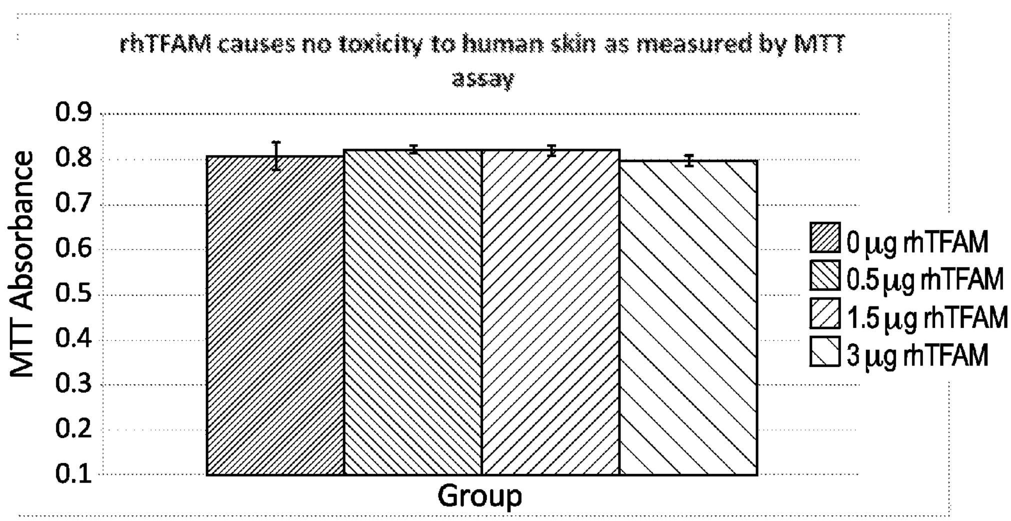
FIG. 12 depicts a bar graph showing the mitochondrial mass in human skin cells upon treatment with rhTFAM.

A colorimetric assay system that measures the reduction of a yellow 3-[4,5-dimethylthiazol-2-yl]-2,5-diphenyl tetrazolium bromide (MTT) into an insoluble purple formazan product by the mitochondria of viable cells was used. After incubation of the cells with the MTT reagent for several hours, a solution was added to lyse the cells and solubilize the colored crystals. Samples are read using a colorimetric plate reader at a wavelength of 570 nm. The amount of color produced is directly proportional to the number of viable cells (FIG. 12).

Example 6c: Reactive Oxygen Species (ROS) Measurements

Figure 13:
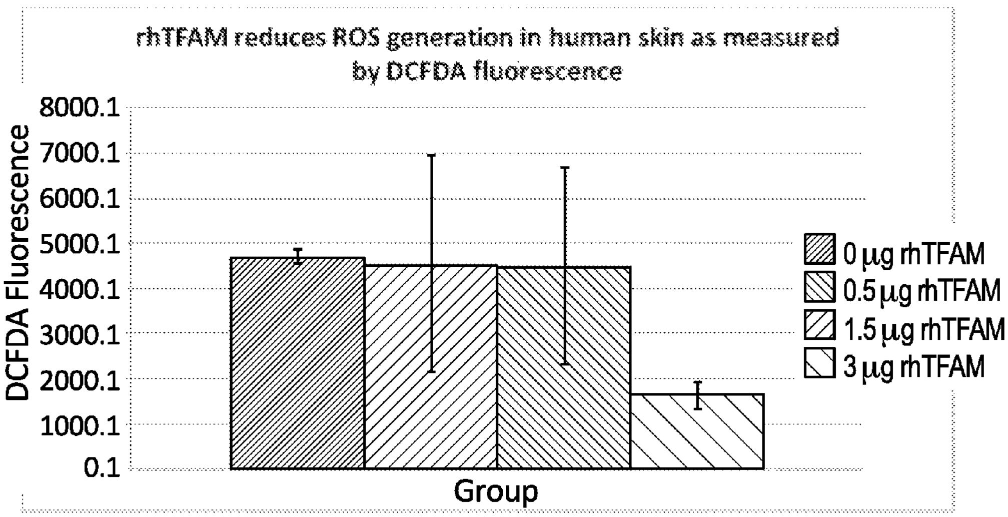
FIG. 13 depicts a bar graph showing the reactive oxygen species (ROS) measurement in human skin cells upon treatment with rhTFAM.

DCFDA was used for analysis of intracellular ROS. Twenty-four hours post-rhTFAM treatment cell media was replaced with DMEM without phenol red containing 1 μM 6-carboxy-2',7'-dichlorodihydrofluorescein diacetate (DCDHA) for 1 hour at 37° C. in the dark. The fluorescence signal of 6-carboxy-2',7'-dichlorofluorescin diacetate (Ex: 490 nm; Em: 520: the oxidation product of DCDHF by ROS), were acquired on a PHERAstar FS Reader (BMG Labtech Cary, N.C.) and expressed as percent of vehicle control treated cells (FIG. 13).

Example 6d: Delta Psi Measurements

Figure 14:
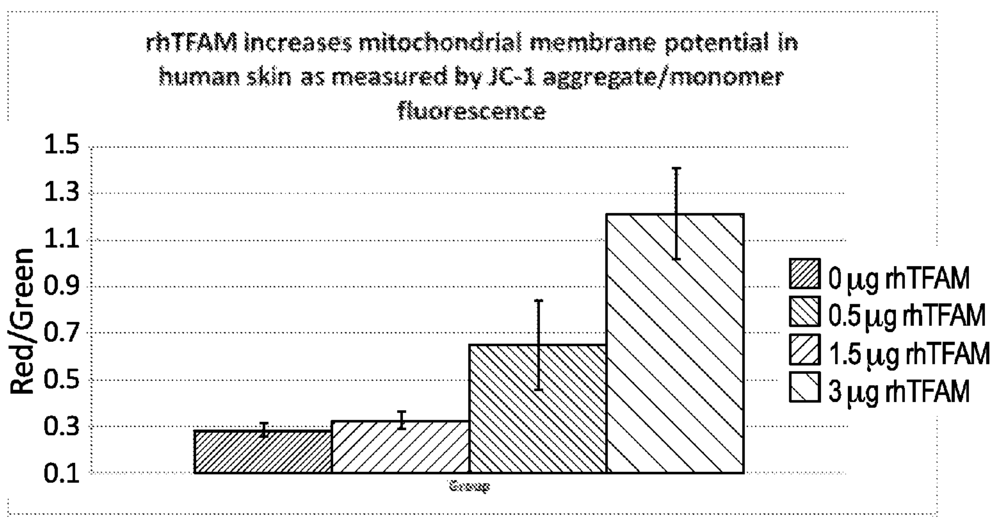
FIG. 14 depicts a bar graph showing the mitochondrial membrane potential increase in human skin cells upon treatment with rhTFAM.

Mitochondrial membrane potential (Δψm) is an important parameter of mitochondrial function used as an indicator of cell health. JC-1 is a lipophilic, cationic dye (5,5',6,6'-tetrachloro-1,1'3,3'-tetraethylbenzimidazolocarbocyanine chloride or iodide salt) that can selectively enter into mitochondria and reversibly change color from green to red as the membrane potential increases. In healthy cells with high mitochondrial membrane potential, JC-1 spontaneously forms complexes known as J-aggregates with intense red fluorescence. On the other hand, in apoptotic or unhealthy cells with low Δψm, JC-1 remains in the monomeric form, which shows primarily green fluorescence. The ratio between the red aggregate and the green monomer indicate relative mitochondrial membrane potential. Thus the ratio of green to red fluorescence was dependent only on the membrane potential and not on other factors such as mitochondrial size, shape, and density, which may influence single-component fluorescence signals. 2 uM JC-1 was used to stain cells for 30 min at 37° C. in the dark. Cells were washed with warm PBS and analyzed with ex: 488 nm em: 520 and ex: 560 nm and em: 590 nm. The ratio between the fluorescent intensities of the red versus green signals was then normalized and expressed in terms of vehicle control cells (FIG. 14). The results indicate that rhTFAM increases mitochondrial membrane potential in human skin as measured by JC-1 aggregate/monomer fluorescence.

Example 7: Survival of Fibroblasts Treated with High Concentrations of Chemotherapeutic Agents Fibroblasts were incubated with increasing amounts of Mitocreatine and certain anti-neoplastic agents, such as Cetuximab, Gemcitabine and Temozolomide. After incubation, cells were washed and the number of adherent (i.e. surviving) cells was assessed by DAPI fluorescence, which was measured utilizing a plate reader (PHERA Star FS from BMG Labtech). For these experiments two kinds of cells were used. Either the Human hepatocellular liver carcinoma cell line HepG2, or the BJ human fibroblast cells, which are established from normal human foreskin. The BJ fibroblasts were purchased from Stemgent Inc.

Figure 15:
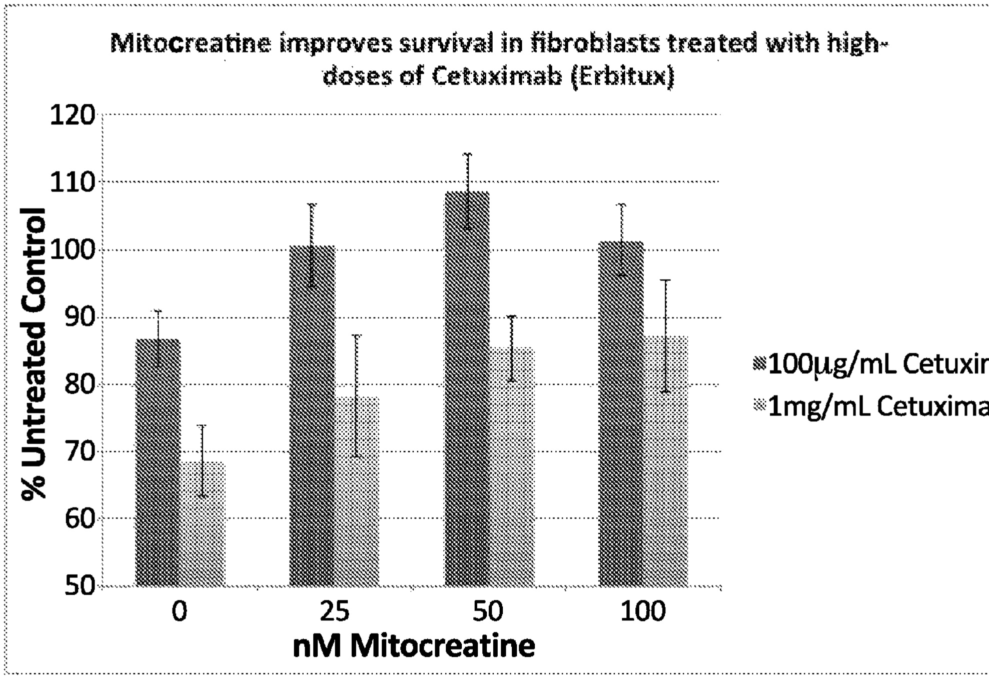
FIG. 15 depicts a bar graph showing the survival improvement of fibroblasts that were treated with high doses of Cetuximab (Erbitux), and then treated with Mitocreatine at various concentrations.
Figure 16:
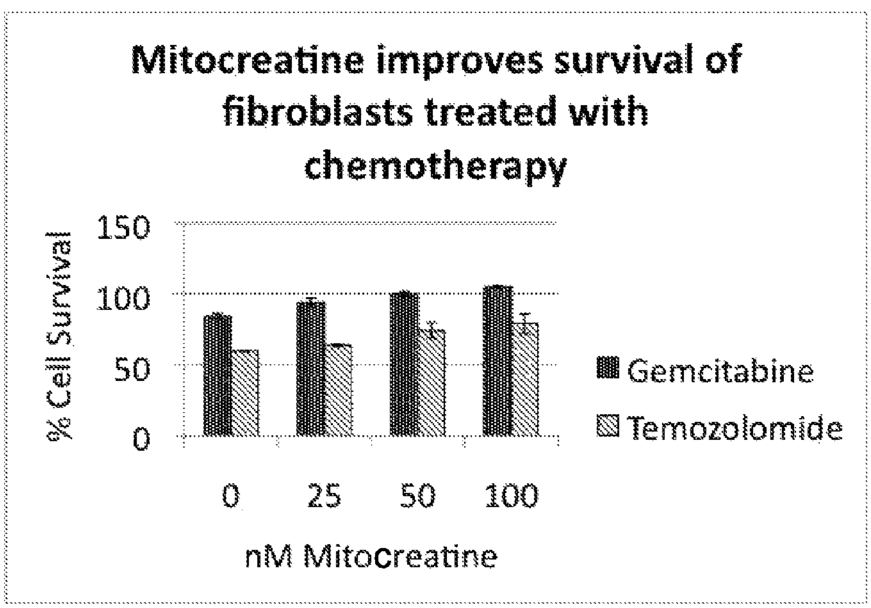
FIG. 16 depicts a bar graph showing the survival improvement of fibroblasts that were treated with Gemcitabine and Temozolomide, and then treated with Mitocreatine at various concentrations.
Figure 17:
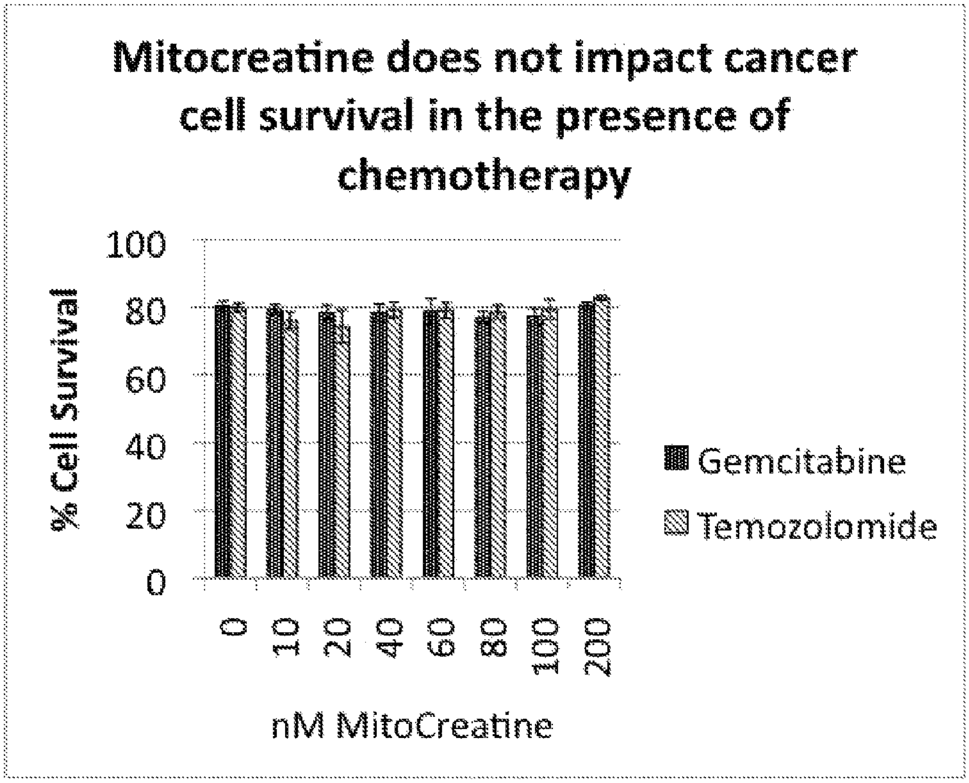
FIG. 17 depicts a bar graph showing the impact on fibroblasts that were treated with Gemcitabine and Temozolomide, and then treated with Mitocreatine at various concentrations.
Figure 18:
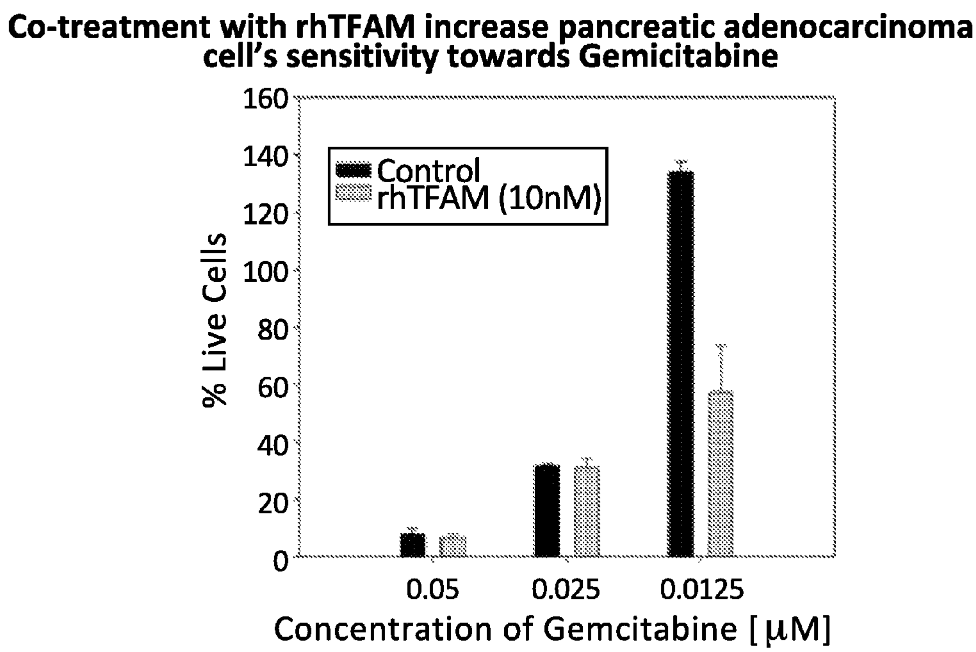
FIG. 18 depicts a bar graph showing the effect of rhTFAM on the $IC_{50}$ concentration of Gemcitabine.
Figure 19:
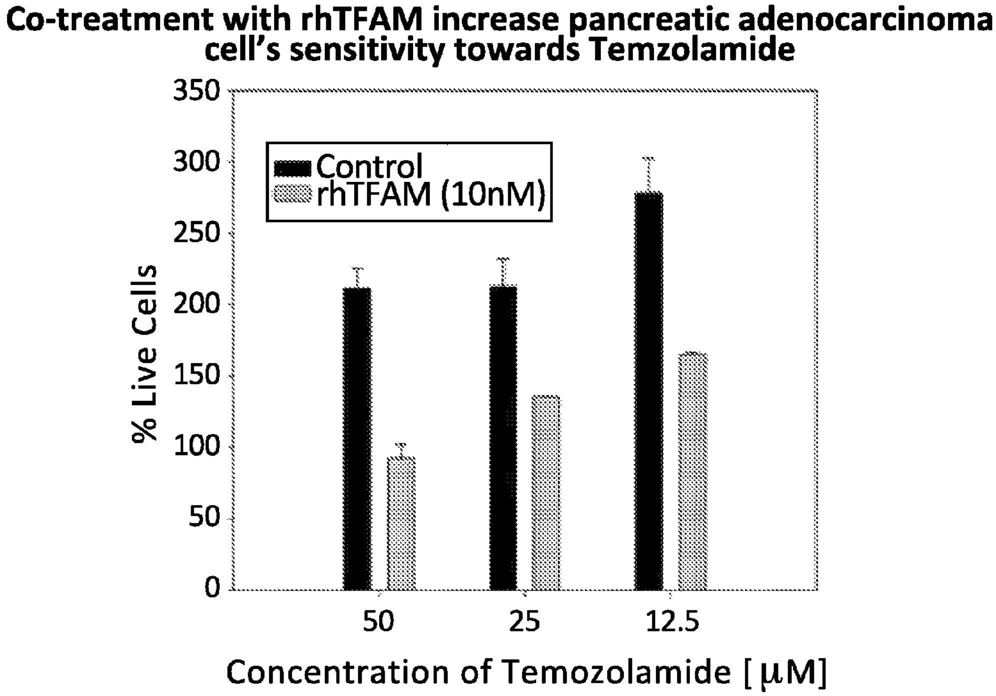
FIG. 19 depicts a bar graph showing the effect of rhTFAM on the $IC_{50}$ concentration of Temozolamide.
Figure 20:
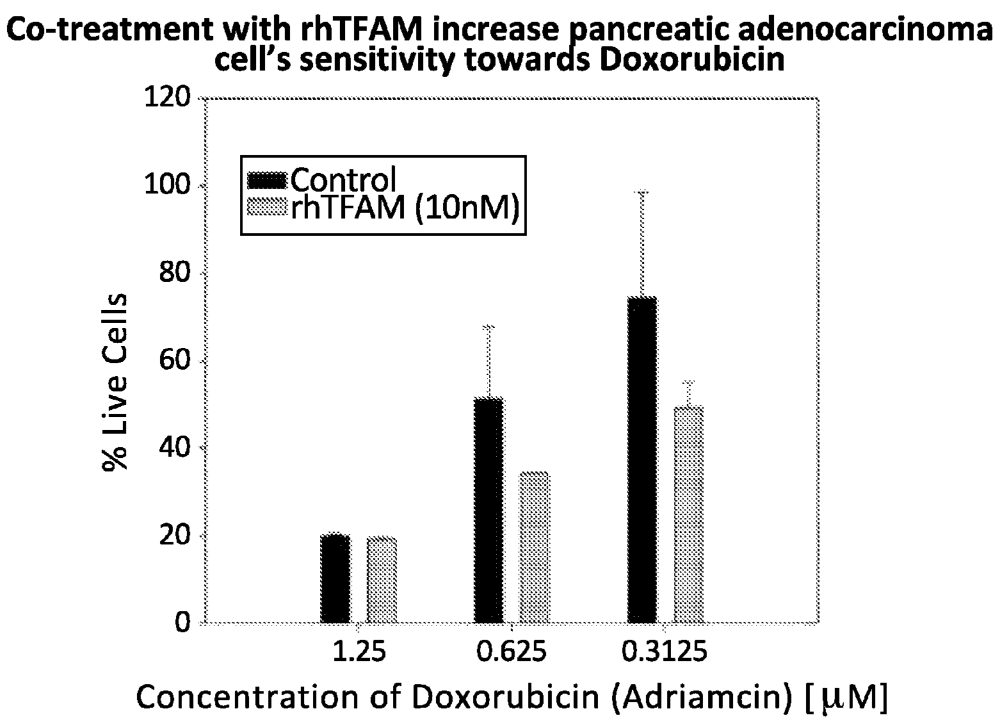
FIG. 20 depicts a bar graph showing the effect of rhTFAM on the $IC_{50}$ concentration of Doxorubicin (Adriamycin).
Figure 21:
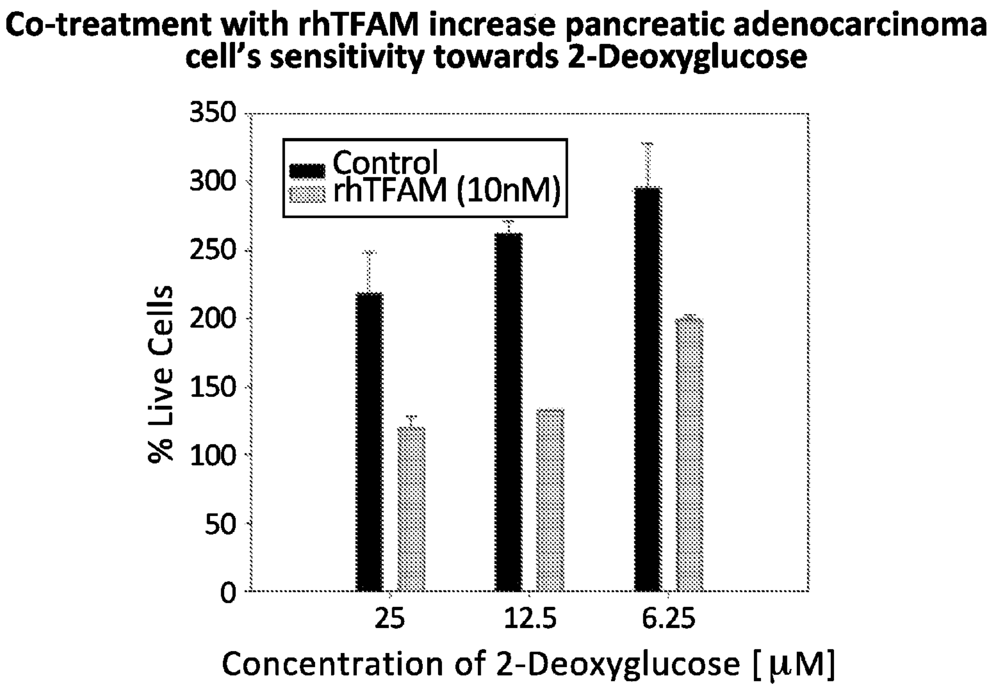
FIG. 21 depicts a bar graph showing the effect of rhTFAM on the $IC_{50}$ concentration of 2-deoxyglucose.
Figure 22:
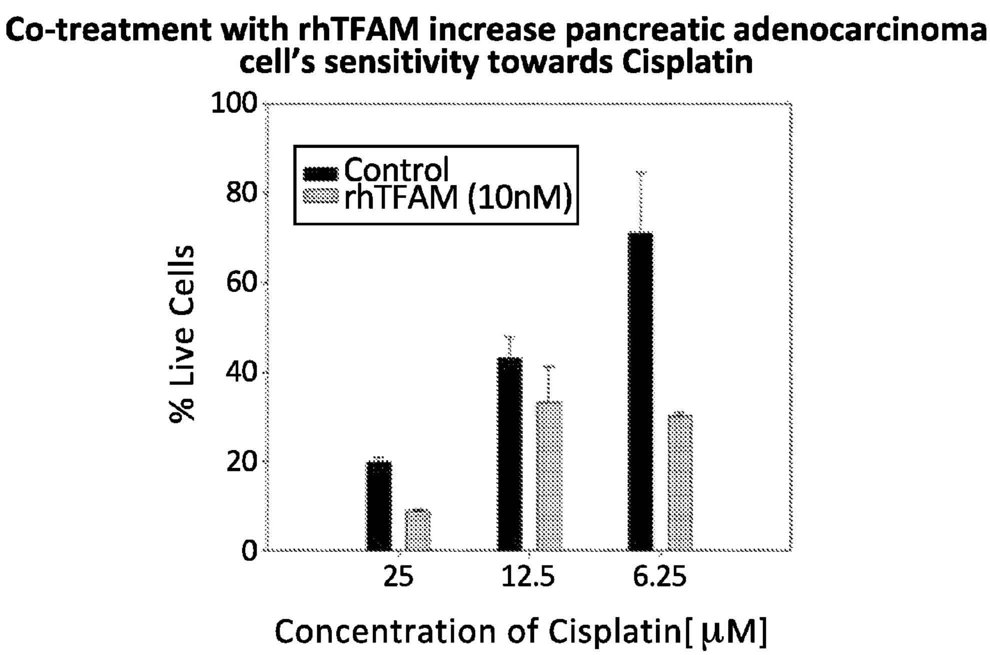
FIG. 22 depicts a bar graph showing the effect of rhTFAM on the $IC_{50}$ concentration of Cisplatin.

Mitocreatine improved the survival of fibroblasts treated with high concentrations of Cetuximab, Gemcitabine (80 μM) or Temozolomide (1 mM) for 48 hours, but did in contrast not improve the survival of HepG2 cells (FIGS. 15-17). Mitocreatine and the antineoplastic agent were added simultaneously.

Example 8: rhTFAM Lowers the $IC_{50}$ Concentration for Five Different Chemotherapeutic Agents Approximately 1500 Pan02 murine pancreatic adenocarcinoma cells were plated in a 96 well plate, and placed in a hypoxia chamber, which was purged with nitrogen for 15 minutes. The chamber was sealed and placed in 37° C. incubator without CO2 for 5 days. Plates were removed and inspected visually under a phase contrast light microscope.

Cells were treated with vehicle control or 10 nM rhTFAM, and various dosages of Gem: Gemcitabine (0.05 pM, 0.025 pM, and 0.0125 pM) TMZ: Temozolamide (50 μM, 25 μM, and 12.5 μM), Dox: Doxorubicin (Adriamycin) (1.25 μM, 0.625 μM, and 0.3125 μM), Cis: Cisplatin (25 μM, 12.5 μM, and 6.25 μM), or 2-DO: 2-deoxyglucose (25 μM, 12.5 μM, and 6.25 μM).

RhTFAM and drugs were added to cells upon plating and left on the cells for the duration of the experiment (i.e., 5 days). The cells were left in a hypoxia chamber and not disturbed to keep oxygen levels low. Cells were subsequently prepared for live/dead testing according to manufacturer's protocol (Life Technologies 143224). RhTFAM sensitizes cancer cells to chemotherapeutic agents under hypoxic conditions as shown in FIGS. 18-22.

Example 9: rhTFAM does not Lower Delta-Psi in Fibroblasts and does not Sensitize the Cells to Apoptosis The mitochondrial potentiometric dye, JC-1, was utilized to assay relative changes in mitochondrial membrane potential. A 96-well black culture plate was seeded with non-malignant human fibroblasts and HepG2, a human hepatocellular carcinoma cell line at $1\times10^6$ cells/well twenty-four hours before the experiment was begun. Cells were maintained in 100 μL culture medium per well in a $CO_2$ incubator overnight at 37° C. Cells were treated with rhTFAM at 1-2 μg/ml, or left untreated, in triplicate. 10 μL of the JC-1 Staining Solution was added to each well and mixed gently. The cells were incubated in a $CO_2$ incubator 37° C. for 15 minutes. The cell media was aspirated and additional 200 μL of cell media was added. This was repeated two times. 100 μL of cell media was added to each well. The cells were analyzed in a fluorescent plate reader. In healthy cells, JC-1 forms J-aggregates which display strong fluorescent intensity with excitation and emission at 560 nm and 595 nm, respectively. In apoptotic or unhealthy cells, JC-1 exists as monomers, which show strong fluorescence intensity with excitation and emission at 485 nm and 535 nm, respectively. The ratio of fluorescent intensity of J-aggregates to fluorescent intensity of monomers can be used as an indicator of mitochondrial membrane potential.

Figure 23:
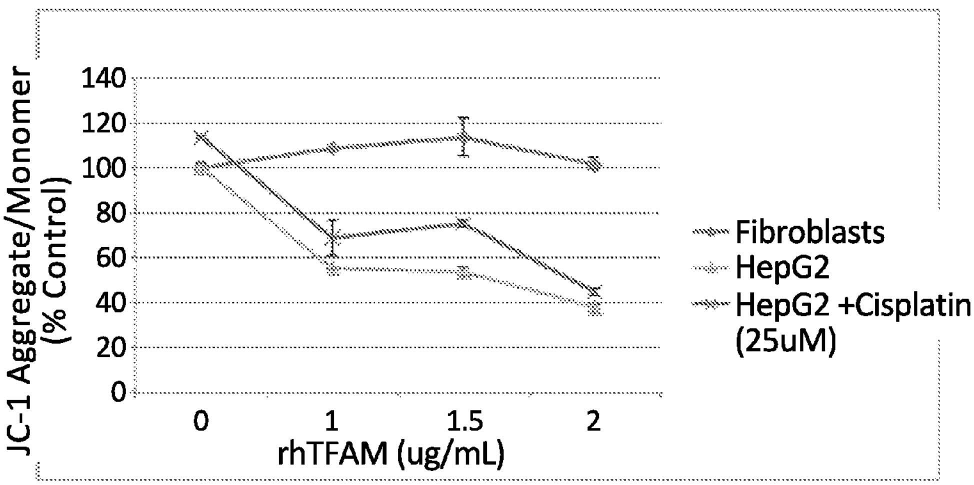
FIG. 23 depicts mitochondrial membrane potential upon treatment with rhTFAM at various concentrations.

RhTFAM increases coupling of oxygen consumption to ATP production. The increase in coupling reduces Δψm in cancer cells as the proton gradient is now used to drive phosphorylation of ADP (which is the very definition of coupling). Reducing Δψm to non-tumor cell levels enables the communication of the omnipresent pro-death signal in tumor cells. The lower Δψm causes mitochondrial permeability transition and the release and activation of executioner caspases, cytochrome c, AIF and downstream PARP cleavage. Normal, non-tumor cells lack the pro-death signals that appear to be ever present in tumor cells, and mitochondrial ATP production is increased. FIG. 23 is a graph showing the decrease in mitochondrial potential in HepG2 tumor cells but not in non-malignant fibroblast cells after addition of rhTFAM. The levels are expressed as a percentage of control (no rhTFAM added).

Example 10: rhTFAM does not Sensitize Fibroblasts to Apoptosis

The cells were treated with rhTFAM, and Cisplatin as described in Example 8. However, instead of measuring membrane potential, the Cell-Titre Glo (Promega) cell survival assay kit was utilized. A 96-well black culture plate was seeded with human fibroblasts and HepG2 cells at 1×106 cells/well twenty-four hours before the experiment was begun. Cells were maintained in 100 μL culture medium per well in a $CO_2$ incubator overnight at 37° C. Cells with or without rhTFAM at 1-2 μg/mL in triplicate for 48 hours. Cell-Tire Glo reagents were thawed and mixed and 100 μL of the mix added to each well. Plates were transferred to a plate reader for luminescent reads. The plate was mixed by orbital shaking for 2 minutes followed by 10 minutes at room temperature prior to measurements being made.

Figure 24:
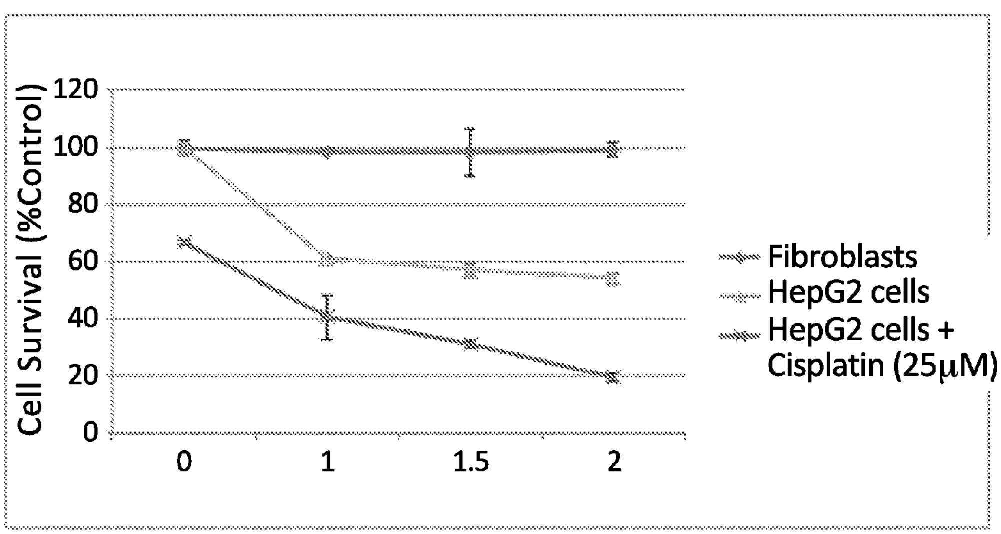
FIG. 24 depicts that cancer cells but not fibroblasts sensitive to rhTFAM treatment.

As seen in FIG. 24 rhTFAM does not increase cell death of fibroblasts. Luminescence was measured and expressed in terms of vehicle control (FIG. 24).

Example 11: Assay to Measure Intracellular Collagen

The cell line AG11073 senescent fibroblasts, at passage 20, were plated onto a multi-chambered glass slide. Dulbecco's Modified Eagle Medium (DMEM) supplemented with the appropriate serum and antibiotics and either containing vehicle or 25 nM of Mitocreatine was added to each chamber. Cells were treated once daily with fresh media containing either vehicle or 25 nM mitocreatine for seven days. At the completion of the treatment period, the cells were washed with warm PBS and fixed with ice cold acetone. The chambers were removed and the slide immunoprobed with an anti-collagen type I antibody (ab292, Abcam). An Alexa-488 secondary antibody was used for detection and DAPI used to stain nuclei. A seven day treatment protocol of 25 nM Mitocreatine showed a significant increase in intracellular collagen as well as indicating a significant increase in cell numbers.

Figure 25:
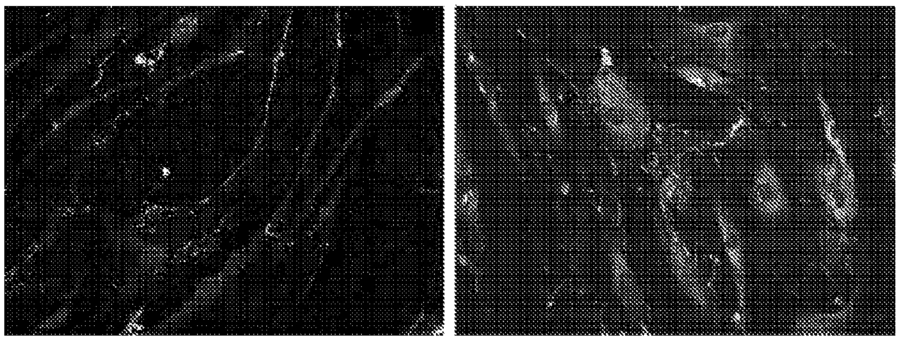
FIG. 25 shows the measurement of intracellular collagen upon treatment of fibroblasts with vehicle or 25 nM Mitocreatine.

The cells utilized were human skin fibroblast acquired from Coriell Cell Repository. The cell line AG11073 is untransformed human skin fibroblasts from a 75 years old Caucasian male. The primary culture was initiated from explants of a 2 mm-punch biopsy. The cell line AG16409 is untransformed human skin fibroblasts from a 12 years old Caucasian male. Aged senescent fibroblasts (Coriell AG11073) were cultured for 7 days with either vehicle or 25 nM mitocreatine. Cells were probed with anti-collagen type I antibody (green) and DAPI (blue) for nuclei to assess changes in collagen type I expression. As shown in FIG. 25, Mitocreatine caused a significant increase in collagen type I expression and induced cell proliferation in otherwise senescent cells.

Example 12: Image Analysis of Cell Areas

Figure 26:
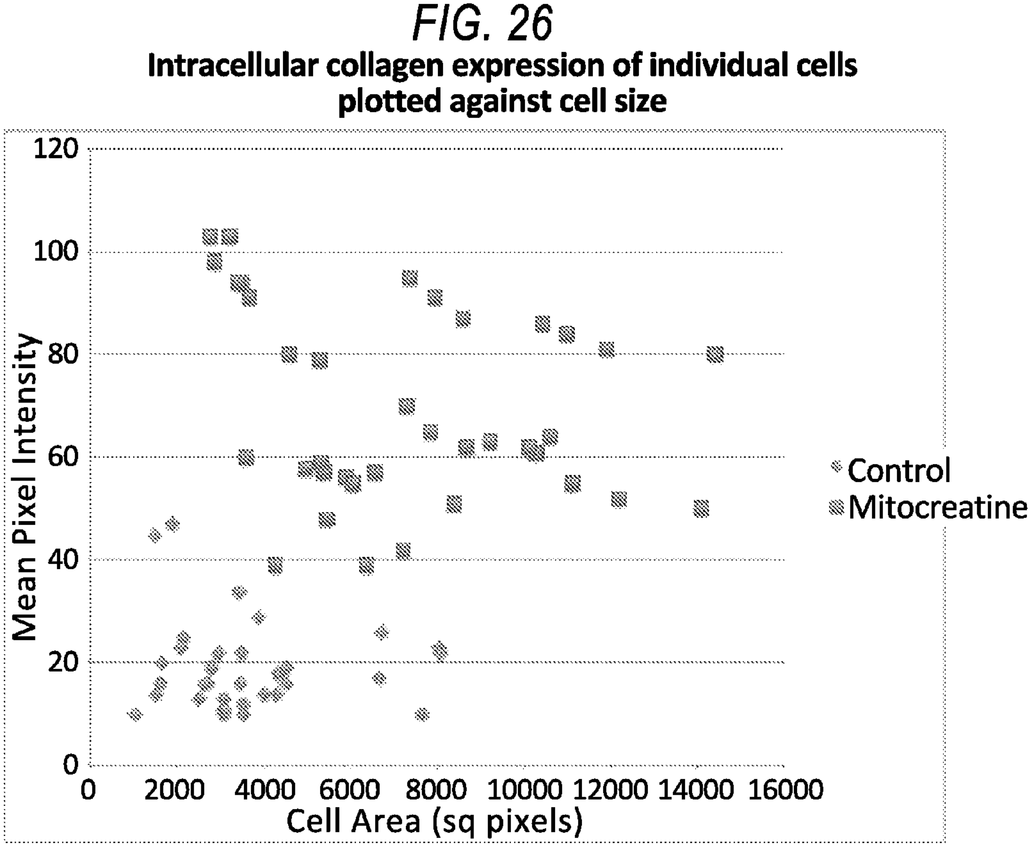
FIG. 26 depicts a graph showing cell area vs intensity from the collagen immunolabeling study, using image analysis.

The ability of compounds of the present invention to alter the cell area as well as intracellular collagen type I were measured, from the collagen immunolabeling study, using imaging analysis and the results showed (FIG. 26) an increase in cell area as well as an increase in intracellular collagen type I. From the collagen immunolabeling study, regions of interest (ROI) were drawn corresponding to phase contrast overlays encompassing cell outlines. Cell area and mean pixel intensity of the green fluorescence was acquired using Image J software. Image analysis supports an increase in cell area as well as an increase in intracellular collagen type I.

Example 13: Immunolabeling Study

Figure 27:
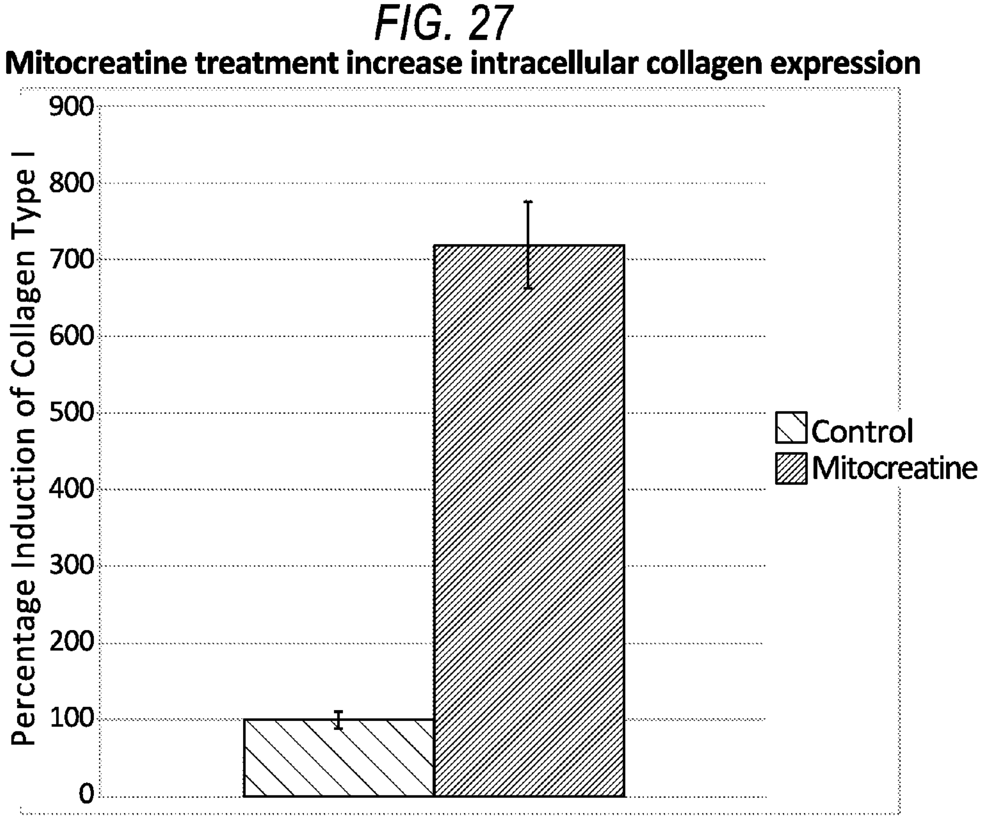
FIG. 27 depicts a bar graph showing the percent of induction of collagen type I upon treatment of fibroblasts with Mitocreatine. The values are expressed as increased fluorescent intensity per area unit and normalized to untreated cells.

Image data from the immunolabeling of collage type I study was also used to quantify the amount of collagen immunolabeling in the AG11073 senescent fibroblast treated with 25 nM Mitocreatine in vehicle for seven days. A 7-fold induction in collagen type I levels was noticed, as shown in FIG. 27.

Example 14: A Double-Blind, Randomized, Placebo-Controlled Study to Evaluate the Safety and Efficacy of 0.1% Mitocreatine Lotion on the Dorsum of the Hand A human testing program was started on Mitocreatine with a RIPT (Repeat Insult Patch Test) study, which showed that Mitocreatine is hypoallergenic in a 0.1% topical formulation. This was followed by a double-blind, randomized, placebo-controlled safety and efficacy trial of 0.1% once-daily topical application of mitocreatine to the dorsum of hands. Fifteen adult participants were recruited. After obtaining informed consent, participants were interviewed by a physician for screening for history of skin disease, allergy and general medical issues. An initial evaluation of skin on the dorsum of the hand was performed. Qualifying participants were issued the test articles and self-assessment forms, and instructed to apply the "Right hand" and "Left hand" vial contents to the dorsum of respective hands once daily, preferably in the evening. Participants were allowed the use of other cosmetics. Once a week the participants filled out the self-assessment forms as instructed during the initial evaluation. The questions in the forms pertained to comparisons of wrinkling, color, pigmented lesions, hydration, roughness and elasticity of skin between right and left hand. One question also elicited the subjective overall impression of skin appearance (better vs. worse) between the hands. After four weeks participants were again seen by the same evaluator, had an exit interview and examination. The participants and the evaluator were blinded to the treated side until after the exit evaluation was finished.

Before the start of study a set of 30 consecutively numbered pairs of bottles containing drug or placebo creams was generated. Of these 30 pairs of bottles 15 pairs treated the right side treated and 15 pairs treated the left side with the drug. The order of right vs. left treatment pairs was random. Participants were assigned a number in the order of recruitment. 17 subjects participated in the study, whereof 15 completed the study. Two subjects dropped out of the study due to non-study related causes. Of the 15 remaining individuals, 9 had their right hand treated whereas 6 had their left hand treated. Data from initial and exit evaluations and self-report forms were tabulated and analyzed using Fisher's exact test and Pearson's chi-squared test. Skin on the dorsum of participants' hands was evaluated by a physician at the initial evaluation and at the conclusion of the study. None of the volunteers had lesions disqualifying from participation (neoplasm, large vascular lesions, wounds, burns, large scars). Age-related hypo- and hyper-pigmented spots, scars and minor skin dryness were observed in some subjects and did not constitute exclusion criteria.

The weekly self-report forms included questions about the following adverse outcomes: itching, redness, pain, swelling, blistering, other discoloration, skin cracking and dryness. Participants were also provided with a contact number and instructed to immediately report any of the listed or other worrisome events.

No adverse outcomes were reported by participants throughout the duration of the study. No pathological changes were noted by the evaluating physician during the final follow-up visit.

Figure 28:
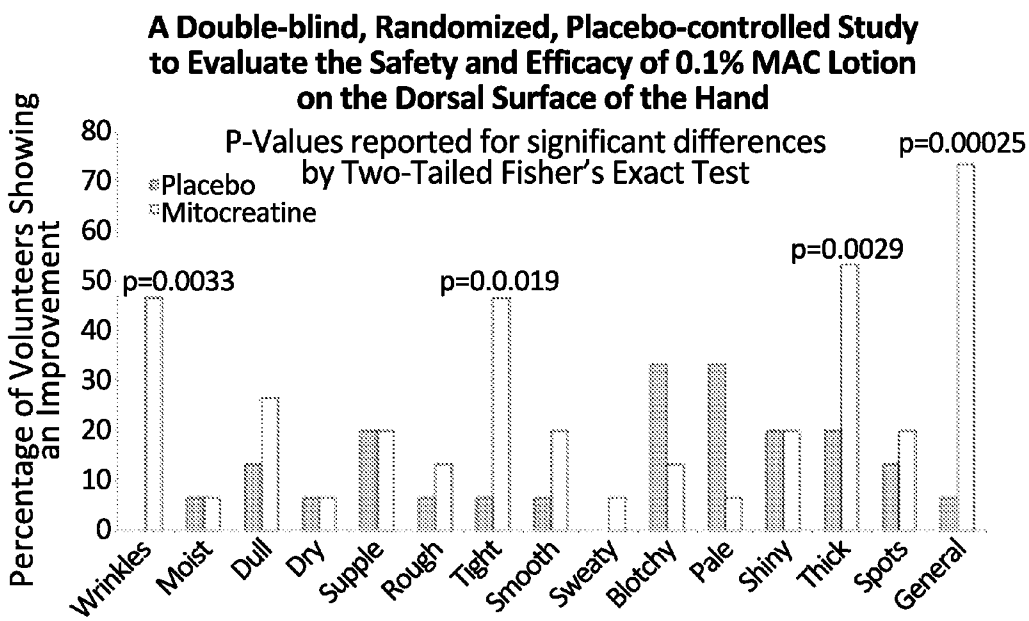
FIG. 28 depicts a bar graph showing results from a double-blind, randomized, placebo-controlled study.

Efficacy measures are shown in FIG. 28. 14/15 (93%) reported an improvement in at least two measures on drug hand versus 7/15 (45%) on placebo hand (p=0.0142). 11/15 (73%, p=0.00025) were found to have an improvement in general skin health on drug hand versus 1/15 (7%) on placebo hand. 13/15 (87%, p=0.0074 by binomial test) correctly identified the treated hand versus 1/15 (7%) misidentified the placebo hand as treated. Improvements in thickness and tightness 13/15 (87%, p=0.0029 and p=0.019) and wrinkles 7/15 (45%, p=0.0033) were the most common observations on the drug hand.

Example 15: Mitocreatine Decrease Skin Atrophy by Corticosteroids in a Mattek Full-Thickness Skin Model The Mattek FTSM (Full-thickness skin model) has been used to show the glucocorticoid-induced loss in epidermal and dermal thickness. Schoepe S, Schacke H, Bernd A, Zoller N, Asadullah K. Identification of novel in vitro test systems for the determination of glucocorticoid receptor ligand-induced skin atrophy. Skin Pharmacol Physiol. 2010; 23(3):139-51. doi: 10.1159/000270386. Epub 2009 Dec. 23. PubMed PMID: 20051715. Zöller N N, Kippenberger S, Thaçi D, Mewes K, Spiegel M, Sattler A, Schultz M, Bereiter-Hahn J, Kaufmann R, Bernd A. Evaluation of beneficial and adverse effects of glucocorticoids on a newly developed full-thickness skin model. Toxicol In Vitro. 2008 April; 22(3):747-59. doi: 10.1016/j.tiv.2007.11.022. Epub 2008 Feb. 4. PubMed PMID: 18249522.

Following the protocol of Schoepe, we used the FTSM model to determine if co-treatment with Mitocreatine would reduce the loss in skin thickness produced by glucocorticoids. This assay shows Mitocreatine improves the reduction in skin thickness brought about by steroid therapy.

2.5 mL of EpiDerm Full Thickness 400 (EFT-400) medium was dispensed into each well of the four 6-well plates aseptically in the tissue culture hood. The plates containing the EFT-400 tissues were removed from their plastic packaging and transferred using sterile forceps into the 6-well plates containing the 2.5 mL of EFT-400 media, making sure that no agarose adheres to the insert and that the media makes full contact with the underside of the tissue insert membrane (no air bubbles under the insert). The apical surface of the tissue should remain exposed to air (no media should be added to the side of the insert).

The tissues were equilibrated overnight at 37° C., 5% $CO_2$. Treatment conditions are listed below in Table 5.

TABLE 5

| Condition | Treatment |
|---|---|
| 1 | DMSO - Vehicle |
| 2 | 25 nM Mitocreatine (MC) |
| 3 | 100 nM Dexamethasone (DEX) |
| 4 | 100 nM Dexamethasone + 25 nM Mitocreatine |
| 5 | 50 nM Betamethasone (Betam) |
| 6 | 50 nM Betamethasone + 25 nM Mitocreatine |
| 7 | 10 nM Clobetasol (Clotet) |
| 8 | 10 nM Clobetasol + 25 nM Mitocreatine |

Day 2-13: The plates were visually examined and the media containing the test compounds was replenished each day.

Day 14: Each tissue insert was individually washed twice with PBS and submerged in 6 well plates containing 10% phosphate buffered Formalin (Fisher Scientific Cat#: SF-100-4 Lot:130535) for overnight fixation at room temperature.

Day 15: The inserts were dislodged from the support and the tissue carefully removed from the support with a scalpel.

The tissues were placed in 50 mL conical tubes containing 10% phosphate buffered formalin and sent for sectioning, histological processing and H&E staining Slides were visualized using a Leica Stereoscope equipped with a digital camera. Images were acquired and measured using ExoLabs software. Data was tabulated in Excel and the results were analyzed.

Corticosteroid treatment over the course of 14 days caused a significant reduction in FTSM thickness producing on average a 26% reduction in skin thickness for the three corticosteroids tested, dexamethasone, betamethasone and Clobetasol ($p<0.001$ by Student's T-Test).

Figure 29:
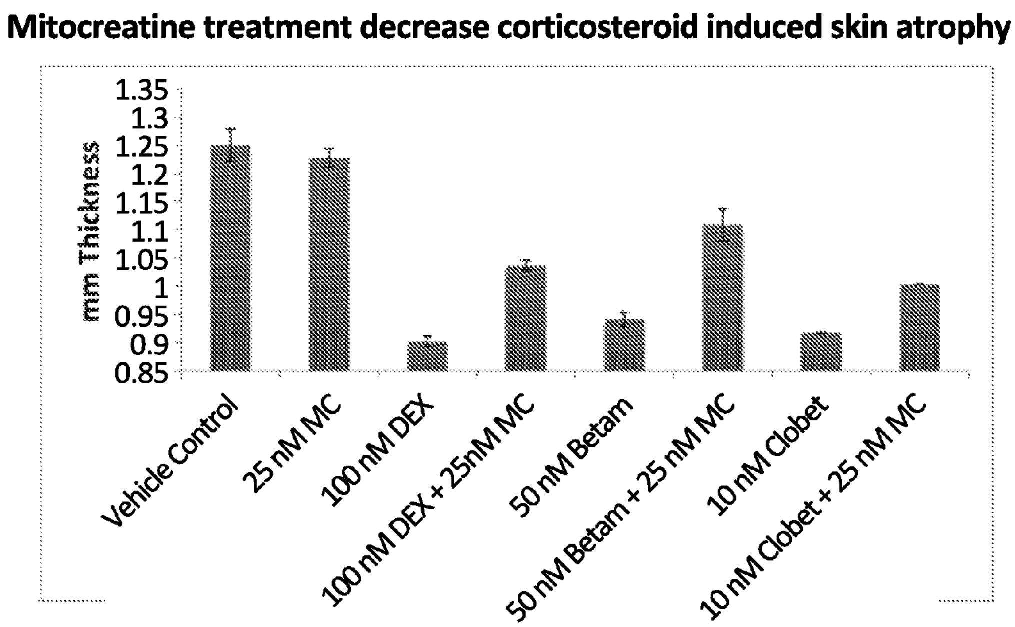
FIG. 29 depicts a bar graph showing the improvement in skin thickness in standard EpiDerm Full Thickness assay (EFT-400) upon treatment with various drugs and/or combinations thereof.

Inclusion of 25 nM Mitocreatine improved skin thickness by 50% on average ($p<0.001$ by Student's T-Test), as shown in FIG. 29.

Example 16: Mitocreatine Increases Endurance and Strength in Mice after Once Daily Dosing for 30 Days Group Setting: C57BL/6J mice were randomly assigned into five groups with different treatment started with balanced full-paw and fore-paw grip strength.

Seventy five female mice were dosed at 4 PM for 30 consecutive days (qd).

1. Vehicle (p.o. via oral gavage once daily for 30 days, n=15)
2. Creatine (300 mg/kg, p.o. via oral gavage once daily for 30 days, n=15)
3. Mitocreatine (10 mg/kg, p.o. via oral gavage once daily for 30 days, n=15)
4. Mitocreatine (20 mg/kg, p.o. via oral gavage once daily for 30 days, n=15)
5. Mitocreatine (30 mg/kg, p.o. via oral gavage once daily for 30 days, n=15).

Figure 30:
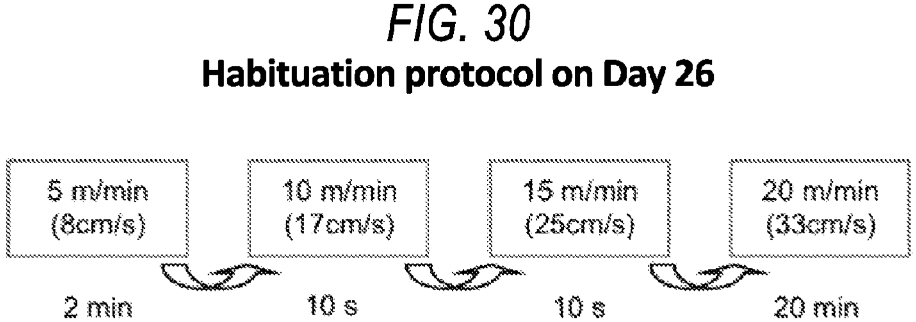
FIG. 30 depicts habituation protocol on day 26.

Example 16a: Forced Treadmill Test 75 mice (group 1-5) were tested on the treadmill with a previously optimized protocol as described below. The mice were habituized to the treadmill at two separate occasions, with a habituation protocol. Habituation protocol on day is shown in FIG. 30.

Mice were allowed to acclimate to the testing room for at least 30 min before tested. Mice were initially placed on a treadmill running at 5 m/min for 2 minutes. The treadmill belt was set horizontally. The treadmill speed was then increased to 20 m/min in 20 seconds at steps of 5 m/min in every 10 sec with the shocking grid set at 0.2 mA. Mice were allowed to run for 20 minutes.

Figure 31:
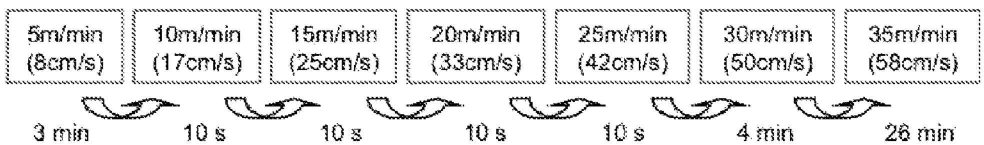
FIG. 31 depicts habituation protocol on day 30.

The test protocol of endurance test with forced treadmill is shown in FIG. 31.

Mice were allowed to acclimate to the testing room for at least 30 min before tested. Mice were initially placed on a treadmill running at 5 m/min for 3 minutes. The treadmill belt was set at 15° C. The treadmill speed was then increased to 30 m/min in 40 seconds at steps of 5 m/min in every 10 sec after 4 min of running at 30 m/min; speed was increased to 35 m/min. The speed was held constant at 35 m/min until exhaustion or until the cutoff at 30 minutes. The treadmill with the shocking grid set at 0.2 mA. The total running time until exhaustion was recorded. Exhaustion was defined as "the mouse stayed on the shock grid for >15 seconds." The shocking grid was set at 0.4 mA on days of test.

Figure 32:
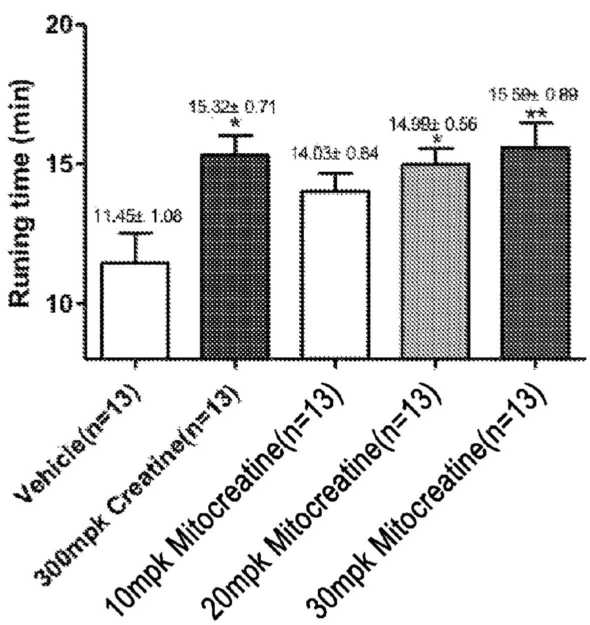
FIG. 32 depicts a bar graph showing the running time of a group of C57BL/6J mice upon treatment with creatine and Mitocreatine for 29 days.

C57BL/6Jmice were treated with creatine (300 mpk, p.o.) and Mitocreatine (10, 20, 30 mpk, p.o.) for 29 days and vehicle was used as control. Total running time of group 1-5 after 30 days treatment. Mice with two outliers are excluded in Vehicle group and the two mice with the best performance in each treatment group are excluded to keep the same group size. Data were expressed as Mean±S.E.M. and analyzed with one-way ANOVA followed by Bonferroni test compared to vehicle group, $*P<0.05$, $P<0.01$ (FIG. 32**).

Example 16b: Fore-Limb Grip Strength Test

One hundred female mice were tested before dosing for a baseline of grip strength. 75 mice were selected and randomly assigned into 5 groups for different treatment.

Seventy five mice (group 1-5) were test on day 31. Mice were allowed to acclimate to the testing room for at least 30 min before tested. All animals were marked on the tail with a permanent mark pen. Mouse was lowered towards the grid on the push-pull gauge until it grabbed with both front paws Animal was gently pulled backwards by the tail with an angle less than 15° until it released its grip of both fore-paws. The maximal fore-limb grip force was recorded on the strain gauge.

Test was repeated 3 times with 15 min interval each time and the average was used.

Figure 33:
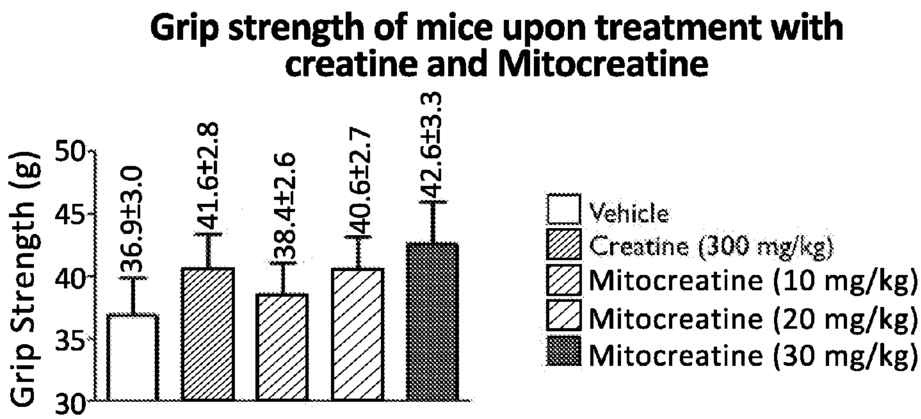
FIG. 33 depicts a bar graph showing the grip strength of a group of C57BL/6J mice upon treatment with creatine and Mitocreatine at various concentrations for 30 days.

FIG. 33 shows fore limb grip force after 30 days: $DH_2O$ (p.o.), Creatine (300mpk, p.o.) and Mitocreatine (10, 20, 30 mpk, p.o.) treatment of C57BL/6Jmice for 30 days. Mice were tested three times in succession with 15 min rest and the results of the three tests were averaged for each mouse.

Example 17: Effect of Mitocreatine on ARPE-19 Cells (a Retinal Pigmented Epithelial Cell Line)

Age related macular degeneration (AMD) is a common eye condition and the leading cause of vision loss among people age 50 and older. AMD is commonly divided into two major forms, namely non-exudative (or more commonly referred to as dry) form and exudative (wet) form. Wet AMD is characterized by an increase of blood vessel growth. It is treated with anti-angiogenesis drugs such as anti-VEGF antibody injections. The less sever and far more common dry form of AMD present a very large unmet medical need as no procedures or drugs currently exist to treat the condition.

Oxidative stress and cellular senescence of retinal pigment epithelial appears to play a major role in the disease progression of AMD (Kozlowski 2012 and Beatty, Stephen, et al. 2000).

In the present invention ARPE-19 cells were used to evaluate whether Mitocreatine improves mitochondrial parameters and reduces ROS in a cell model of AMD. The cells were prematurely senescenced according to the protocol of Glotin et al. (2008).

Example 17a: Mitocreatine is not Toxic to Senescent ARPE-19 Cells

Figure 34:
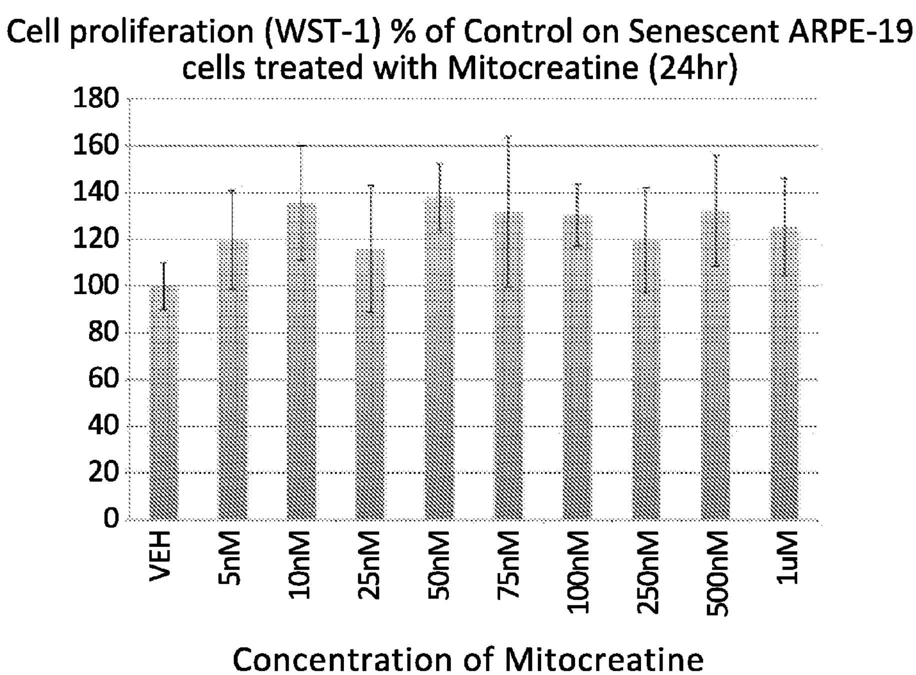
FIG. 34 depicts a bar graph showing the effect of cell proliferation of ARPE-19 (human retinal pigment epithelium cells) upon treatment with Mitocreatine at various concentrations for 24 hours.

As shown in FIG. 34, ARPE-19 cells, a retinal pigmented epithelial cell line, were prematurely senesced according to the protocol of Glotin et al. (2008). Cells were plated in a 96 well plate for analysis of WST-1 bioreduction, a formazan based dye similar to MTT whose bioreduction is largely dependent on the glycolytic production of NAD(P)H in viable cells and is routinely used to monitor cell viability. Twenty-four hours after treatment with increasing concentrations of Mitocreatine, cells were incubated with WST-1 for four hours and assayed using a colorimetric plate reader at an absorbance of 450 nm Mitocreatine up to 1 uM does not negatively impact cell viability.

Figure 35:
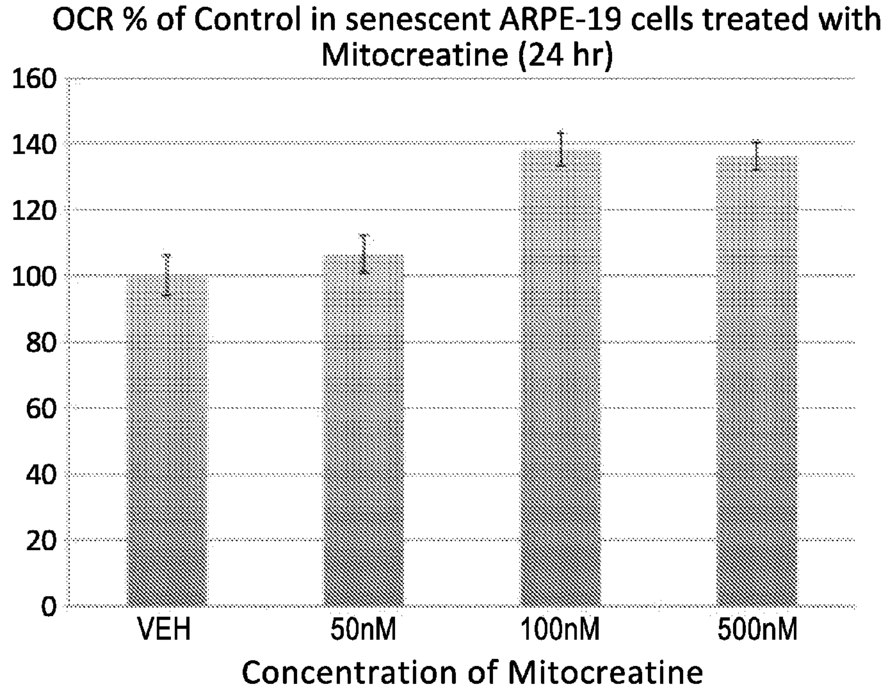
FIG. 35 depicts a bar graph showing the percent increase in oxygen consumption rate (% OCR) upon addition of various concentrations of Mitocreatine to ARPE-19 cells.

Example 17b: Mitocreatine Increases Basal Oxygen Consumption in Senescent ARPE-19 Cells As shown in FIG. 35, ARPE-19 cells, a retinal pigmented epithelial cell line, were prematurely senesced according to the protocol of Glotin et al. (2008). Cells were plated in a XF24 (Seahorse Biosciences) plate for analysis of mitochondrial activities. Twenty-four hours before analysis in the XF24 instrument, cells were treated with increasing concentrations on mitocreatine and vehicle. Twenty-four hours after treatment basal oxygen consumption rates (OCR) were assayed. A dose-dependent increase in basal oxygen consumption in senescent ARPE-19 cells was observed.

Figure 36:
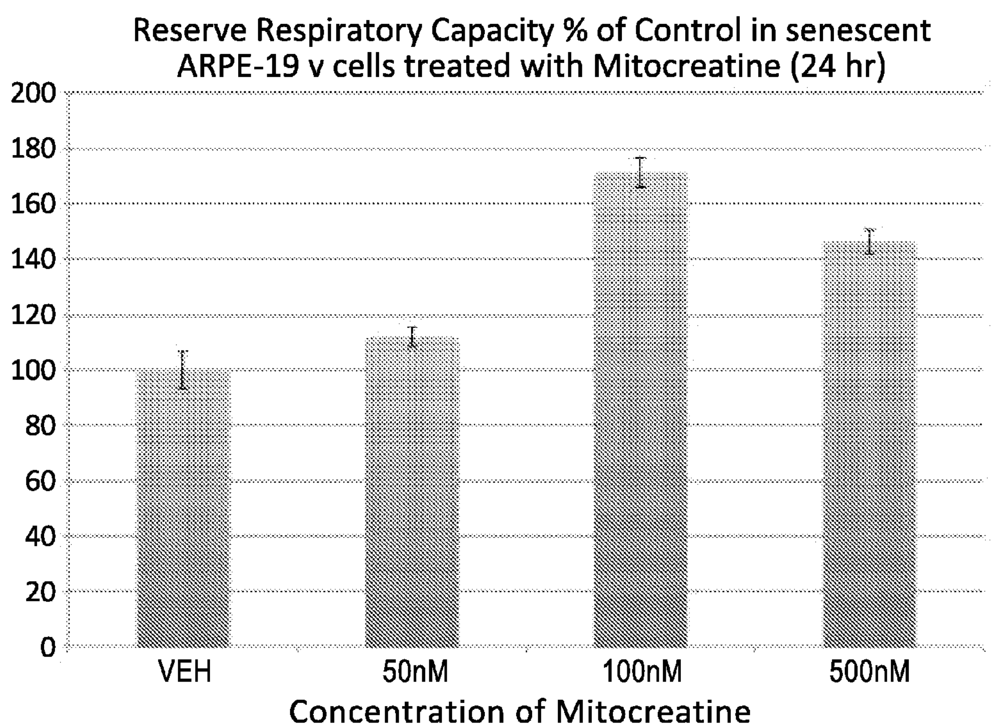
FIG. 36 depicts a bar graph showing percent of reserve respiratory capacity upon treatment of ARPE-19 cells with Mitocreatine at various concentrations.

Example 17c: Mitocreatine Increases Maximal Respiration Rates in Senescent ARPE-19 Cells As shown in FIG. 36, ARPE-19 cells, a retinal pigmented epithelial cell line, were prematurely senesced according to the protocol of Glotin et al. (2008). Cells were plated in a XF24 (Seahorse Biosciences) plate for analysis of mitochondrial activities. Twenty-four hours before analysis in the XF24 instrument, cells were treated with increasing concentrations on mitocreatine and vehicle. Twenty-four hours after treatment FCCP-stimulated oxygen consumption rates (maximal OCR) were assayed. There is a dose-dependent increase in maximal oxygen consumption in senescent ARPE-19 cells.

Figure 37:
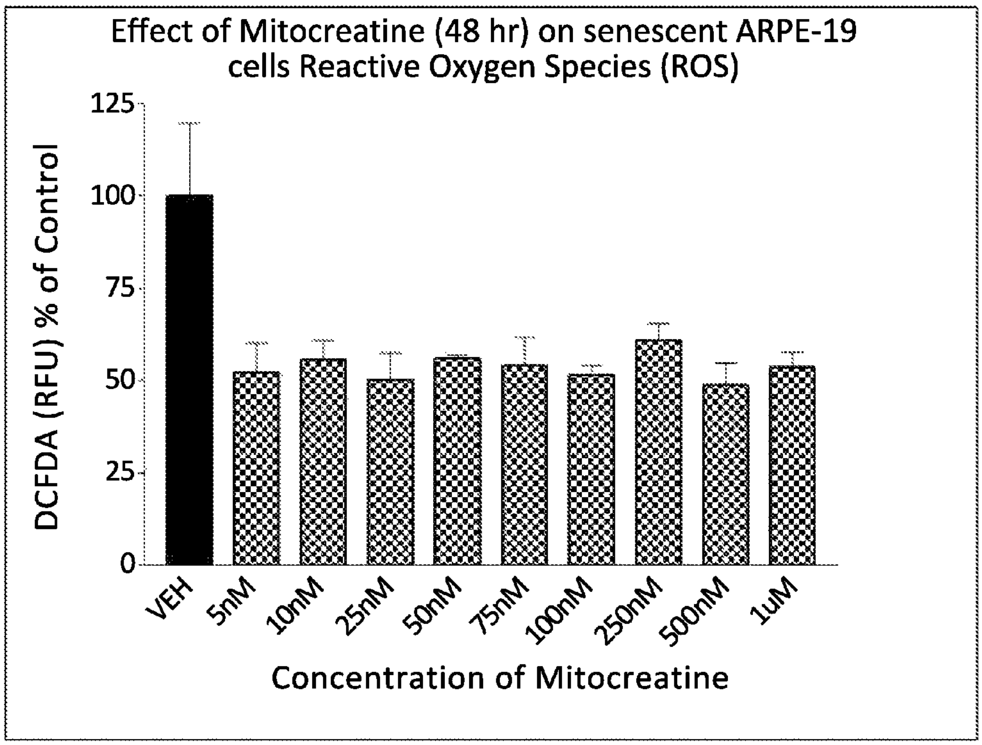
FIG. 37 depicts a bar graph showing the reactive oxygen species (ROS) upon treatment of ARPE-19 cells with Mitocreatine at various concentrations.

Example 17d: Mitocreatine Reduces Cellular ROS Production in Senescent ARPE-19 Cells ARPE-19 cells, a retinal pigmented epithelial cell line, were prematurely senesced according to the protocol of Glotin et al. (2008). Cells were plated in a 96 well plate for analysis of reactive oxygen species (ROS) production using DCFDA, a fluorogenic dye that is oxidized by hydroxyl, peroxyl and other ROS. Forty-eight hours after treatment with increasing concentrations of mitocreatine, cells were incubated with DCFDA and assayed using a fluorescent plate reader with excitation and emission spectra of 495 nm and 529 nm There is a dose-independent decrease in ROS production in senescent ARPE-19 cells (FIG. 37).

Accordingly, mitocreatine and its analogous are useful for treating or preventing age related macular degeneration in a patient. Mitocreatine can increase the mitochondrial activity of the eye.

VII. Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

We claim:

1. A method for treating or alleviating wrinkles in an individual in need thereof, the method comprises administering to the individual an effective amount of a compound of Formula I:

I

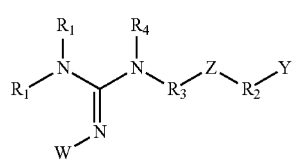

or a pharmaceutically acceptable salt thereof wherein

Z is —C(═O)$NR_5$—;

Y is a phosphonium group;

each $R_1$ is hydrogen;

$R_2$ is alkyl;

$R_3$ is alkyl, alkylcycloalkyl, or alkylheterocycloalkyl;

$R_4$ is $C_{1-6}$ alkyl;

$R_5$ is hydrogen, or alkyl; and W is hydrogen.

2. The method of claim 1, wherein $R_5$ is hydrogen, or $C_{1-6}$ alkyl.

3. The method of claim 1, wherein Z is —C(═O)NH—.

4. The method of claim 1, wherein the phosphonium group is selected from $P^+(R')_3X^-$, wherein R' is alkyl or aryl; and $X^-$ is a pharmaceutically acceptable anion.

5. The method of claim 4, wherein R' is phenyl; and $X^-$ is chloride, or trifluoroacetate.

6. The method of claim 1, wherein $R^5$ is methyl.

7. The method of claim 1, wherein $R_2$ is $C_{3-8}$ alkyl.

8. The method of claim 1, wherein $R_3$ is $C_{1-8}$ alkyl.

9. The method of claim 1, wherein $R_4$ is methyl.

10. The method of claim 1, wherein

Z is —C(═O)$NR_5$—, wherein $R_5$ is hydrogen, or methyl;

Y is —$P^+(R')_3X^-$, wherein R' is alkyl or aryl; $X^-$ is chloride, or trifluoroacetate;

each $R_1$ is hydrogen;

$R_2$ is $C_{1-8}$ alkyl;

$R_3$ is $C_{1-8}$ alkyl, $R_4$ is methyl; and W is hydrogen.

11. The method of claim 1, wherein Z is —C(═O)NH, each $R_1$ is hydrogen, $R_2$ is $C_{1-8}$ alkyl; $R_3$ is $C_{1-8}$alkyl; and $R_4$ is methyl.

12. The method of claim 1, wherein the compound of Formula I is selected from:

$N^2$-[amino(imino)methyl]-$N^2$-methyl-N-[3-(triphenylphosphonio) propyl]glycinamide chloride;

$N^2$-[ammonio(imino)methyl]-N,$N^2$-dimethyl-N-[3-(triphenylphosphonio) propyl]glycinamide bis(trifluoroacetate);

$N^2$-[ammonio(imino)methyl]-$N^2$-methyl-N-[3-(triphenylphosphonio)propyl]glycinamide bis(trifluoroacetate);

$N^2$-[ammonio(imino)methyl]-$N^2$-methyl-N-[3-(triphenylphosphonio)propyl] glycinamide dichloride;

$N^3$-[amino(imino)methyl]-$N^3$-methyl-N-[4-(triphenylphosphonio) butyl]-β-alaninamide trifluoroacetate-trifluoroacetic acid;

{4-[(4-{[amino(imino) methyl](methyl)amino}butanoyl) amino] butyl}(triphenyl)phosphonium trifluoroacetate-trifluoroacetic acid;

{4-[(4-{[amino(imino)methyl](methyl)amino}-2,2-dimethylbutanoyl)amino]butyl}(triphenyl)phosphonium trifluoroacetate-trifluoroacetic acid;

[3-({[1-({[amino(imino)methyl](methyl)amino}methyl) cyclopropyl]carbonyl}amino)propyl](triphenyl)phosphonium trifluoroacetate-trifluoroacetic acid; or

[3-({[4-({[amino(imino)methyl](methyl)amino}methyl) tetrahydro-2H-pyran-4-yl]carbonyl}amino)propyl](triphenyl)phosphonium trifluoroacetate-trifluoroacetic acid.

13. The method of claim 1, wherein the wrinkles are symptoms of aged skin or sun damaged skin.

14. The method of claim 1, wherein the compound of Formula I is

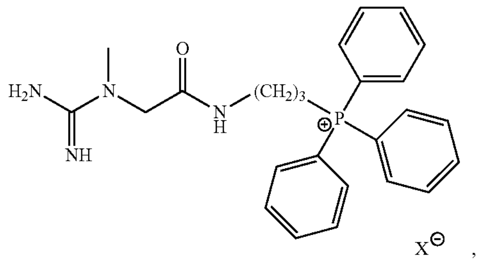

wherein $X^-$ is chloride or trifluoroacetate.

15. The method of claim 1, wherein the pharmaceutically acceptable salt of the compound of Formula I is

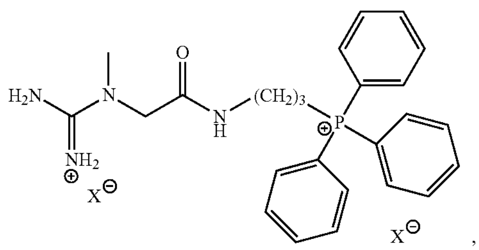

wherein each $X^-$ is chloride or trifluoroacetate.

16. The method of claim 1, wherein the compound of Formula I is

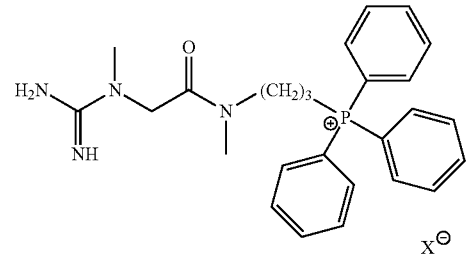

wherein $X^-$ is chloride or trifluoroacetate.

17. The method of claim 1, wherein the pharmaceutically acceptable salt of the compound of Formula I is

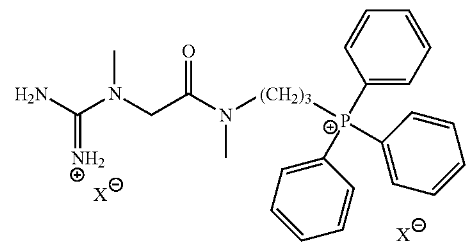

wherein each $X^-$ is chloride or trifluoroacetate.

* * * * *

SEQUENCE LISTING

```
<160> NUMBER OF SEQ ID NOS: 36

<210> SEQ ID NO 1
<211> LENGTH: 246
<212> TYPE: PRT
<213> ORGANISM: Homo sapiens

<400> SEQUENCE: 1

Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe Ser Ser Val Leu Ala Ser
        35                  40                  45

Cys Pro Lys Lys Pro Val Ser Ser Tyr Leu Arg Phe Ser Lys Glu Gln
    50                  55                  60

Leu Pro Ile Phe Lys Ala Gln Asn Pro Asp Ala Lys Thr Thr Glu Leu
65                  70                  75                  80

Ile Arg Arg Ile Ala Gln Arg Trp Arg Glu Leu Pro Asp Ser Lys Lys
                85                  90                  95

Lys Ile Tyr Gln Asp Ala Tyr Arg Ala Glu Trp Gln Val Tyr Lys Glu
            100                 105                 110

Glu Ile Ser Arg Phe Lys Glu Gln Leu Thr Pro Ser Gln Ile Met Ser
        115                 120                 125

Leu Glu Lys Glu Ile Met Asp Lys His Leu Lys Arg Lys Ala Met Thr
    130                 135                 140

Lys Lys Lys Glu Leu Thr Leu Leu Gly Lys Pro Lys Arg Pro Arg Ser
145                 150                 155                 160

Ala Tyr Asn Val Tyr Val Ala Glu Arg Phe Gln Glu Ala Lys Gly Asp
                165                 170                 175

Ser Pro Gln Glu Lys Leu Lys Thr Val Lys Glu Asn Trp Lys Asn Leu
            180                 185                 190

Ser Asp Ser Glu Lys Glu Leu Tyr Ile Gln His Ala Lys Glu Asp Glu
        195                 200                 205

Thr Arg Tyr His Asn Glu Met Lys Ser Trp Glu Glu Gln Met Ile Glu
    210                 215                 220

Val Gly Arg Lys Asp Leu Leu Arg Arg Thr Ile Lys Lys Gln Arg Lys
225                 230                 235                 240

Tyr Gly Ala Glu Glu Cys
                245


<210> SEQ ID NO 2
<211> LENGTH: 42
<212> TYPE: PRT
<213> ORGANISM: Artificial Sequence
<220> FEATURE:
<223> OTHER INFORMATION: synthetic construct - amino acids 1-42 of human
      TFAM

<400> SEQUENCE: 2

Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe
        35                  40
```

-continued

```
<210> SEQ ID NO 3
<211> LENGTH: 204
<212> TYPE: PRT
<213> ORGANISM: Artificial Sequence
<220> FEATURE:
<223> OTHER INFORMATION: synthetic construct

<400> SEQUENCE: 3

Ser Ser Val Leu Ala Ser Cys Pro Lys Lys Pro Val Ser Ser Tyr Leu
1               5                   10                  15

Arg Phe Ser Lys Glu Gln Leu Pro Ile Phe Lys Ala Gln Asn Pro Asp
            20                  25                  30

Ala Lys Thr Thr Glu Leu Ile Arg Arg Ile Ala Gln Arg Trp Arg Glu
        35                  40                  45

Leu Pro Asp Ser Lys Lys Lys Ile Tyr Gln Asp Ala Tyr Arg Ala Glu
    50                  55                  60

Trp Gln Val Tyr Lys Glu Glu Ile Ser Arg Phe Lys Glu Gln Leu Thr
65                  70                  75                  80

Pro Ser Gln Ile Met Ser Leu Glu Lys Glu Ile Met Asp Lys His Leu
                85                  90                  95

Lys Arg Lys Ala Met Thr Lys Lys Lys Glu Leu Thr Leu Leu Gly Lys
            100                 105                 110

Pro Lys Arg Pro Arg Ser Ala Tyr Asn Val Tyr Val Ala Glu Arg Phe
        115                 120                 125

Gln Glu Ala Lys Gly Asp Ser Pro Gln Glu Lys Leu Lys Thr Val Lys
    130                 135                 140

Glu Asn Trp Lys Asn Leu Ser Asp Ser Glu Lys Glu Leu Tyr Ile Gln
145                 150                 155                 160

His Ala Lys Glu Asp Glu Thr Arg Tyr His Asn Glu Met Lys Ser Trp
                165                 170                 175

Glu Glu Gln Met Ile Glu Val Gly Arg Lys Asp Leu Leu Arg Arg Thr
            180                 185                 190

Ile Lys Lys Gln Arg Lys Tyr Gly Ala Glu Glu Cys
        195                 200


<210> SEQ ID NO 4
<211> LENGTH: 346
<212> TYPE: PRT
<213> ORGANISM: Homo sapiens

<400> SEQUENCE: 4

Met Ala Ala Ser Gly Lys Leu Ser Thr Cys Arg Leu Pro Pro Leu Pro
1               5                   10                  15

Thr Ile Arg Glu Ile Ile Lys Leu Leu Arg Leu Gln Ala Ala Asn Glu
            20                  25                  30

Leu Ser Gln Asn Phe Leu Leu Asp Leu Arg Leu Thr Asp Lys Ile Val
        35                  40                  45

Arg Lys Ala Gly Asn Leu Thr Asn Ala Tyr Val Tyr Glu Val Gly Pro
    50                  55                  60

Gly Pro Gly Gly Ile Thr Arg Ser Ile Leu Asn Ala Asp Val Ala Glu
65                  70                  75                  80

Leu Leu Val Val Glu Lys Asp Thr Arg Phe Ile Pro Gly Leu Gln Met
                85                  90                  95

Leu Ser Asp Ala Ala Pro Gly Lys Leu Arg Ile Val His Gly Asp Val
            100                 105                 110

Leu Thr Phe Lys Val Glu Lys Ala Phe Ser Glu Ser Leu Lys Arg Pro
        115                 120                 125
```

```
Trp Glu Asp Asp Pro Pro Asn Val His Ile Ile Gly Asn Leu Pro Phe
    130                 135                 140

Ser Val Ser Thr Pro Leu Ile Ile Lys Trp Leu Glu Asn Ile Ser Cys
145                 150                 155                 160

Arg Asp Gly Pro Phe Val Tyr Gly Arg Thr Gln Met Thr Leu Thr Phe
                165                 170                 175

Gln Lys Glu Val Ala Glu Arg Leu Ala Ala Asn Thr Gly Ser Lys Gln
            180                 185                 190

Arg Ser Arg Leu Ser Val Met Ala Gln Tyr Leu Cys Asn Val Arg His
        195                 200                 205

Ile Phe Thr Ile Pro Gly Gln Ala Phe Val Pro Lys Pro Glu Val Asp
    210                 215                 220

Val Gly Val Val His Phe Thr Pro Leu Ile Gln Pro Lys Ile Glu Gln
225                 230                 235                 240

Pro Phe Lys Leu Val Glu Lys Val Val Gln Asn Val Phe Gln Phe Arg
                245                 250                 255

Arg Lys Tyr Cys His Arg Gly Leu Arg Met Leu Phe Pro Glu Ala Gln
            260                 265                 270

Arg Leu Glu Ser Thr Gly Arg Leu Leu Glu Leu Ala Asp Ile Asp Pro
        275                 280                 285

Thr Leu Arg Pro Arg Gln Leu Ser Ile Ser His Phe Lys Ser Leu Cys
    290                 295                 300

Asp Val Tyr Arg Lys Met Cys Asp Glu Asp Pro Gln Leu Phe Ala Tyr
305                 310                 315                 320

Asn Phe Arg Glu Glu Leu Lys Arg Arg Lys Ser Lys Asn Glu Glu Lys
                325                 330                 335

Glu Glu Asp Asp Ala Glu Asn Tyr Arg Leu
            340                 345


<210> SEQ ID NO 5
<211> LENGTH: 396
<212> TYPE: PRT
<213> ORGANISM: Homo sapiens

<400> SEQUENCE: 5

Met Trp Ile Pro Val Val Gly Leu Pro Arg Arg Leu Arg Leu Ser Ala
1               5                   10                  15

Leu Ala Gly Ala Gly Arg Phe Cys Ile Leu Gly Ser Glu Ala Ala Thr
            20                  25                  30

Arg Lys His Leu Pro Ala Arg Asn His Cys Gly Leu Ser Asp Ser Ser
        35                  40                  45

Pro Gln Leu Trp Pro Glu Pro Asp Phe Arg Asn Pro Pro Arg Lys Ala
    50                  55                  60

Ser Lys Ala Ser Leu Asp Phe Lys Arg Tyr Val Thr Asp Arg Arg Leu
65                  70                  75                  80

Ala Glu Thr Leu Ala Gln Ile Tyr Leu Gly Lys Pro Ser Arg Pro Pro
                85                  90                  95

His Leu Leu Leu Glu Cys Asn Pro Gly Pro Gly Ile Leu Thr Gln Ala
            100                 105                 110

Leu Leu Glu Ala Gly Ala Lys Val Val Ala Leu Glu Ser Asp Lys Thr
        115                 120                 125

Phe Ile Pro His Leu Glu Ser Leu Gly Lys Asn Leu Asp Gly Lys Leu
    130                 135                 140

Arg Val Ile His Cys Asp Phe Phe Lys Leu Asp Pro Arg Ser Gly Gly
```

```
145                 150                 155                 160

Val Ile Lys Pro Pro Ala Met Ser Ser Arg Gly Leu Phe Lys Asn Leu
                165                 170                 175

Gly Ile Glu Ala Val Pro Trp Thr Ala Asp Ile Pro Leu Lys Val Val
            180                 185                 190

Gly Met Phe Pro Ser Arg Gly Glu Lys Arg Ala Leu Trp Lys Leu Ala
        195                 200                 205

Tyr Asp Leu Tyr Ser Cys Thr Ser Ile Tyr Lys Phe Gly Arg Ile Glu
    210                 215                 220

Val Asn Met Phe Ile Gly Glu Lys Glu Phe Gln Lys Leu Met Ala Asp
225                 230                 235                 240

Pro Gly Asn Pro Asp Leu Tyr His Val Leu Ser Val Ile Trp Gln Leu
                245                 250                 255

Ala Cys Glu Ile Lys Val Leu His Met Glu Pro Trp Ser Ser Phe Asp
            260                 265                 270

Ile Tyr Thr Arg Lys Gly Pro Leu Glu Asn Pro Lys Arg Arg Glu Leu
        275                 280                 285

Leu Asp Gln Leu Gln Gln Lys Leu Tyr Leu Ile Gln Met Ile Pro Arg
    290                 295                 300

Gln Asn Leu Phe Thr Lys Asn Leu Thr Pro Met Asn Tyr Asn Ile Phe
305                 310                 315                 320

Phe His Leu Leu Lys His Cys Phe Gly Arg Arg Ser Ala Thr Val Ile
                325                 330                 335

Asp His Leu Arg Ser Leu Thr Pro Leu Asp Ala Arg Asp Ile Leu Met
            340                 345                 350

Gln Ile Gly Lys Gln Glu Asp Glu Lys Val Val Asn Met His Pro Gln
        355                 360                 365

Asp Phe Lys Thr Leu Phe Glu Thr Ile Glu Arg Ser Lys Asp Cys Ala
    370                 375                 380

Tyr Lys Trp Leu Tyr Asp Glu Thr Leu Glu Asp Arg
385                 390                 395


<210> SEQ ID NO 6
<211> LENGTH: 10
<212> TYPE: DNA
<213> ORGANISM: Artificial Sequence
<220> FEATURE:
<223> OTHER INFORMATION: synthetic construct - DNA-binding site of SOX9

<400> SEQUENCE: 6

agaacaatgg                                                            10


<210> SEQ ID NO 7
<211> LENGTH: 11
<212> TYPE: PRT
<213> ORGANISM: Artificial Sequence
<220> FEATURE:
<223> OTHER INFORMATION: synthetic construct-TAT protein transduction
      domain

<400> SEQUENCE: 7

Tyr Gly Arg Lys Lys Arg Arg Gln Arg Arg Arg
1               5                   10


<210> SEQ ID NO 8
<211> LENGTH: 9
<212> TYPE: PRT
<213> ORGANISM: Artificial Sequence
<220> FEATURE:
```

-continued

```
<223> OTHER INFORMATION: synthetic construct-basic domain of TAT protein
      transduction domain

<400> SEQUENCE: 8

Arg Lys Lys Arg Arg Gln Arg Arg Arg
1               5


<210> SEQ ID NO 9
<211> LENGTH: 7
<212> TYPE: PRT
<213> ORGANISM: Artificial Sequence
<220> FEATURE:
<223> OTHER INFORMATION: synthetic construct - poly-ARG

<400> SEQUENCE: 9

Arg Arg Arg Arg Arg Arg Arg
1               5


<210> SEQ ID NO 10
<211> LENGTH: 12
<212> TYPE: PRT
<213> ORGANISM: Artificial Sequence
<220> FEATURE:
<223> OTHER INFORMATION: synthetic construct - protein transduction
      domain

<400> SEQUENCE: 10

Arg Arg Gln Arg Arg Thr Ser Lys Leu Met Lys Arg
1               5                   10


<210> SEQ ID NO 11
<211> LENGTH: 27
<212> TYPE: PRT
<213> ORGANISM: Artificial Sequence
<220> FEATURE:
<223> OTHER INFORMATION: synthetic construct - protein transduction
      domain

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25


<210> SEQ ID NO 12
<211> LENGTH: 29
<212> TYPE: PRT
<213> ORGANISM: Artificial Sequence
<220> FEATURE:
<223> OTHER INFORMATION: synthetic construct - protein transduction
      domain

<400> SEQUENCE: 12

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25


<210> SEQ ID NO 13
<211> LENGTH: 16
<212> TYPE: PRT
<213> ORGANISM: Artificial Sequence
<220> FEATURE:
<223> OTHER INFORMATION: synthetic construct - protein transduction
      domain

<400> SEQUENCE: 13
```

```
Arg Gln Ile Lys Ile Trp Phe Gln Asn Arg Arg Met Lys Trp Lys Lys
1               5                   10                  15


<210> SEQ ID NO 14
<211> LENGTH: 20
<212> TYPE: PRT
<213> ORGANISM: Artificial Sequence
<220> FEATURE:
<223> OTHER INFORMATION: synthetic construct - endosomal escape sequence

<400> SEQUENCE: 14

Gly Asp Ile Met Gly Glu Trp Gly Asn Glu Ile Phe Gly Ala Ile Ala
1               5                   10                  15

Gly Phe Leu Gly
            20


<210> SEQ ID NO 15
<211> LENGTH: 35
<212> TYPE: PRT
<213> ORGANISM: Artificial Sequence
<220> FEATURE:
<223> OTHER INFORMATION: synthetic construct - protein transduction
      domain including an endosomal escape sequence

<400> SEQUENCE: 15

Arg Arg Arg Arg Arg Arg Arg Arg Arg Arg Arg Gly Glu Gly Asp Ile
1               5                   10                  15

Met Gly Glu Trp Gly Asn Glu Ile Phe Gly Ala Ile Ala Gly Phe Leu
            20                  25                  30

Gly Gly Glu
        35


<210> SEQ ID NO 16
<211> LENGTH: 19
<212> TYPE: PRT
<213> ORGANISM: Artificial Sequence
<220> FEATURE:
<223> OTHER INFORMATION: synthetic construct - predicted targeting
      sequence from Etfa

<400> SEQUENCE: 16

Met Phe Arg Ala Ala Ala Pro Gly Gln Leu Arg Arg Ala Ala Ser Leu
1               5                   10                  15

Leu Arg Phe


<210> SEQ ID NO 17
<211> LENGTH: 35
<212> TYPE: PRT
<213> ORGANISM: Artificial Sequence
<220> FEATURE:
<223> OTHER INFORMATION: synthetic construct - predicted mitochondrial
      targeting signal from Dld

<400> SEQUENCE: 17

Met Gln Ser Trp Ser Arg Val Tyr Cys Ser Leu Ala Lys Arg Gly His
1               5                   10                  15

Phe Asn Arg Ile Ser His Gly Leu Gln Gly Leu Ser Ala Val Pro Leu
            20                  25                  30

Arg Thr Tyr
        35


<210> SEQ ID NO 18
<211> LENGTH: 24
```

```
<212> TYPE: PRT
<213> ORGANISM: Artificial Sequence
<220> FEATURE:
<223> OTHER INFORMATION: synthetic construct - SOD2 mitochondrial
      targeting signal

<400> SEQUENCE: 18

Met Leu Ser Arg Ala Val Cys Gly Thr Ser Arg Gln Leu Ala Pro Val
1               5                   10                  15

Leu Gly Tyr Leu Gly Ser Arg Gln
            20


<210> SEQ ID NO 19
<211> LENGTH: 23
<212> TYPE: PRT
<213> ORGANISM: Artificial Sequence
<220> FEATURE:
<223> OTHER INFORMATION: synthetic construct - SOD2 mitochondrial
      targeting signal

<400> SEQUENCE: 19

Leu Ser Arg Ala Val Cys Gly Thr Ser Arg Gln Leu Ala Pro Val Leu
1               5                   10                  15

Gly Tyr Leu Gly Ser Arg Gln
            20


<210> SEQ ID NO 20
<211> LENGTH: 24
<212> TYPE: PRT
<213> ORGANISM: Artificial Sequence
<220> FEATURE:
<223> OTHER INFORMATION: synthetic construct - SOD2 mitochondrial
      targeting signal

<400> SEQUENCE: 20

Met Leu Ser Arg Ala Val Cys Gly Thr Ser Arg Gln Leu Ala Pro Val
1               5                   10                  15

Leu Gly Tyr Leu Gly Ser Arg Gln
            20


<210> SEQ ID NO 21
<211> LENGTH: 23
<212> TYPE: PRT
<213> ORGANISM: Artificial Sequence
<220> FEATURE:
<223> OTHER INFORMATION: synthetic construct - SOD2 mitochondrial
      targeting signal

<400> SEQUENCE: 21

Leu Ser Arg Ala Val Cys Gly Thr Ser Arg Gln Leu Ala Pro Val Leu
1               5                   10                  15

Gly Tyr Leu Gly Ser Arg Gln
            20


<210> SEQ ID NO 22
<211> LENGTH: 259
<212> TYPE: PRT
<213> ORGANISM: Artificial Sequence
<220> FEATURE:
<223> OTHER INFORMATION: synthetic construct - recombinant fusion
      protein

<400> SEQUENCE: 22

Met Ala Arg Arg Arg Arg Arg Arg Arg Arg Arg Arg Arg Met Ala Phe
1               5                   10                  15
```

```
Leu Arg Ser Met Trp Gly Val Leu Ser Ala Leu Gly Arg Ser Gly Ala
            20                  25                  30

Glu Leu Cys Thr Gly Cys Gly Ser Arg Leu Arg Ser Pro Phe Ser Phe
        35                  40                  45

Val Tyr Leu Pro Arg Trp Phe Ser Ser Val Leu Ala Ser Cys Pro Lys
    50                  55                  60

Lys Pro Val Ser Ser Tyr Leu Arg Phe Ser Lys Glu Gln Leu Pro Ile
65                  70                  75                  80

Phe Lys Ala Gln Asn Pro Asp Ala Lys Thr Thr Glu Leu Ile Arg Arg
                85                  90                  95

Ile Ala Gln Arg Trp Arg Glu Leu Pro Asp Ser Lys Lys Lys Ile Tyr
            100                 105                 110

Gln Asp Ala Tyr Arg Ala Glu Trp Gln Val Tyr Lys Glu Glu Ile Ser
        115                 120                 125

Arg Phe Lys Glu Gln Leu Thr Pro Ser Gln Ile Met Ser Leu Glu Lys
    130                 135                 140

Glu Ile Met Asp Lys His Leu Lys Arg Lys Ala Met Thr Lys Lys Lys
145                 150                 155                 160

Glu Leu Thr Leu Leu Gly Lys Pro Lys Arg Pro Arg Ser Ala Tyr Asn
                165                 170                 175

Val Tyr Val Ala Glu Arg Phe Gln Glu Ala Lys Gly Asp Ser Pro Gln
            180                 185                 190

Glu Lys Leu Lys Thr Val Lys Glu Asn Trp Lys Asn Leu Ser Asp Ser
        195                 200                 205

Glu Lys Glu Leu Tyr Ile Gln His Ala Lys Glu Asp Glu Thr Arg Tyr
    210                 215                 220

His Asn Glu Met Lys Ser Trp Glu Glu Gln Met Ile Glu Val Gly Arg
225                 230                 235                 240

Lys Asp Leu Leu Arg Arg Thr Ile Lys Lys Gln Arg Lys Tyr Gly Ala
                245                 250                 255

Glu Glu Cys


<210> SEQ ID NO 23
<211> LENGTH: 258
<212> TYPE: PRT
<213> ORGANISM: Artificial Sequence
<220> FEATURE:
<223> OTHER INFORMATION: synthetic construct - recombinant fusion
      protein

<400> SEQUENCE: 23

Ala Arg Arg Arg Arg Arg Arg Arg Arg Arg Arg Arg Met Ala Phe Leu
1               5                   10                  15

Arg Ser Met Trp Gly Val Leu Ser Ala Leu Gly Arg Ser Gly Ala Glu
            20                  25                  30

Leu Cys Thr Gly Cys Gly Ser Arg Leu Arg Ser Pro Phe Ser Phe Val
        35                  40                  45

Tyr Leu Pro Arg Trp Phe Ser Ser Val Leu Ala Ser Cys Pro Lys Lys
    50                  55                  60

Pro Val Ser Ser Tyr Leu Arg Phe Ser Lys Glu Gln Leu Pro Ile Phe
65                  70                  75                  80

Lys Ala Gln Asn Pro Asp Ala Lys Thr Thr Glu Leu Ile Arg Arg Ile
                85                  90                  95

Ala Gln Arg Trp Arg Glu Leu Pro Asp Ser Lys Lys Lys Ile Tyr Gln
            100                 105                 110
```

```
Asp Ala Tyr Arg Ala Glu Trp Gln Val Tyr Lys Glu Glu Ile Ser Arg
        115                 120                 125

Phe Lys Glu Gln Leu Thr Pro Ser Gln Ile Met Ser Leu Glu Lys Glu
    130                 135                 140

Ile Met Asp Lys His Leu Lys Arg Lys Ala Met Thr Lys Lys Lys Glu
145                 150                 155                 160

Leu Thr Leu Leu Gly Lys Pro Lys Arg Pro Arg Ser Ala Tyr Asn Val
                165                 170                 175

Tyr Val Ala Glu Arg Phe Gln Glu Ala Lys Gly Asp Ser Pro Gln Glu
            180                 185                 190

Lys Leu Lys Thr Val Lys Glu Asn Trp Lys Asn Leu Ser Asp Ser Glu
        195                 200                 205

Lys Glu Leu Tyr Ile Gln His Ala Lys Glu Asp Glu Thr Arg Tyr His
    210                 215                 220

Asn Glu Met Lys Ser Trp Glu Glu Gln Met Ile Glu Val Gly Arg Lys
225                 230                 235                 240

Asp Leu Leu Arg Arg Thr Ile Lys Lys Gln Arg Lys Tyr Gly Ala Glu
                245                 250                 255

Glu Cys
```

<210> SEQ ID NO 24
<211> LENGTH: 780
<212> TYPE: DNA
<213> ORGANISM: Artificial Sequence
<220> FEATURE:
<223> OTHER INFORMATION: synthetic construct - nucleic acid encoding a recombinant fusion protein

<400> SEQUENCE: 24

```
atggcgcgtc gtcgtcgtcg tcgtcgtcgt cgtcgtcgta tggcgtttct ccgaagcatg     60

tggggcgtgc tgagtgccct gggaaggtct ggagcagagc tgtgcaccgg ctgtggaagt    120

cgactgcgct ccccttcag ttttgtgtat ttaccgaggt ggttttcatc tgtcttggca    180

agttgtccaa agaaacctgt aagttcttac cttcgatttt ctaaagaaca actacccata    240

tttaaagctc agaacccaga tgcaaaaact acagaactaa ttagaagaat tgcccagcgt    300

tggagggaac ttcctgattc aaagaaaaaa atatatcaag atgcttatag ggcggagtgg    360

caggtatata aagaagagat aagcagattt aaagaacagc taactccaag tcagattatg    420

tctttggaaa aagaaatcat ggacaaacat ttaaaaagga aagctatgac aaaaaaaaaa    480

gagttaacac tgcttggaaa accaaaaaga cctcgttcag cttataacgt ttatgtagct    540

gaaagattcc aagaagctaa gggtgattca ccgcaggaaa agctgaagac tgtaaaggaa    600

aactggaaaa atctgtctga ctctgaaaag gaattatata ttcagcatgc taaagaggac    660

gaaactcgtt atcataatga aatgaagtct tgggaagaac aaatgattga agttggacga    720

aaggatcttc tacgtcgcac aataaagaaa caacgaaaat atggtgctga ggagtgttaa    780
```

<210> SEQ ID NO 25
<211> LENGTH: 264
<212> TYPE: PRT
<213> ORGANISM: Artificial Sequence
<220> FEATURE:
<223> OTHER INFORMATION: synthetic construct - recombinant fusion protein

<400> SEQUENCE: 25

```
Met Arg Arg Arg Arg Arg Arg Arg Arg Arg Arg Arg Gly Glu Gly Asp
1               5                   10                  15
```

```
Ile Met Gly Glu Trp Gly Asn Glu Ile Phe Gly Ala Ile Ala Gly Phe
            20                  25                  30

Leu Gly Gly Glu Met Leu Ser Arg Ala Val Cys Gly Thr Ser Arg Gln
        35                  40                  45

Leu Pro Pro Val Leu Gly Tyr Leu Gly Ser Arg Gln Ser Ser Val Leu
    50                  55                  60

Ala Ser Cys Pro Lys Lys Pro Val Ser Ser Tyr Leu Arg Phe Ser Lys
65                  70                  75                  80

Glu Gln Leu Pro Ile Phe Lys Ala Gln Asn Pro Asp Ala Lys Thr Thr
                85                  90                  95

Glu Leu Ile Arg Arg Ile Ala Gln Arg Trp Arg Glu Leu Pro Asp Ser
            100                 105                 110

Lys Lys Lys Ile Tyr Gln Asp Ala Tyr Arg Ala Glu Trp Gln Val Tyr
        115                 120                 125

Lys Glu Glu Ile Ser Arg Phe Lys Glu Gln Leu Thr Pro Ser Gln Ile
    130                 135                 140

Met Ser Leu Glu Lys Glu Ile Met Asp Lys His Leu Lys Arg Lys Ala
145                 150                 155                 160

Met Thr Lys Lys Lys Glu Leu Thr Leu Leu Gly Lys Pro Lys Arg Pro
                165                 170                 175

Arg Ser Ala Tyr Asn Val Tyr Val Ala Glu Arg Phe Gln Glu Ala Lys
            180                 185                 190

Gly Asp Ser Pro Gln Glu Lys Leu Lys Thr Val Lys Glu Asn Trp Lys
        195                 200                 205

Asn Leu Ser Asp Ser Glu Lys Glu Leu Tyr Ile Gln His Ala Lys Glu
    210                 215                 220

Asp Glu Thr Arg Tyr His Asn Glu Met Lys Ser Trp Glu Glu Gln Met
225                 230                 235                 240

Ile Glu Val Gly Arg Lys Asp Leu Leu Arg Arg Thr Ile Lys Lys Gln
                245                 250                 255

Arg Lys Tyr Gly Ala Glu Glu Cys
            260


<210> SEQ ID NO 26
<211> LENGTH: 263
<212> TYPE: PRT
<213> ORGANISM: Artificial Sequence
<220> FEATURE:
<223> OTHER INFORMATION: synthetic construct - recombinant fusion
      protein

<400> SEQUENCE: 26

Arg Arg Arg Arg Arg Arg Arg Arg Arg Arg Arg Gly Glu Gly Asp Ile
1               5                   10                  15

Met Gly Glu Trp Gly Asn Glu Ile Phe Gly Ala Ile Ala Gly Phe Leu
            20                  25                  30

Gly Gly Glu Met Leu Ser Arg Ala Val Cys Gly Thr Ser Arg Gln Leu
        35                  40                  45

Pro Pro Val Leu Gly Tyr Leu Gly Ser Arg Gln Ser Ser Val Leu Ala
    50                  55                  60

Ser Cys Pro Lys Lys Pro Val Ser Ser Tyr Leu Arg Phe Ser Lys Glu
65                  70                  75                  80

Gln Leu Pro Ile Phe Lys Ala Gln Asn Pro Asp Ala Lys Thr Thr Glu
                85                  90                  95

Leu Ile Arg Arg Ile Ala Gln Arg Trp Arg Glu Leu Pro Asp Ser Lys
```

```
            100                 105                 110

Lys Lys Ile Tyr Gln Asp Ala Tyr Arg Ala Glu Trp Gln Val Tyr Lys
        115                 120                 125

Glu Glu Ile Ser Arg Phe Lys Glu Gln Leu Thr Pro Ser Gln Ile Met
    130                 135                 140

Ser Leu Glu Lys Glu Ile Met Asp Lys His Leu Lys Arg Lys Ala Met
145                 150                 155                 160

Thr Lys Lys Lys Glu Leu Thr Leu Leu Gly Lys Pro Lys Arg Pro Arg
                165                 170                 175

Ser Ala Tyr Asn Val Tyr Val Ala Glu Arg Phe Gln Glu Ala Lys Gly
            180                 185                 190

Asp Ser Pro Gln Glu Lys Leu Lys Thr Val Lys Glu Asn Trp Lys Asn
        195                 200                 205

Leu Ser Asp Ser Glu Lys Glu Leu Tyr Ile Gln His Ala Lys Glu Asp
    210                 215                 220

Glu Thr Arg Tyr His Asn Glu Met Lys Ser Trp Glu Glu Gln Met Ile
225                 230                 235                 240

Glu Val Gly Arg Lys Asp Leu Leu Arg Arg Thr Ile Lys Lys Gln Arg
                245                 250                 255

Lys Tyr Gly Ala Glu Glu Cys
            260
```

<210> SEQ ID NO 27
<211> LENGTH: 795
<212> TYPE: DNA
<213> ORGANISM: Artificial Sequence
<220> FEATURE:
<223> OTHER INFORMATION: synthetic construct - nucleic acid encoding recombinant fusion protein

<400> SEQUENCE: 27

```
atgcggcgac gcagacgtcg tcgtcggcgg cgtcgcggcg agggtgatat tatgggtgaa      60

tgggggaacg aaattttcgg agcgatcgct ggttttctcg gtggagaaat gttatcacgc     120

gcggtatgtg gcaccagcag gcagctgcct ccagtccttg gctatctggg ttcccgccag     180

tcatcggtgt tagcatcatg tccgaaaaaa cctgtctcgt cgtacctgcg cttctccaaa     240

gagcagctgc cgatttttaa agcgcaaaat ccggatgcta aaacgactga actgattcgc     300

cgcattgcac aacgctggcg cgaactcccg gacagtaaaa aaaaaattta tcaggacgcc     360

tatcgggctg aatggcaggt ctataaagag gagatctcac gcttcaaaga acaattaacc     420

ccgagtcaaa taatgtctct ggaaaaagaa atcatggata aacacttaaa acgaaaggcg     480

atgacgaaga aaaaagaact gaccctgcta ggtaaaccta agcgtccgcg ctctgcgtat     540

aatgtgtacg tggcagaacg ttttcaggag gccaaagggg attctccgca agaaaaactg     600

aagaccgtca aagaaaattg gaaaaacctg tctgatagcg aaaaagaact gtacattcag     660

cacgctaaag aagatgagac gcggtatcac aacgaaatga aatcttggga agagcagatg     720

atcgaggtcg gtcggaagga tcttctccgt cgaaccatca aaaaacagcg taaatatgga     780

gcagaagagt gctga                                                       795
```

<210> SEQ ID NO 28
<211> LENGTH: 88
<212> TYPE: PRT
<213> ORGANISM: Artificial Sequence
<220> FEATURE:
<223> OTHER INFORMATION: synthetic construct

<400> SEQUENCE: 28

His Asp Glu Ala Gln Gln Asn Ala Phe Tyr Gln Val Leu Asn Met Pro
1 5 10 15

Asn Leu Asn Ala Asp Gln Arg Asn Gly Phe Ile Gln Ser Leu Lys Asp
20 25 30

Asp Pro Ser Gln Ser Ala Asn Val Leu Gly Glu Ala His Asp Glu Ala
35 40 45

Gln Gln Asn Ala Phe Tyr Gln Val Leu Asn Met Pro Asn Leu Asn Ala
50 55 60

Asp Gln Arg Asn Gly Phe Ile Gln Ser Leu Lys Asp Asp Pro Ser Gln
65 70 75 80

Ser Ala Asn Val Leu Gly Glu Ala
85

<210> SEQ ID NO 29
<211> LENGTH: 91
<212> TYPE: PRT
<213> ORGANISM: Artificial Sequence
<220> FEATURE:
<223> OTHER INFORMATION: synthetic construct

<400> SEQUENCE: 29

His Asp Glu Ala Gln Gln Asn Ala Phe Tyr Gln Val Leu Asn Met Pro
1 5 10 15

Asn Leu Asn Ala Asp Gln Arg Asn Gly Phe Ile Gln Ser Leu Lys Asp
20 25 30

Asp Pro Ser Gln Ser Ala Asn Val Leu Gly Glu Ala His Asp Glu Ala
35 40 45

Gln Gln Asn Ala Phe Tyr Gln Val Leu Asn Met Pro Asn Leu Asn Ala
50 55 60

Asp Gln Arg Asn Gly Phe Ile Gln Ser Leu Lys Asp Asp Pro Ser Gln
65 70 75 80

Ser Ala Asn Val Leu Gly Glu Ala Gly Glu Gly
85 90

<210> SEQ ID NO 30
<211> LENGTH: 331
<212> TYPE: PRT
<213> ORGANISM: Artificial Sequence
<220> FEATURE:
<223> OTHER INFORMATION: synthetic construct - recombinant fusion
protein

<400> SEQUENCE: 30

Met Arg Arg Arg Arg Arg Arg Arg Arg Arg Arg Arg Gly Glu Gly Asp
1 5 10 15

Ile Met Gly Glu Trp Gly Asn Glu Ile Phe Gly Ala Ile Ala Gly Phe
20 25 30

Leu Gly Gly Glu His Asp Glu Ala Gln Gln Asn Ala Phe Tyr Gln Val
35 40 45

Leu Asn Met Pro Asn Leu Asn Ala Asp Gln Arg Asn Gly Phe Ile Gln
50 55 60

Ser Leu Lys Asp Asp Pro Ser Gln Ser Ala Asn Val Leu Gly Glu Ala
65 70 75 80

His Asp Glu Ala Gln Gln Asn Ala Phe Tyr Gln Val Leu Asn Met Pro
85 90 95

Asn Leu Asn Ala Asp Gln Arg Asn Gly Phe Ile Gln Ser Leu Lys Asp
100 105 110

```
Asp Pro Ser Gln Ser Ala Asn Val Leu Gly Glu Ala Gly Glu Gly Ser
        115                 120                 125

Ser Val Leu Ala Ser Cys Pro Lys Lys Pro Val Ser Ser Tyr Leu Arg
    130                 135                 140

Phe Ser Lys Glu Gln Leu Pro Ile Phe Lys Ala Gln Asn Pro Asp Ala
145                 150                 155                 160

Lys Thr Thr Glu Leu Ile Arg Arg Ile Ala Gln Arg Trp Arg Glu Leu
                165                 170                 175

Pro Asp Ser Lys Lys Lys Ile Tyr Gln Asp Ala Tyr Arg Ala Glu Trp
            180                 185                 190

Gln Val Tyr Lys Glu Glu Ile Ser Arg Phe Lys Glu Gln Leu Thr Pro
        195                 200                 205

Ser Gln Ile Met Ser Leu Glu Lys Glu Ile Met Asp Lys His Leu Lys
    210                 215                 220

Arg Lys Ala Met Thr Lys Lys Lys Glu Leu Thr Leu Leu Gly Lys Pro
225                 230                 235                 240

Lys Arg Pro Arg Ser Ala Tyr Asn Val Tyr Val Ala Glu Arg Phe Gln
                245                 250                 255

Glu Ala Lys Gly Asp Ser Pro Gln Glu Lys Leu Lys Thr Val Lys Glu
            260                 265                 270

Asn Trp Lys Asn Leu Ser Asp Ser Glu Lys Glu Leu Tyr Ile Gln His
        275                 280                 285

Ala Lys Glu Asp Glu Thr Arg Tyr His Asn Glu Met Lys Ser Trp Glu
    290                 295                 300

Glu Gln Met Ile Glu Val Gly Arg Lys Asp Leu Leu Arg Arg Thr Ile
305                 310                 315                 320

Lys Lys Gln Arg Lys Tyr Gly Ala Glu Glu Cys
                325                 330


<210> SEQ ID NO 31
<211> LENGTH: 330
<212> TYPE: PRT
<213> ORGANISM: Artificial Sequence
<220> FEATURE:
<223> OTHER INFORMATION: synthetic construct - recombinant fusion
      protein

<400> SEQUENCE: 31

Arg Arg Arg Arg Arg Arg Arg Arg Arg Arg Arg Gly Glu Gly Asp Ile
1               5                   10                  15

Met Gly Glu Trp Gly Asn Glu Ile Phe Gly Ala Ile Ala Gly Phe Leu
            20                  25                  30

Gly Gly Glu His Asp Glu Ala Gln Gln Asn Ala Phe Tyr Gln Val Leu
        35                  40                  45

Asn Met Pro Asn Leu Asn Ala Asp Gln Arg Asn Gly Phe Ile Gln Ser
    50                  55                  60

Leu Lys Asp Asp Pro Ser Gln Ser Ala Asn Val Leu Gly Glu Ala His
65                  70                  75                  80

Asp Glu Ala Gln Gln Asn Ala Phe Tyr Gln Val Leu Asn Met Pro Asn
                85                  90                  95

Leu Asn Ala Asp Gln Arg Asn Gly Phe Ile Gln Ser Leu Lys Asp Asp
            100                 105                 110

Pro Ser Gln Ser Ala Asn Val Leu Gly Glu Ala Gly Glu Gly Ser Ser
        115                 120                 125

Val Leu Ala Ser Cys Pro Lys Lys Pro Val Ser Ser Tyr Leu Arg Phe
```

```
    130                 135                 140

Ser Lys Glu Gln Leu Pro Ile Phe Lys Ala Gln Asn Pro Asp Ala Lys
145                 150                 155                 160

Thr Thr Glu Leu Ile Arg Arg Ile Ala Gln Arg Trp Arg Glu Leu Pro
                165                 170                 175

Asp Ser Lys Lys Lys Ile Tyr Gln Asp Ala Tyr Arg Ala Glu Trp Gln
            180                 185                 190

Val Tyr Lys Glu Glu Ile Ser Arg Phe Lys Glu Gln Leu Thr Pro Ser
        195                 200                 205

Gln Ile Met Ser Leu Glu Lys Glu Ile Met Asp Lys His Leu Lys Arg
    210                 215                 220

Lys Ala Met Thr Lys Lys Lys Glu Leu Thr Leu Leu Gly Lys Pro Lys
225                 230                 235                 240

Arg Pro Arg Ser Ala Tyr Asn Val Tyr Val Ala Glu Arg Phe Gln Glu
                245                 250                 255

Ala Lys Gly Asp Ser Pro Gln Glu Lys Leu Lys Thr Val Lys Glu Asn
            260                 265                 270

Trp Lys Asn Leu Ser Asp Ser Glu Lys Glu Leu Tyr Ile Gln His Ala
        275                 280                 285

Lys Glu Asp Glu Thr Arg Tyr His Asn Glu Met Lys Ser Trp Glu Glu
    290                 295                 300

Gln Met Ile Glu Val Gly Arg Lys Asp Leu Leu Arg Arg Thr Ile Lys
305                 310                 315                 320

Lys Gln Arg Lys Tyr Gly Ala Glu Glu Cys
                325                 330


<210> SEQ ID NO 32
<211> LENGTH: 8
<212> TYPE: PRT
<213> ORGANISM: Artificial Sequence
<220> FEATURE:
<223> OTHER INFORMATION: synthetic construct - FLAG tag

<400> SEQUENCE: 32

Asp Tyr Lys Asp Asp Asp Asp Lys
1               5


<210> SEQ ID NO 33
<211> LENGTH: 6
<212> TYPE: PRT
<213> ORGANISM: Artificial Sequence
<220> FEATURE:
<223> OTHER INFORMATION: synthetic construct - haemagglutinin (HA)

<400> SEQUENCE: 33

Tyr Pro Tyr Asp Val Pro
1               5


<210> SEQ ID NO 34
<211> LENGTH: 10
<212> TYPE: PRT
<213> ORGANISM: Artificial Sequence
<220> FEATURE:
<223> OTHER INFORMATION: synthetic construct - MYC tag

<400> SEQUENCE: 34

Ile Leu Lys Lys Ala Thr Ala Tyr Ile Leu
1               5                   10


<210> SEQ ID NO 35
```

<211> LENGTH: 10
<212> TYPE: PRT
<213> ORGANISM: Artificial Sequence
<220> FEATURE:
<223> OTHER INFORMATION: synthetic construct - MYC Tag

<400> SEQUENCE: 35

```
Glu Gln Lys Leu Ile Ser Glu Glu Asp Leu
1               5                   10
```

<210> SEQ ID NO 36
<211> LENGTH: 1230
<212> TYPE: PRT
<213> ORGANISM: Homo sapiens

<400> SEQUENCE: 36

```
Met Ser Ala Leu Cys Trp Gly Arg Gly Ala Ala Gly Leu Lys Arg Ala
1               5                   10                  15

Leu Arg Pro Cys Gly Arg Pro Gly Leu Pro Gly Lys Glu Gly Thr Ala
            20                  25                  30

Gly Gly Val Cys Gly Pro Arg Arg Ser Ser Ser Ala Ser Pro Gln Glu
        35                  40                  45

Gln Asp Gln Asp Arg Arg Lys Asp Trp Gly His Val Glu Leu Leu Glu
    50                  55                  60

Val Leu Gln Ala Arg Val Arg Gln Leu Gln Ala Glu Ser Val Ser Glu
65                  70                  75                  80

Val Val Val Asn Arg Val Asp Val Ala Arg Leu Pro Glu Cys Gly Ser
                85                  90                  95

Gly Asp Gly Ser Leu Gln Pro Pro Arg Lys Val Gln Met Gly Ala Lys
            100                 105                 110

Asp Ala Thr Pro Val Pro Cys Gly Arg Trp Ala Lys Ile Leu Glu Lys
        115                 120                 125

Asp Lys Arg Thr Gln Gln Met Arg Met Gln Arg Leu Lys Ala Lys Leu
    130                 135                 140

Gln Met Pro Phe Gln Ser Gly Glu Phe Lys Ala Leu Thr Arg Arg Leu
145                 150                 155                 160

Gln Val Glu Pro Arg Leu Leu Ser Lys Gln Met Ala Gly Cys Leu Glu
                165                 170                 175

Asp Cys Thr Arg Gln Ala Pro Glu Ser Pro Trp Glu Glu Gln Leu Ala
            180                 185                 190

Arg Leu Leu Gln Glu Ala Pro Gly Lys Leu Ser Leu Asp Val Glu Gln
        195                 200                 205

Ala Pro Ser Gly Gln His Ser Gln Ala Gln Leu Ser Gly Gln Gln Gln
    210                 215                 220

Arg Leu Leu Ala Phe Phe Lys Cys Cys Leu Leu Thr Asp Gln Leu Pro
225                 230                 235                 240

Leu Ala His His Leu Leu Val Val His His Gly Gln Arg Gln Lys Arg
                245                 250                 255

Lys Leu Leu Thr Leu Asp Met Tyr Asn Ala Val Met Leu Gly Trp Ala
            260                 265                 270

Arg Gln Gly Ala Phe Lys Glu Leu Val Tyr Val Leu Phe Met Val Lys
        275                 280                 285

Asp Ala Gly Leu Thr Pro Asp Leu Leu Ser Tyr Ala Ala Ala Leu Gln
    290                 295                 300

Cys Met Gly Arg Gln Asp Gln Asp Ala Gly Thr Ile Glu Arg Cys Leu
305                 310                 315                 320
```

-continued

```
Glu Gln Met Ser Gln Glu Gly Leu Lys Leu Gln Ala Leu Phe Thr Ala
                325                 330                 335

Val Leu Leu Ser Glu Glu Asp Arg Ala Thr Val Leu Lys Ala Val His
            340                 345                 350

Lys Val Lys Pro Thr Phe Ser Leu Pro Pro Gln Leu Pro Pro Pro Val
        355                 360                 365

Asn Thr Ser Lys Leu Leu Arg Asp Val Tyr Ala Lys Asp Gly Arg Val
    370                 375                 380

Ser Tyr Pro Lys Leu His Leu Pro Leu Lys Thr Leu Gln Cys Leu Phe
385                 390                 395                 400

Glu Lys Gln Leu His Met Glu Leu Ala Ser Arg Val Cys Val Val Ser
                405                 410                 415

Val Glu Lys Pro Thr Leu Pro Ser Lys Glu Val Lys His Ala Arg Lys
            420                 425                 430

Thr Leu Lys Thr Leu Arg Asp Gln Trp Glu Lys Ala Leu Cys Arg Ala
        435                 440                 445

Leu Arg Glu Thr Lys Asn Arg Leu Glu Arg Glu Val Tyr Glu Gly Arg
    450                 455                 460

Phe Ser Leu Tyr Pro Phe Leu Cys Leu Leu Asp Glu Arg Glu Val Val
465                 470                 475                 480

Arg Met Leu Leu Gln Val Leu Gln Ala Leu Pro Ala Gln Gly Glu Ser
                485                 490                 495

Phe Thr Thr Leu Ala Arg Glu Leu Ser Ala Arg Thr Phe Ser Arg His
            500                 505                 510

Val Val Gln Arg Gln Arg Val Ser Gly Gln Val Gln Ala Leu Gln Asn
        515                 520                 525

His Tyr Arg Lys Tyr Leu Cys Leu Leu Ala Ser Asp Ala Glu Val Pro
    530                 535                 540

Glu Pro Cys Leu Pro Arg Gln Tyr Trp Glu Glu Leu Gly Ala Pro Glu
545                 550                 555                 560

Ala Leu Arg Glu Gln Pro Trp Pro Leu Pro Val Gln Met Glu Leu Gly
                565                 570                 575

Lys Leu Leu Ala Glu Met Leu Val Gln Ala Thr Gln Met Pro Cys Ser
            580                 585                 590

Leu Asp Lys Pro His Arg Ser Ser Arg Leu Val Pro Val Leu Tyr His
        595                 600                 605

Val Tyr Ser Phe Arg Asn Val Gln Gln Ile Gly Ile Leu Lys Pro His
    610                 615                 620

Pro Ala Tyr Val Gln Leu Leu Glu Lys Ala Ala Glu Pro Thr Leu Thr
625                 630                 635                 640

Phe Glu Ala Val Asp Val Pro Met Leu Cys Pro Pro Leu Pro Trp Thr
                645                 650                 655

Ser Pro His Ser Gly Ala Phe Leu Leu Ser Pro Thr Lys Leu Met Arg
            660                 665                 670

Thr Val Glu Gly Ala Thr Gln His Gln Glu Leu Leu Glu Thr Cys Pro
        675                 680                 685

Pro Thr Ala Leu His Gly Ala Leu Asp Ala Leu Thr Gln Leu Gly Asn
    690                 695                 700
```

```
Cys Ala Trp Arg Val Asn Gly Arg Val Leu Asp Leu Val Leu Gln Leu
705                 710                 715                 720

Phe Gln Ala Lys Gly Cys Pro Gln Leu Gly Val Pro Ala Pro Pro Ser
                725                 730                 735

Glu Ala Pro Gln Pro Pro Glu Ala His Leu Pro His Ser Ala Ala Pro
            740                 745                 750

Ala Arg Lys Ala Glu Leu Arg Arg Glu Leu Ala His Cys Gln Lys Val
        755                 760                 765

Ala Arg Glu Met His Ser Leu Arg Ala Glu Ala Leu Tyr Arg Leu Ser
    770                 775                 780

Leu Ala Gln His Leu Arg Asp Arg Val Phe Trp Leu Pro His Asn Met
785                 790                 795                 800

Asp Phe Arg Gly Arg Thr Tyr Pro Cys Pro Pro His Phe Asn His Leu
                805                 810                 815

Gly Ser Asp Val Ala Arg Ala Leu Leu Glu Phe Ala Gln Gly Arg Pro
            820                 825                 830

Leu Gly Pro His Gly Leu Asp Trp Leu Lys Ile His Leu Val Asn Leu
        835                 840                 845

Thr Gly Leu Lys Lys Arg Glu Pro Leu Arg Lys Arg Leu Ala Phe Ala
    850                 855                 860

Glu Glu Val Met Asp Asp Ile Leu Asp Ser Ala Asp Gln Pro Leu Thr
865                 870                 875                 880

Gly Arg Lys Trp Trp Met Gly Ala Glu Glu Pro Trp Gln Thr Leu Ala
                885                 890                 895

Cys Cys Met Glu Val Ala Asn Ala Val Arg Ala Ser Asp Pro Ala Ala
            900                 905                 910

Tyr Val Ser His Leu Pro Val His Gln Asp Gly Ser Cys Asn Gly Leu
        915                 920                 925

Gln His Tyr Ala Ala Leu Gly Arg Asp Ser Val Gly Ala Ala Ser Val
    930                 935                 940

Asn Leu Glu Pro Ser Asp Val Pro Gln Asp Val Tyr Ser Gly Val Ala
945                 950                 955                 960

Ala Gln Val Glu Val Phe Arg Arg Gln Asp Ala Gln Arg Gly Met Arg
                965                 970                 975

Val Ala Gln Val Leu Glu Gly Phe Ile Thr Arg Lys Val Val Lys Gln
            980                 985                 990

Thr Val Met Thr Val Val Tyr Gly  Val Thr Arg Tyr Gly  Gly Arg Leu
        995                 1000                 1005

Gln Ile  Glu Lys Arg Leu Arg  Glu Leu Ser Asp Phe  Pro Gln Glu
    1010                 1015                 1020

Phe Val  Trp Glu Ala Ser His  Tyr Leu Val Arg Gln  Val Phe Lys
    1025                 1030                 1035

Ser Leu  Gln Glu Met Phe Ser  Gly Thr Arg Ala Ile  Gln His Trp
    1040                 1045                 1050

Leu Thr  Glu Ser Ala Arg Leu  Ile Ser His Met Gly  Ser Val Val
    1055                 1060                 1065

Glu Trp  Val Thr Pro Leu Gly  Val Pro Val Ile Gln  Pro Tyr Arg
    1070                 1075                 1080
```

-continued

```
Leu Asp  Ser Lys Val Lys Gln  Ile Gly Gly Gly Ile  Gln Ser Ile
    1085                 1090                 1095

Thr Tyr  Thr His Asn Gly Asp  Ile Ser Arg Lys Pro  Asn Thr Arg
    1100                 1105                 1110

Lys Gln  Lys Asn Gly Phe Pro  Pro Asn Phe Ile His  Ser Leu Asp
    1115                 1120                 1125

Ser Ser  His Met Met Leu Thr  Ala Leu His Cys Tyr  Arg Lys Gly
    1130                 1135                 1140

Leu Thr  Phe Val Ser Val His  Asp Cys Tyr Trp Thr  His Ala Ala
    1145                 1150                 1155

Asp Val  Ser Val Met Asn Gln  Val Cys Arg Glu Gln  Phe Val Arg
    1160                 1165                 1170

Leu His  Ser Glu Pro Ile Leu  Gln Asp Leu Ser Arg  Phe Leu Val
    1175                 1180                 1185

Lys Arg  Phe Cys Ser Glu Pro  Gln Lys Ile Leu Glu  Ala Ser Gln
    1190                 1195                 1200

Leu Lys  Glu Thr Leu Gln Ala  Val Pro Lys Pro Gly  Ala Phe Asp
    1205                 1210                 1215

Leu Glu  Gln Val Lys Arg Ser  Thr Tyr Phe Phe Ser
    1220                 1225                 1230
```